United States Patent
Francis et al.

(10) Patent No.: US 10,835,146 B2
(45) Date of Patent: Nov. 17, 2020

(54) AUTONOMOUS BRAIN-MACHINE INTERFACE

(71) Applicant: The Research Foundation for the State University of New York, Albany, NY (US)

(72) Inventors: Joseph T. Francis, Albany, NY (US); Venkata S. Aditya Tarigoppula, Albany, NY (US); Brandi T. Marsh, Albany, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 339 days.

(21) Appl. No.: 15/534,956

(22) PCT Filed: Dec. 11, 2015

(86) PCT No.: PCT/US2015/065377
§ 371 (c)(1),
(2) Date: Jun. 9, 2017

(87) PCT Pub. No.: WO2016/094862
PCT Pub. Date: Jun. 16, 2016

(65) Prior Publication Data
US 2019/0025917 A1    Jan. 24, 2019

Related U.S. Application Data

(60) Provisional application No. 62/091,398, filed on Dec. 12, 2014.

(51) Int. Cl.
*A61B 5/0482* (2006.01)
*A61B 5/0476* (2006.01)
(Continued)

(52) U.S. Cl.
CPC ...... *A61B 5/0482* (2013.01); *A61B 5/04001* (2013.01); *A61B 5/0476* (2013.01);
(Continued)

(58) Field of Classification Search
None
See application file for complete search history.

(56) References Cited

U.S. PATENT DOCUMENTS

| 5,638,826 A * | 6/1997 | Wolpaw ............ G06F 3/015 340/4.11 |
| 2004/0073414 A1 * | 4/2004 | Bienenstock ...... G06F 3/015 703/2 |

(Continued)

OTHER PUBLICATIONS

Ferrez et al. EEG-Based Brain-Computer Interaction: Improved Accuracy by Automatic Single-Trial Error Detection. Advances in Neural Information Processing Systems 20. (Year: 2007).*

(Continued)

*Primary Examiner* — Etsub D Berhanu
(74) *Attorney, Agent, or Firm* — Heslin Rothenberg Farley & Mesiti P.C.

(57) ABSTRACT

A reinforcement learning brain-machine interface (RL-BMI) can have a policy that governs how detected signals, emanating from a motor cortex of a subject's brain, are translated into action. The policy can be improved by detecting a motor signal having a characteristic and emanating from the motor cortex. The system can provide, to a device and based on (i) the motor signal and (ii) an instruction policy, a command signal resulting in a first action by a device. Additionally, an evaluation signal, emanating from the motor cortex in response to the first action, can also be detected. With the foregoing information, the system can adjust the policy based on the evaluation signal such that a subsequent motor signal, from the subject's brain, having (Continued)

the characteristic results in a second action, by the device, different from the first action, as needed.

22 Claims, 31 Drawing Sheets

(51) Int. Cl.
*G06F 3/01* (2006.01)
*A61B 5/04* (2006.01)
*A61F 2/68* (2006.01)
*A61F 2/70* (2006.01)
*G06N 3/04* (2006.01)
*G06N 3/06* (2006.01)

(52) U.S. Cl.
CPC ............... *A61F 2/68* (2013.01); *G06F 3/015* (2013.01); *A61F 2002/6827* (2013.01); *A61F 2002/704* (2013.01); *G06N 3/049* (2013.01); *G06N 3/0454* (2013.01); *G06N 3/061* (2013.01)

(56) References Cited

U.S. PATENT DOCUMENTS

| | | |
|---|---|---|
| 2005/0228515 A1 | 10/2005 | Mussalam |
| 2005/0273890 A1* | 12/2005 | Flaherty .............. A61B 5/0031 600/544 |
| 2007/0265841 A1 | 11/2007 | Tani |
| 2010/0137734 A1 | 6/2010 | Digiovanna |
| 2012/0022392 A1* | 1/2012 | Leuthardt .............. A61B 5/048 600/544 |
| 2012/0053442 A1* | 3/2012 | Sjaaheim ............. A61B 5/0478 600/383 |
| 2012/0143104 A1 | 6/2012 | Tee |
| 2014/0200432 A1 | 7/2014 | Banerji |
| 2014/0330404 A1 | 11/2014 | Abdelghani et al. |
| 2015/0091791 A1* | 4/2015 | Segal .................... G06F 16/436 345/156 |

OTHER PUBLICATIONS

Tankus et al. Cognitive-motor brain-machine interfaces. J Physiol Paris. Feb. 2014; 108(1):38-44. (Year: 2014).*

Zyga. Machine Translates Thoughts into Speech in Real Time. Medical press. Dec. 21, 2009. (Year: 2009).*

Chavarriaga et al. Errare machinale est: the use of error-related potentials in brain-machine interfaces. Frontiers in Neuroscience, Jul. 22, 2014.*

Prins et al., A confidence metric for using neurobiological feedback in actor-critic reinforcement learning based brain-machine interfaces, Frontiers in Neuroscience, May 26, 2014, 8:1-11.

* cited by examiner

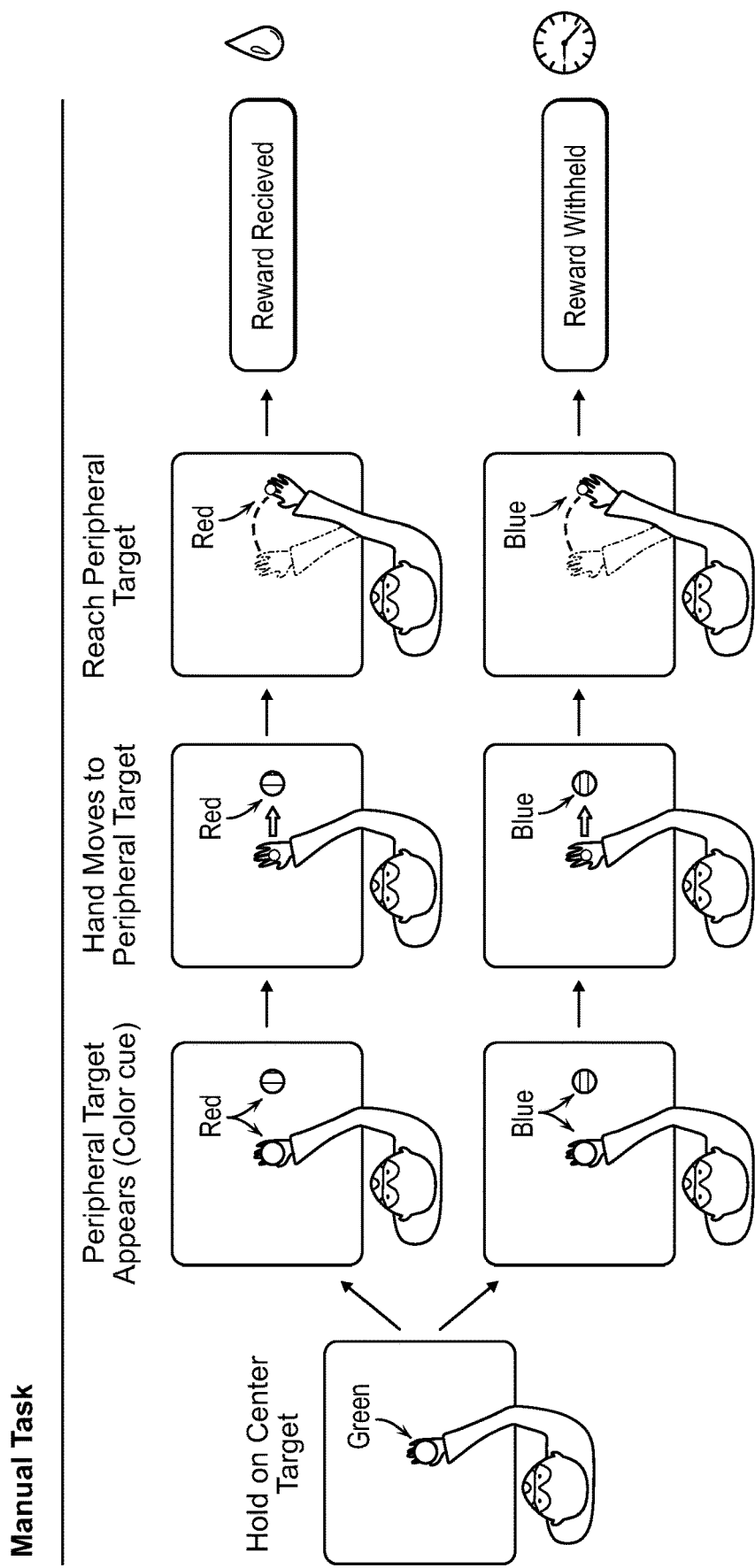

a) Observational Task 2 (OT2)

Monkey A Contralateral M1

Correlation with spike rate

Normalized spike rate

Average spike rate

Normalized spike rate (Blue) — — — Cue cursor
(Red) - - - - - Actual reward received

Average spike rate

(Red) ——— Reward trials
(Blue) ——— No Reward trials

State Dependence of Reward Modulation

Classifier Performance

AUTONOMOUS BRAIN-MACHINE INTERFACE

RELATED APPLICATION

This application is a U.S. National Stage application under 35 U.S.C. § 371 of International Patent Application No. PCT/US2015/065377, filed Dec. 11, 2015, which claims the benefit of and priority to U.S. Provisional Application No. 62/091,398, filed Dec. 12, 2014, titled Autonomous Brain-machine Interface. The entire contents of the above applications are incorporated herein by reference.

GOVERNMENT LICENSE RIGHTS

This invention was made with government support under grant N66001-10-C-2008 awarded by Defense Advanced Research Projects Agency. The Government has certain rights to this invention.

BACKGROUND

Brain-machine interfaces (BMIs) utilize mathematical algorithms to translate/decode users' intentions via their neural activity. To date most BMI systems have employed supervised learning, where one knows the users intention, actual motion, and target. This generally requires somewhat confined conditions, such as those found in a laboratory.

Many pathologies lead to loss of the ability to use one's limbs. These include physical injuries such as spinal cord injury or those injuries requiring amputation. Many neurological disorders such as stroke, amyotrophic lateral sclerosis (ALS), and syringomyelia, among others also can lead to functional loss of one or more limbs. Although the idea of replacing the lost or damaged limb with a prosthetic device is not a new concept, only recently has the technology been developed to allow the control of these devices via a neural signal from the user. Termed BMI, the technology of controlling external devices via signals from the brain is advancing towards true functional replacement of lost or damaged limbs. Sensorimotor BMIs strive to integrate the sensorimotor system and a neuroprosthetic thus providing people with sensory or motor disabilities the ability to interact with the world. Various sensorimotor BMI algorithms/architectures have been successfully shown to allow animals and humans to control external devices, where in these systems sensory feedback was via the intact visual system. Typically BMI systems utilize an exact error signal to adapt the BMI using supervised learning, which generally requires a controlled environment, such as a laboratory setting, and thus restrict the usefulness of these methods in complex evolving environments that we live in. In addition, neural input to BMIs changes with learning and time due to inherent instabilities such as loss of single units or addition of new units.

For decades neurophysiologists have worked on elucidating the function of the cortical sensorimotor control system from the standpoint of kinematics or dynamics. Recently computational neuroscientists have developed models that can emulate changes seen in the primary motor cortex during learning. However, these simulations rely on a key element that has yet to be demonstrated, which is a reward-like signal in primary sensorimotor cortex.

SUMMARY

According to some embodiments, disclosed herein is a Reinforcement Learning (RL) BMI system, which does not require information on reaching trajectories. According to some embodiments, disclosed herein is a BMI system that uses a reward expectation-like signal derived from the brain that guides updating of the system without requiring intervention from the experimenter/practitioner.

The primary motor cortex (M1) of non-human primates carries information not only useful for decoding intention of movement, but also carries evaluative information such as reward expectation which can be extracted on a moment-to-moment basis to adapt and improve a RL agent. RL based systems only need a simple scalar evaluative feedback that can even be derived from the brain itself. M1 itself has such reward expectation like information. According to some embodiments, disclosed herein is an autonomous BMI utilizing a single brain region (e.g., primary motor cortex, or M1), which carries information on the intended movement as well as the evaluative information, such as reward expectation.

The concept of reinforcement learning can be used in transitioning BMIs to novel and unstable environments. Reinforcement learning plays an important role in modifying and defining the behavior of animals. Learning in this manner involves utilizing prior experience to adapt one's behavior to maximize future rewards. This allows the animal to adapt to a changing environment and thus increasing the probability of its survival. Particularly useful may be the actor-critic reinforcement learning architecture, where the actor is the portion of the system that decodes neural activity into actions and the critic decodes the neural activity from the same region or another into an evaluative signal used to update the actor. One can put these ideas in terms of making a reaching movement. If the actor decodes the neural activity as indicating a rightward movement, which the BMI system then makes, but the evaluative signal after this movement indicates "things" are not going well, then the BMI system can learn that such neural activity should not be interpreted as moving to the right in the future. Likewise, if the actor made the correct move, which would be seen in the evaluative feedback, this could be used to increase the likelihood of making that movement when that neural pattern is seen in the future. In this manner the system will automatically update itself, if for instance there are changes in the neural input to the system. In the above idealization we assumed a perfect critic that could decode the evaluative signal from the neural activity. However, as further explained below in connection with FIG. 1A, one can imagine allowing the user the choice to intervene and inform the critic that it is wrong. This feedback would be binary, and could be delivered in many simple ways, such as speech if the user can do so, eye movements if they cannot use speech, etc. In short this would be a simple way to give the user control over the system if the system needed some updating and would not require input from an outside observer such as a medical practitioner or therapist.

According to some embodiments, single/multi-units and local field potentials in the primary motor cortex (M1) of non-human primates can be modulated by reward expectation during reaching movements, and this modulation is present even while subjects passively view cursor motions that are predictive of either reward or non-reward. After establishing this reward modulation, one can correctly classify rewarding vs. non-rewarding movements, on a moment-to-moment basis. This type of information could then be used in an actor-critic reinforcement learning architecture for an autonomous brain-machine interface: where the neural activity in M1 can be mapped to desired movements by a decoder (actor) and the corresponding reward expectation signal extracted from the same neural ensemble could be utilized as an evaluative signal (critic) of the performed action to allow subsequent autonomous BMI improvement. According to some embodiments, this is possible by utilizing the neural activity from the primary motor cortex alone.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1, Clause 13, or Clause 25. The other clauses can be presented in a similar manner.

Clause 1. A method for improving reinforcement learning by machine, the method comprising:

detecting a motor signal having a characteristic and emanating from a motor cortex of a subject's brain;

providing, to a device and based on (i) the motor signal and (ii) an instruction policy, a command signal resulting in a first action by the device;

detecting an evaluation signal emanating from the motor cortex in response to the first action; and adjusting the policy based on the evaluation signal such that a subsequent motor signal, emanating from the motor cortex and having the characteristic, results in a second action, by the device, different from the first action.

Clause 2. The method of Clause 1, wherein the device is a prosthetic device.

Clause 3. The method of Clause 1, wherein the first action is a movement by the device.

Clause 4. The method of Clause 1, wherein the device is a display and the first action is changing an appearance of the display.

Clause 5. The method of Clause 1, wherein the device is a prosthetic limb, the first action comprises a first movement made by the prosthetic limb, and the second action comprises a second movement made by the prosthetic limb, wherein the first movement and the second movement are different in at least one of position, direction, rotation, duration, speed, or acceleration.

Clause 6. The method of Clause 1, wherein the device comprises a speech generation device, the first action comprises a first sound generated by the speech generation device, and the second action comprises a second sound generated by the speech generation device, wherein the first sound and the second sound are different in at least one of pitch, volume, duration, or pronunciation.

Clause 7. The method of Clause 1, wherein the motor cortex is a primary motor cortex.

Clause 8. The method of Clause 1, wherein the motor cortex is a rostral primary motor cortex.

Clause 9. The method of Clause 1, further comprising receiving a sensory signal from a sensory cortex of the subject's brain, wherein adjusting the policy is further based on the sensory signal.

Clause 10. The method of Clause 1, wherein the command signal is generated from an algorithm of the policy.

Clause 11. The method of Clause 1, further comprising providing, to the device, a calibration signal having a calibration characteristic, the calibration signal not emanating from the subject's brain;

providing, to the device and based on (i) the calibration signal and (ii) the instruction policy, a calibration-command signal resulting in a third action by the device;

detecting a calibration-evaluation signal emanating from the motor cortex in response to the third action; and adjusting the policy based on the calibration-evaluation signal such that a subsequent motor signal, emanating from the motor cortex and having the calibration characteristic, results in a fourth action, by the device, different from the third action.

Clause 12. The method of Clause 1, wherein the evaluation signal corresponds to an expectation of the subject.

Clause 13. The method of Clause 1, wherein the subject is a mammal.

Clause 14. The method of Clause 1, wherein the subject is a human.

Clause 15. A system for improving reinforcement learning, the system comprising:

a motor signal detecting module configured to detect a motor signal having a characteristic and emanating from a motor cortex of a subject's brain;

a command module configured to provide, to a device and based on (i) the motor signal and (ii) an instruction policy, a command signal resulting in a first action by the device;

an evaluation signal detecting module configured to detect an evaluation signal emanating from the motor cortex in response to the first action; and an adjustment module configured to adjust the policy based on the evaluation signal such that a subsequent motor signal, emanating from the motor cortex and having the characteristic, results in a second action, by the device, different from the first action.

Clause 16. The system of Clause 15, wherein the device is a prosthetic device.

Clause 17. The system of Clause 15, wherein the first action is a movement by the device.

Clause 18. The system of Clause 15, wherein the device is a display and the first action is changing an appearance of the display.

Clause 19. The system of Clause 15, wherein the device is a prosthetic limb, the first action comprises a first movement made by the prosthetic limb, and the second action comprises a second movement made by the prosthetic limb, wherein the first movement and the second movement are different in at least one of position, direction, rotation, duration, speed, or acceleration.

Clause 20. The system of Clause 15, wherein the device comprises a speech generation device, the first action comprises a first sound generated by the speech generation device, and the second action comprises a second sound generated by the speech generation device, wherein the first sound and the second sound are different in at least one of pitch, volume, duration, or pronunciation.

Clause 21. The system of Clause 15, wherein the motor cortex is a primary motor cortex.

Clause 22. The system of Clause 15, wherein the motor cortex is a rostral primary motor cortex.

Clause 23. The system of Clause 15, further comprising a sensory signal receiving module configured to receive a sensory signal from a sensory cortex of the subject's brain, wherein adjusting the policy is further based on the sensory signal.

Clause 24. The system of Clause 15, wherein the command signal is generated from an algorithm of the policy.

Clause 25. The system of Clause 15, further comprising a calibration signal generating module configured to provide, to the device, a calibration signal having a calibration characteristic, the calibration signal not emanating from the subject's brain, wherein the command module is further configured to provide, to the device and based on (i) the calibration signal and (ii) the instruction policy, a calibration-command signal resulting in a third action by the device;

a calibration-evaluation signal detection module configured to detect a calibration-evaluation signal emanating from the motor cortex in response to the third action, wherein the adjustment module is configured to adjust the policy based on the calibration-evaluation signal such that a subsequent motor signal, emanating from the motor cortex and having the calibration characteristic, results in a fourth action, by the device, different from the third action.

Clause 26. The system of Clause 15, wherein the evaluation signal corresponds to an expectation of the subject.

Clause 27. The system of Clause 15, wherein the subject is a mammal.

Clause 28. The system of Clause 15, wherein the subject is a human.

Clause 29. A machine-readable medium comprising instructions for improving a reinforcement learning agent, the instructions comprising:

detecting a motor signal having a characteristic and emanating from a motor cortex of a subject's brain;

providing, to a device and based on (i) the motor signal and (ii) an instruction policy, a command signal resulting in a first action by the device;

detecting an evaluation signal emanating from the motor cortex in response to the first action; and adjusting the policy based on the evaluation signal such that a subsequent motor signal, emanating from the motor cortex and having the characteristic, results in a second action, by the device, different from the first action.

Clause 30. The machine-readable medium of Clause 29, wherein the device is a prosthetic device.

Clause 31. The machine-readable medium of Clause 29, wherein the first action is a movement by the device.

Clause 32. The machine-readable medium of Clause 29, wherein the device is a display and the first action is changing an appearance of the display.

Clause 33. The machine-readable medium of Clause 29, wherein the device is a prosthetic limb, the first action comprises a first movement made by the prosthetic limb, and the second action comprises a second movement made by the prosthetic limb, wherein the first movement and the second movement are different in at least one of position, direction, rotation, duration, speed, or acceleration.

Clause 34. The machine-readable medium of Clause 29, wherein the device comprises a speech generation device, the first action comprises a first sound generated by the speech generation device, and the second action comprises a second sound generated by the speech generation device, wherein the first sound and the second sound are different in at least one of pitch, volume, duration, or pronunciation.

Clause 35. The machine-readable medium of Clause 29, wherein the motor cortex is a primary motor cortex.

Clause 36. The machine-readable medium of Clause 29, wherein the motor cortex is a rostral primary motor cortex.

Clause 37. The machine-readable medium of Clause 29, wherein the instructions further comprise receiving a sensory signal from a sensory cortex of the subject's brain, wherein adjusting the policy is further based on the sensory signal.

Clause 38. The machine-readable medium of Clause 29, wherein the command signal is generated from an algorithm of the policy.

Clause 39. The machine-readable medium of Clause 29, wherein the instructions further comprise:

providing, to the device, a calibration signal having a calibration characteristic, the calibration signal not emanating from the subject's brain;

providing, to the device and based on (i) the calibration signal and (ii) the instruction policy, a calibration-command signal resulting in a third action by the device;

detecting a calibration-evaluation signal emanating from the motor cortex in response to the third action; and adjusting the policy based on the calibration-evaluation signal such that a subsequent motor signal, emanating from the motor cortex and having the calibration characteristic, results in a fourth action, by the device, different from the third action.

Clause 40. The machine-readable medium of Clause 29, wherein the evaluation signal corresponds to an expectation of the subject.

Clause 41. The machine-readable medium of Clause 29, wherein the subject is a mammal.

Clause 42. The machine-readable medium of Clause 29, wherein the subject is a human.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 2 illustrates a manual reward experiment task paradigm in accordance with certain embodiments of the disclosed subject matter.

DETAILED DESCRIPTION

Figure 1A:
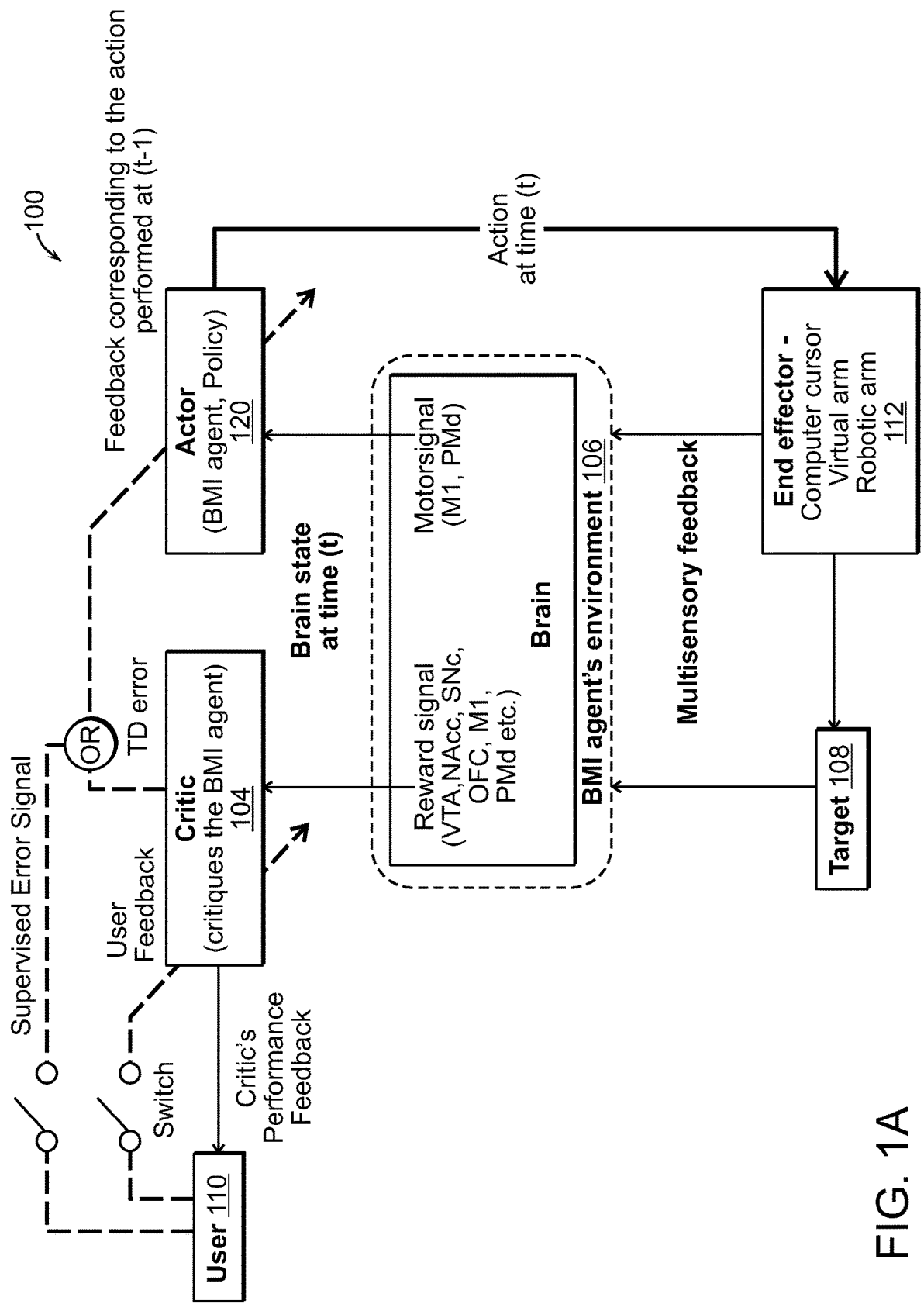
FIG. 1A illustrates an exemplary architecture of a reinforcement learning brain-machine interface (RL-BMI) environment in accordance with certain embodiments of the disclosed subject matter.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

This application incorporates by reference the entire contents of (a) U.S. Provisional Application No. 62/171,198, titled Diagnosis of Mild Traumatic Brain Injury, filed Jun. 4, 2015; (b) PCT International Application No. PCT/US2015/025,803, titled Biomimetic Multichannel Neurostimulation, filed Apr. 14, 2015; and (c) U.S. Provisional Application No. 61/979,425, titled Biomimetic Multichannel Neurostimulation, filed Apr. 14, 2014.

According to some embodiments, methods and systems of the subject technology can improve a reinforcement learning agent of a BMI. Motor signals from a motor cortex of the subject's brain can be received to determine and intended action to be taken by an external device. Command signals can be provided to the external device based on (1) the motor signals and (2) a policy of the reinforcement learning agent. As used herein, a policy can refer to one or more operating parameters of an RL-BMI architecture that governs how detected motor signals are translated into action by a device.

According to some embodiments, the operating policy of an RL-BMI can be improved to better correspond to an optimal policy that translates motor signals into optimal actions. An optimal policy maximizes an expected reward by performing the optimal action given a state in the environment. The RL agent strives to learn the optimal policy wherein a policy is the logic utilized by the actor to perform an action given a state to maximize its immediate and future rewards.

According to some embodiments, evaluation signals can be received from the same motor cortex that generated the motor signals. The evaluation signals can relate to an observed action executed by the external device. The observed action can be the result of the command signals. The observed action can also be observed by the subject to which the motor cortex belongs. According to some embodiments, evaluation signals received from the motor cortex can provide sufficient evaluative information to perform a comparison between the intended action and the observed action. Accordingly, the BMI can adjust the policy such that future command signals are generated based on the results of former command signals. For examples, in some embodiments, the future command signals (i.e., subsequent motor signals) can include causing a prosthetic limb or robot limb to move in varying degrees of position, direction, rotation, duration, speed, and/or acceleration. In some embodiments, the future command signals can include causing a speech generation device to generate sound in varying degrees of pitch, volume, duration, and/or pronunciation of one or more words, relative to sound generated from former command signals (i.e., prior motor signals).

Single units and local field potentials (LFPs) in the rostral primary motor cortex (M1) modulate differentially depending on the animal's expectation of reward in a given trial, thus providing an evaluative signal. Disclosed is the use of decoded neural signals from the motor cortex as an actor and a decoded reward expectation like signal from the same neural ensemble as an evaluative critic of a given action to automatically increase performance of the BMI. It is not necessary for this evaluative signal to come from M1, but this should allow for a minimally invasive implantation procedure, rather than going after deep brain structures. However, the concepts used herein certainly would work with an appropriate evaluative signal no matter the brain region. The Ventral Tegmental Area (VTA) and Substantia Nigra pars compacta (SNc) have been shown to contain dopaminergic neurons, which are believed to be an essential component of the reward system. It has been stated that dopaminergic neurons encoding value are located in ventral tegmental area (VTA) whereas dopaminergic neurons encoding motivation are located in substantia nigra pars compacta. Some of the major reward pathways (mesocorticol, mesolimbic, and nigrostriatal) stem out of these dopaminergic centers and directly/indirectly influence the primary motor cortex. Various deep brain structures such as the nucleus accumbens (NAcc), striatum, and cortical structures such as anterior cingulate cortex (ACC), medial and dorsal prefrontal cortex (mPFC, dPFC), orbitofrontal cortex (OFC), lateral intraparietal cortex (LIP), parietal reach region, supplementary motor area (SMA), premotor area (PM) and frontal eye field (FEF) are known to receive these reward related signals (directly or indirectly) through these pathways. Many of these regions are known to be the precursors of the primary motor cortex. In addition, dopamine receptors are found in M1 and it has been shown that dopamine modulation is necessary for synaptic plasticity in M1.

Reward expectation information in M1 and/or any other brain regions can be used as a part of Temporal Difference (TD) learning based reinforcement learning BMI such as, for example, Actor-Critic RL-BMI. FIG. 1A illustrates an exemplary architecture of a reinforcement learning brain-machine interface (RL-BMI) environment 100 in accordance with certain embodiments of the disclosed subject matter. The environment 100 includes an actor 102 (in some embodiments also referred to as an RL-BMI agent or a BMI agent), a critic 104, a brain 106, a target 108, a user 110, and an end effector 112. The components included in the environment 100 can be further broken down into more than one component and/or combined together in any suitable arrangement. Further, one or more components can be rearranged, changed, added, and/or removed. The actor 102 receives motor signal from the brain 106, and the critic 104 receives reward signal from the brain 106. The RL-BMI agent (actor) 102 can be viewed as trying to map the neural activity in the brain 106 pertaining to the intended action to an appropriate action of the external actuator (end effector) 112. The end effector 112 can include, without limitations, computer cursor, robotic arm, virtual arm, prosthetic limb, or speech generation device. The goal of the actor 102 (RL-BMI agent) is to maximize its immediate and future rewards provided by the critic 104. The multisensory feedback to the brain 106 with respect to the action performed results in a critic signal, which is labeled as rewarding or non-rewarding by a classifier. Such an evaluative scalar feedback is used to adapt the RL-BMI agent. The performance of the critic 104 can also be continuously monitored by the user 110 through a critic's performance feedback. In a scenario where a severe drop in the performance of the critic 104 is detected, the user 106 (which can be seen as a perfect critic) can act as a perfect source of feedback to update the critic 104 and subsequently the actor 102 if necessary. The user 110 can also switch between using supervised learning and RL to adapt the actor 102 in the suggested actor-critic framework.

Figure 1B:
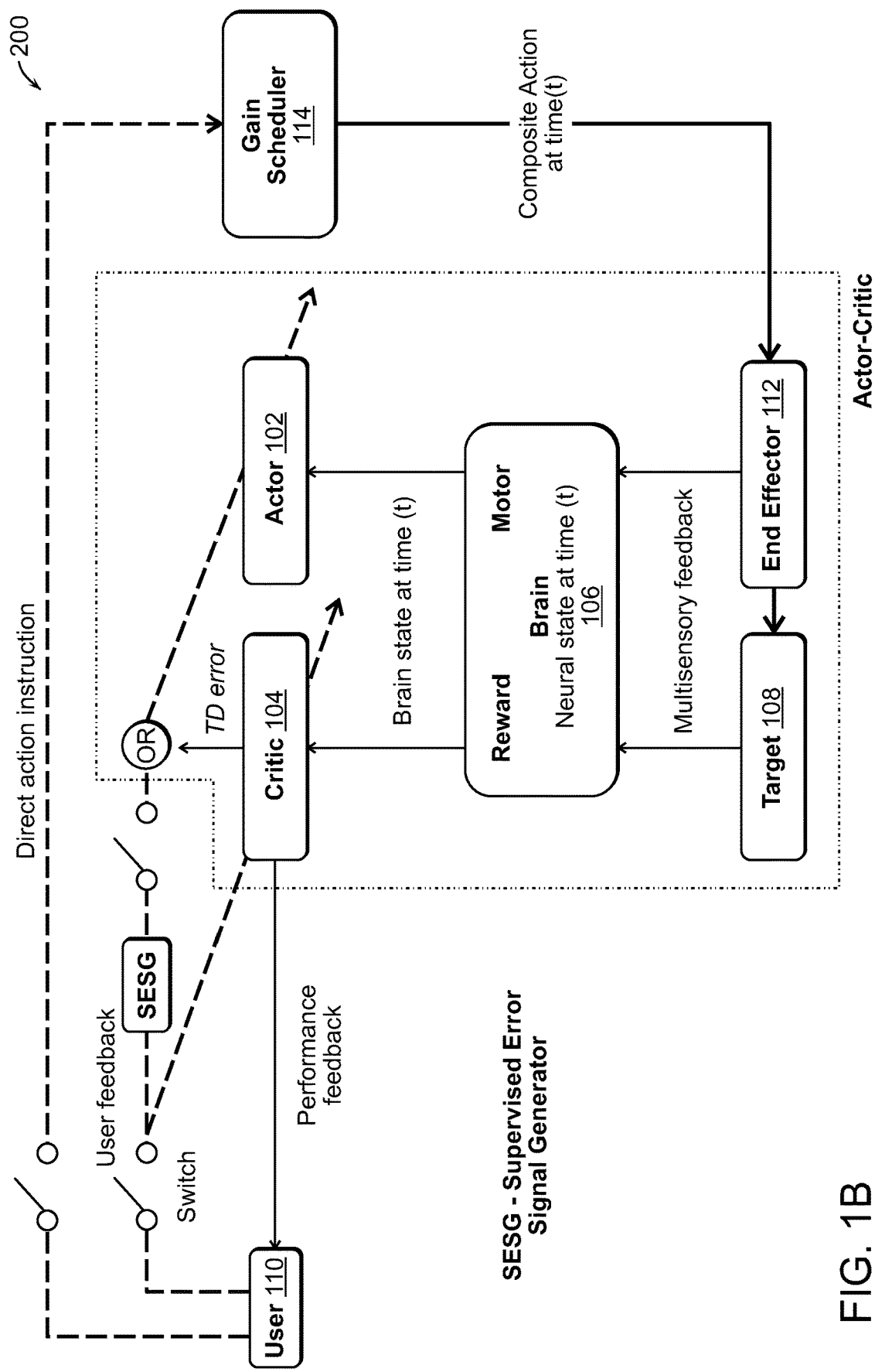
FIG. 1B illustrates an exemplary architecture of a supervised actor-critic reinforcement learning brain-machine interface (SAC-BMI) environment in accordance with certain embodiments of the disclosed subject matter.

FIG. 1B illustrates an exemplary architecture of a supervised actor-critic reinforcement learning brain machine interface (SAC-BMI) environment 200 in accordance with certain embodiments of the disclosed subject matter. The environment 200 includes an actor 102 (in some embodiments also referred to as an SAC-BMI agent), a critic 104, a brain 106, a target 108, a user 110, an end effector 112, and a gain scheduler 114. The components included in the environment 200 can be further broken down into more than one component and/or combined together in any suitable arrangement. Further, one or more components can be rearranged, changed, added, and/or removed. The actor 102 receives motor signal from the brain 106, and the critic 104 receives reward signal from the brain 106. The SAC-BMI agent (actor) 102 strives to decode the motor signal to result in an intended action of the external actuator (end effector) 112. The gain scheduler 114 outputs an action as the weighted sum of the actions given by the Actor 102 and the User (supervisor) 110. The goal of the actor (SAC-BMI agent) 102 is to maximize its immediate and future rewards provided by the critic 104. The multisensory feedback to the brain 106 with respect to the action performed results in a critic signal, which is labeled as rewarding or non-rewarding by a classifier. Such an evaluative scalar feedback is used to adapt the SAC-BMI agent 102. The performance of the critic 104 can also be continuously monitored by the user 106. In a scenario where a severe drop in the performance of the critic 104 is detected, the user 110 (which can be seen as a perfect critic) can act as a perfect source of feedback to update the critic 104 and subsequently the actor 102 if necessary. The user 110 can also switch between using supervised and reinforcement learning to adapt the actor in the suggested framework. The user 110 can update the critic 104 directly when required. Supervised Error Signal Generator (SESG) is capable of updating the actor 102 directly under the realm of supervised learning by providing an exact error when available. The user 110 can be one of the multiple inputs to SESG.

Traditionally the motor cortex has been theorized to carry information on either movement dynamics or kinematics. More recently the motor cortex has been viewed from a control-engineering and dynamical systems viewpoint. It has been shown that activity from the sensorimotor regions can be used to allow animals and humans to control external devices via a BMI. BMI systems are now being utilized to test and further the understanding of sensorimotor learning. Modulatory signals, such as dopaminergic drive, are involved for the induction of long term potentiation (LTP) in the motor cortex. Such a dopaminergic drive has been used in simulations to emulate motor cortical plasticity in conjunction with a BMI, as well as to control robotic limbs. To date there has been no proof of such neural modulation in the primary motor cortex (M1). Neural correlates of reward expectation have been found in a variety of cortical and non-cortical regions, many of which connect to M1. It has been shown that dopamine receptors exist in primate M1, and therefore one might expect dopamine modulation of this region.

It is important to determine if reward modulation would be seen in M1, from both a basic neuroscience perspective, as well as a biomedical engineering standpoint, for the generation of an autonomous BMI. If one could record a signal from the brain itself that tells us whether operations are going well, or not, such feedback could be utilized to adapt a BMI utilizing reinforcement learning.

we recorded neural activity bilaterally from M1 in macaques, while the animals either made manual-reaching movements to visually cued targets, or simply observed cursor trajectories to such targets. As illustrated below in connections with FIGS. 6-8, reward expectation was indicated either via the color of the target or via the trajectory of the feedback cursor toward or away from the target. According to some embodiments, systems and methods of the subject technology 1) allow expanding the current reward circuit map to include bilateral M1; 2) demonstrate that previously noted mirror-like neurons in M1 are also reward modulated and; 3) can be used in principal towards the development of an autonomous BMI.

The following examples are presented for the purpose of illustration only and are not intended to be limiting. For example, the parameters, including but not limited to, position, period, frequency, and percentage, that are used in the following examples are not intended to be limiting, and can be replaced by any suitable values that are appreciated by persons skilled in the art. The medicines and/or systems used in the following examples are not intended to be limiting, and can be replaced by any suitable medicines and/or systems that are appreciated by persons skilled in the art.

EXAMPLE 1

Experimental Setup and Behavioral Training

The use of animals in all procedures described here was approved by the Institutional Animal Care Use Committee (IACUC) of State University of New York (SUNY) Downstate Medical Center and supervised by the department of comparative medicine (DCM) of SUNY Downstate Medical Center. Two bonnet macaques (one male, Monkey A and one female, Monkey Z) were trained towards this work, which required completion of a center-out reaching task with the right arm resting in a robotic system in order to attain a juice reward. For example, in some embodiments, the system can be a robotic manipulandum system from KINARM, BKIN Technologies, ON, Canada. Although the animal's arm was partially obscured from its view, visual feedback of the hand's position was provided by a cursor that coincided with the position of the animal's third digit. Successful completion of a trial resulted in a small volume of juice being delivered to the animal and a failed trial resulted in no juice reward. Controlled water access (CWA) was used for training in accordance with guidelines established by the National Institutes of Health (NIH). Regardless of the number of successful trials completed in any given day, the animals were provided adequate water to maintain its weight. Each animal was provided free access to water at least one day per week and the weight of each animal was never allowed to drop below 95% of baseline determined before initiation of CWA. Beyond daily weighing to ensure the animal was not becoming dehydrated, signs of poor nutrition or dehydration were monitored for; these included monitoring urine and feces color and consistency, any abnormal behavioral cues, skin turgor, etc. If an animal showed any signs of distress or dropped below 95% of its baseline weight the animal would have been given access to free water and not used in any experiments for at least one week. However, at no time during this study period did any subjects described in this work require removal from training.

Surgery

All surgical procedures were conducted in compliance with guidelines set forth by the NIH Guide for the Care and Use of Laboratory Animals and were further approved by the SUNY Downstate IACUC. All surgical procedures were performed under general anesthesia, and aseptic conditions were maintained throughout. Anesthesia and animal preparation were performed directly or were supervised by members of the SUNY Division of Comparative Medicine (DCM) veterinary staff. Ketamine were used to induce anesthesia; isofluorane and fentanyl were used in maintenance of anesthesia. Dexamethasone was used to prevent inflammation during the procedures, and diuretics such as mannitol and furosemide were available to further reduce cerebral swelling if needed. All subjects were observed hourly for the first twelve hours post implantation and were provided with a course of antibiotics (for example, baytril and bicilin) and analgesics (for example, buprenorphine and rimadyl) commensurate with the recommendations of the DCM veterinary staff.

The procedure involved initial implantation with a head post to allow head fixation during training. For example, such head post can be a footed titanium head post from Crist Instrument, Hagerstown, Md. Head restraint of the animal is required for the experiments to ensure minimization of movement artifacts as well as to track the movement of the eyes. Implantation was performed following training to a sustained performance level of, for example, at least 90% correctly completed trials per training session. 96 channel platinum microelectrode arrays (for example, from Blackrock Microsystems, Salt Lake City, Utah) were implanted in the contralateral and ipsilateral primary motor cortex (M1) of Monkey A and Monkey Z respectively. Intraoperative determination of the areas of interest within somatosenaory cortex were made with sharp electrodes and the motor cortex lying immediately adjacent to these areas reflected across the central sulcus were implanted. The full implantation procedure has been described previously.

Behavioral Experiment

Following implantation each subject was allowed to recover with free access to water for two to three weeks before training is resumed. FIG. 2 illustrates a manual reward experiment task paradigm in accordance with certain embodiments of the disclosed subject matter. The reward experiment depicted in FIG. 2 required the animal to reach to a peripherally located target following a hold period within a central target. In this task the monkey used its right arm and there was a single peripheral target located at a distance to the right of a center target. In some embodiments, the distance between the single peripheral target and the center target can be, for example, 5 cm or any suitable distance that is appreciated by persons skilled in the art. To initiate a trial the animal was required to move and hold its hand inside the neutral colored central "start" position and hold for a period called a center hold period. In some embodiments, the center hold period can have a minimum of 325 ms or any other suitable duration. Following this first center hold period, the color of both the peripheral and start targets changed from a neutral color to a color (color cue)

informing the animal whether the completion of the trial would result in a reward (e.g., liquid reward) or no reward (e.g., liquid reward). Following this color change, the monkey was required to maintain its hand position within the start target for a second hold period before reaching to the peripheral target. In some embodiments, the second hold period can be 300 ms or any other suitable duration. Following this second hold period the animal was allowed to reach for the peripheral target, where the animal was required to maintain its hand position for a third hold period in order to complete the trial successfully. In some embodiments, the third hold period can be 325 ms or any other suitable duration. If the trial is of the rewarding type, a reward (e.g., a liquid reward) is dispensed for a reward period. In some embodiments, the reward period can be 250 ms or any other suitable duration. If the trial type is non-rewarding, no reward (e.g., no liquid reward) is dispensed. At any point if the animal failed to complete a trial the next trial initiated would be of the same type as the previously failed trial. In this way the animal is given an incentive to complete the non-rewarding trials the first time. In some embodiments, sessions are designed to constitute more rewarding trials and less non-rewarding trials for keeping the monkey interested in performing the task. For example, in some embodiments, two-thirds of the trials can be rewarding and one-third of the trials can be non-rewarding. Color cues indicating a rewarding or a non-rewarding trial can be switched as a control on a couple of days. In FIG. 2, a drop symbol represents reward, and a clock symbol represents no reward, i.e., passage of time.

Extracellular Unit Recordings

Once training resumed single unit activity was recorded while the subject performs the task. Recordings can be performed using externally synched multichannel acquisition processor systems such as ones from MAPs, Plexon Inc., Dallas, Tex. Signals were amplified, band pass filtered (for example, in some embodiments, between 170 Hz and 8 kHz), sampled at a frequency (for example, in some embodiments, at 40 kHz), subjected to thresholding, and units were identified by sorting using principal component methods using a software, such as, for example, a Sort-Client software from Plexon Inc., Dallas, Tex. In some embodiments, The data presented here were collected from the contralateral M1 (with respect to the right arm) of Monkey A and from the ipsilateral M1 (with respect to the right arm) of Monkey Z.

Electromyography

Surface gold disc electrodes (for example, form Grass Technologies) were sewn onto elastic bands and placed on the skin overlying muscle groups. Muscle groups tested included latissimus dorsi, biceps, deltoid, triceps, forearm extensors, and forearm flexors. Electromyography (EMG) signals are then acquired at certain sampling rate. For example, in some embodiments, the EMG signals were acquired through the acquisition processor system at a sampling rate of 2 kHz.

Data Analysis

Multivariate linear regression was performed on the neural data (for example, 100 ms bins) to fit and predict shoulder and elbow angles acquired during the manual task (See Table 1 for fits and predictions). Each 100 ms of position data was fit to, for example, 10 bins of neural data, corresponding to a second of causal information (See Table 1 for fits and predictions). This was performed to ascertain the location of the electrode array in the primary motor cortex. The total number of units acquired in each task per brain area ranged from, for example, 38 to 71. For example, in some cases, Monkey A had 71 contralateral M1 units and Monkey Z had 38 ipsilateral M1 units.

To negate speed, path length, and time to reward as the possible sources of differentiability observed in the neural ensemble's firing rate for rewarding vs. non-rewarding trials, we performed the following analysis. We pruned the trials such that non-rewarding trials with a maximum velocity, path length, and time to reward within one standard deviation of the rewarding trials were selected. Trials with double peaks in the velocity profile were also removed. Significant differentiability was still observed between the firing rates of the neural ensemble for rewarding and non-rewarding trials post the pruning process (data not shown). In addition, we found similar results to the ones presented in this disclosure during purely observational versions of these tasks indicating that differences in kinematics were not the root cause for differences seen in M1 for rewarding and non-rewarding trial types. Principal component analysis (PCA, princomp function in MATLAB) was also performed on the z-scored data recorded from all of the successful reaching trials. The PCA scores were separated into rewarding and non-rewarding trials and used as inputs to test and train classifiers (see below).

Classifiers

By using the PCA scores as inputs, a variety of classification methods were tested to determine the best method of predicting rewarding verses non-rewarding trials. The methods used for classification included both linear and quadratic discriminant analysis (classify function in Matlab) as well as the support vector machine technique (svmtrain & svmclassify function in Matlab). Repeated random sub-sampling cross validation was performed to quantify the performance of the classifiers.

Temporal Difference Reinforcement Learning (Actor-Critic RL)

The theory of 'reinforcement learning' formulates the environment as a Markov Decision Process. Given an environment and the current state of the actor (animals or automata) in the environment, RL suggests that the actor chooses an action not only to maximize its immediate expected reward but also its future expected rewards. The term environment in our case includes the neural activation patterns from M1. The logic utilized by the actor to perform an action given a state is called the policy. An action performed by the actor under a given policy leads it to a new state in the environment and the consequence of such an action is utilized as feedback to modify its behavior/policy. Experience as well as learning rate dictates how close the actor's policy is to the optimal policy. An optimal policy intends to maximize the expected reward by performing the optimal action given a state in the environment. A balance between exploration (of uncharted territory) and exploitation (of current knowledge) also defines an actor's behavior and its learning rate.

Temporal difference learning is a branch of reinforcement learning, containing qualities from both dynamic programming and Monte Carlo methods. In dynamic programming, a full model of the environment is available and necessary, whereas in Monte Carlo and temporal difference methods, a full model of the environment is not needed. Monte Carlo methods update their policies at the end of episode, where an episode could be a single reaching movement, while temporal difference methods can update their policies during an episode. Given the rational that a BMI user would like to correct his or her movements on the way to reaching a target and that, in real world situations, there is no model of the environment; TD learning is a logical RL algorithm to use.

Actor-critic methods are TD methods that have the actor (policy) and the critic (estimated value function or the evaluative feedback signal provider) exist as two independent entities. The critic, as stated earlier, criticizes the actions executed by the actor.

The RL agent strives to learn the optimal policy wherein a policy is the logic utilized by the actor to perform an action given a state to maximize its immediate and future rewards. The state-action value, $Q\pi(s,a)$, is the expected return starting from state 's' given that the RL agent executes the action 'a' in state 's' under a policy. Specifically, we use an ε-greedy policy as the actor and the Q learning paradigm, augmented with Eligibility Trace $Q(\lambda)$, as the actor's update rule. An eligibility trace is extremely useful in dealing with the credit assignment problem. The action with the highest Q value is selected 1-ε percent of the time (exploitation) whereas a random action is performed ε percent of the time (exploration) under the ε-greedy policy. There are also ways to change c given the systems performance as appreciated by persons skilled in the art.

In Q learning, the TD error equation is:
TD error: $r+\gamma^* \max_{a'} Q(s', a') - Q(s, a)$. All the neurons had a baseline firing rate. A tuning curve directed the degree of modulation with respect to the corresponding neuron's baseline firing rate given the direction of the target with respect to the present cursor position. Preferred directions of these neurons were assigned randomly. A spike was detected every time the membrane potential of a neuron surpassed, for example, 30 mV. The firing rates for these neurons were generated, for example, every 100 ms to provide a time scale close to firing rates observed during behavior.

Figure 5A:
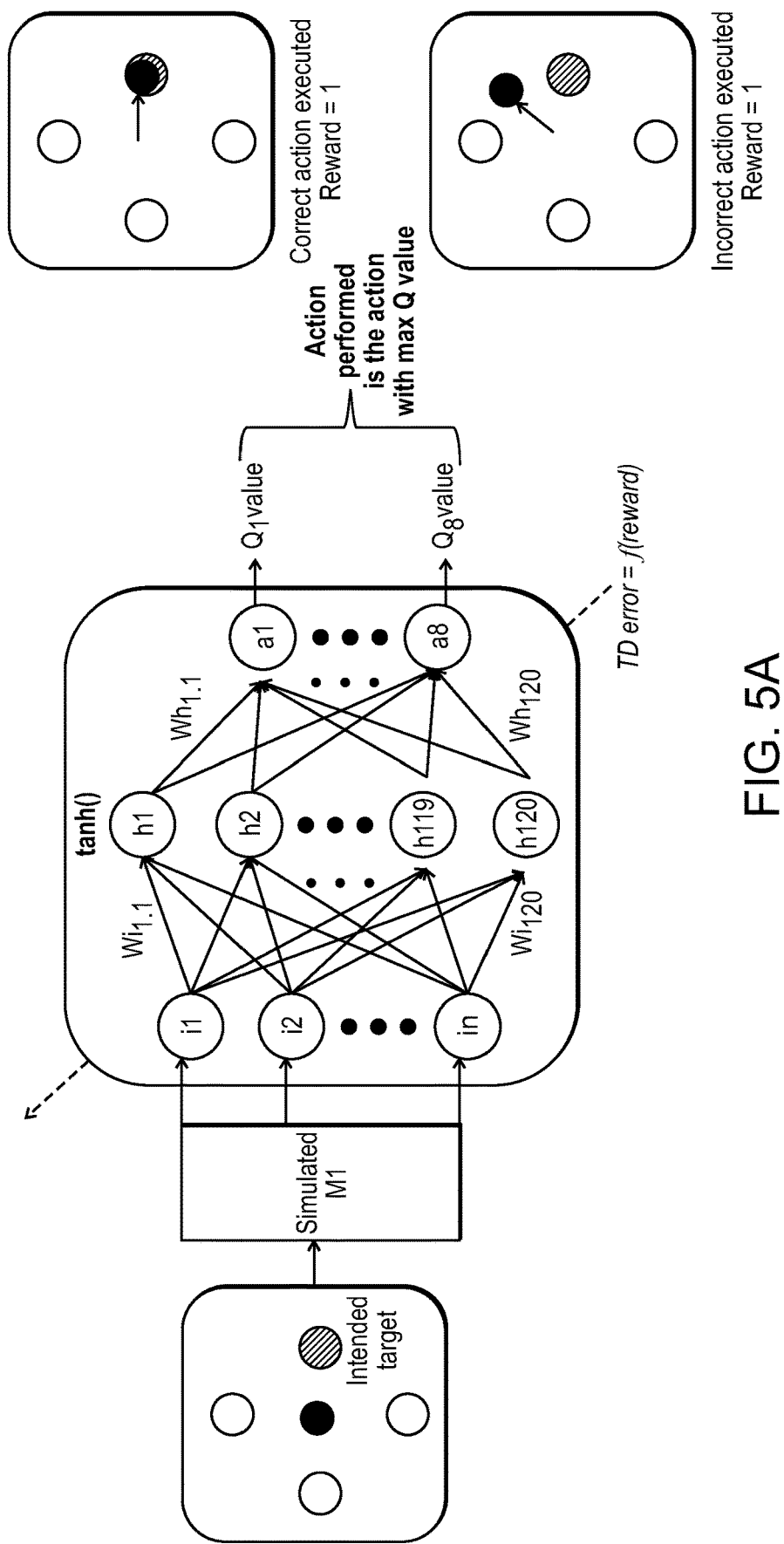
FIG. 5A illustrates a pictorial representation of the offline simulation architecture in accordance with certain embodiments of the disclosed subject matter.

FIG. 5A illustrates a pictorial representation of the offline simulation architecture in accordance with certain embodiments of the disclosed subject matter. As depicted in FIG. 5A, a center-out reaching task with 4 targets was designed. The simulated motor cortex had 80 neurons modeled as Izhikevich neurons. 60%, 25% and 15% of the neurons were designed to have unimodal, asymmetric and bimodal tuning curves respectively. The firing rates of the simulated M1 in a given trial were provided as input to the Multi-Layer Perceptron (MLP). MLP had one hidden layer with 120 units wherein the output of each unit is a nonlinear function (tan h) of the weighted inputs. MLP consisted of 8 outputs whose outputs were the state-action value for each available action. An action was executed by the RL agent based on the ε-greedy policy resulting in either a correct (reward=1) or an incorrect movement (reward=−1) of the cursor. The temporal difference error, which utilizes the scalar reward value, is used to update the weights of the MLP through backpropagation. As depicted in FIG. 5A, The task involved moving a cursor from the center of the task plane to one of four peripherally placed targets by decoding the intention of this simulated motor cortex given the possibility of a movement by the cursor in eight directions at any given time (the first direction is to the right and the remaining 7 directions are at 45-degree intervals to the first direction) utilizing the e-greedy policy presented earlier.

The target direction in a given trial changed each neuron's firing rate with respect to its baseline activity based on its respective tuning curves. That is, given a target in the left direction, the neurons that had their preferred direction to the left fired at their maximum firing rate whereas the remaining neurons modulated their firing based on their tuning curve. Using the output of the simulated neural ensemble as the input to an artificial neural network the Q value for each potential action was determined. Specifically, a multilayer perceptron (MLP) with a single hidden layer consisting of, for example, 120 units was used to calculate the Q value given an input from the neural ensemble. 99% of the time the action with the highest Q value was executed (the "greedy" part of the e-greedy policy), and the other 1% of the time a random action was taken (the exploratory rate, the 'ε' part of the ε-greedy policy). Exploratory rate, defined as the percentage of steps in which an action is executed randomly irrespective of its optimality at a given state, was set at 1% ('ε' part of ε-greedy policy). The random exploration allows for discovery of new solutions by the RL agent, useful especially in an altering environment. Update of the weights of MLP was performed by backpropagation of a qualitative error signal, 'TD error*eligibility trace', calculated utilizing the immediate reward it received based on the correct or incorrect action performed. A correct action resulted in +1 as the immediate reward whereas an incorrect action was awarded with −1. The implementation of this strategy allowed the MLP to learn the optimal mapping between the simulated neural output and proper control of the task.

Results

Modulation in M1 with Respect to Reward

The data obtained from these experiments was binned at, for example, 100 ms. For every unit, a check was made to see if the distribution of the data came from a normally distributed population (for example, using Shapiro—Wilk test, p<0.05) prior to deciding if we can perform rANOVA or ttest on it. Most of the units rejected the null hypothesis of the Shapiro-Wilk test hence rANOVA or ttest were not valid tests to measure differentiability between rewarding and non-rewarding trials.

Figure 3A:
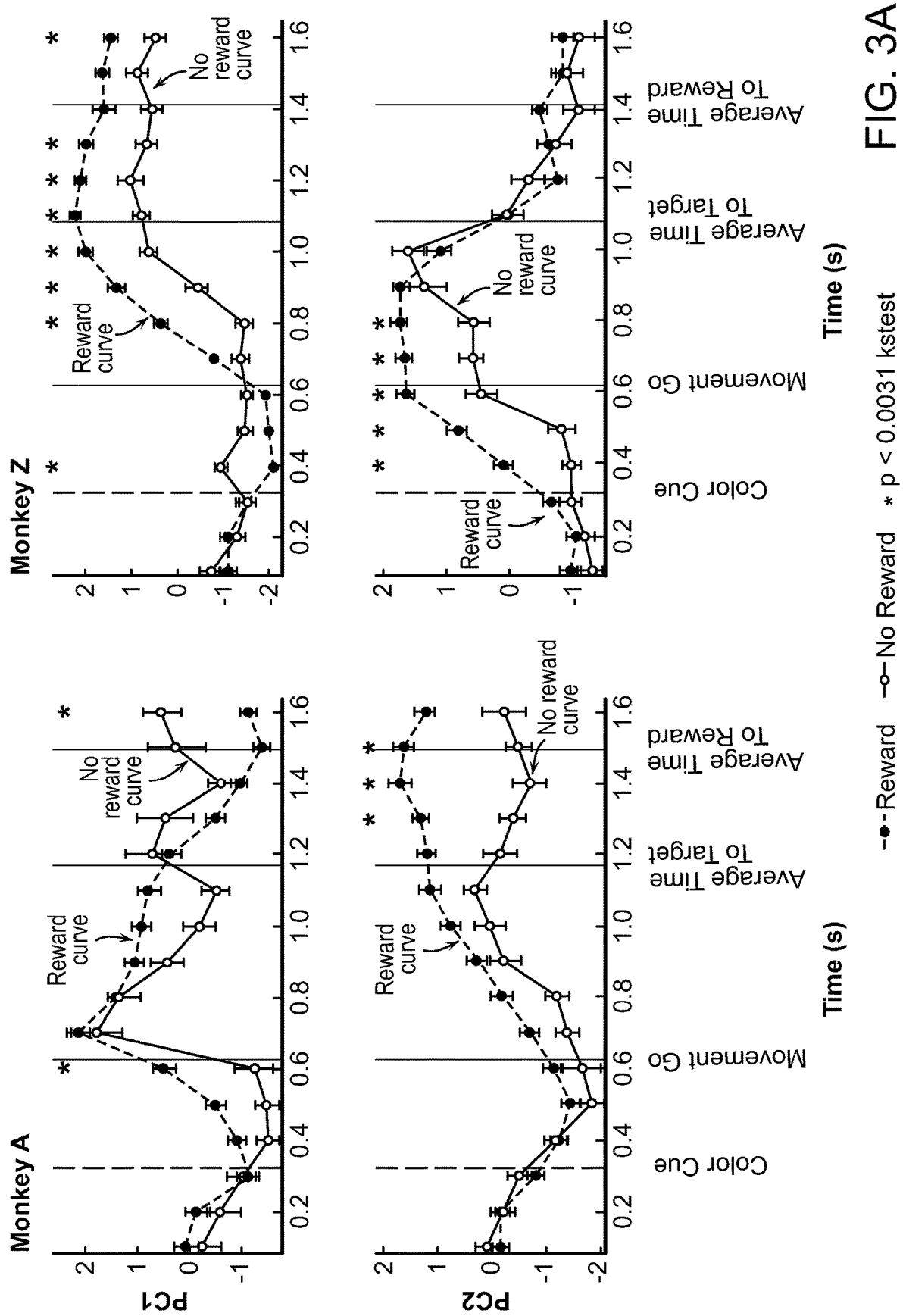
FIG. 3A illustrates mean and standard error of principal component scores across rewarding and non-rewarding trials in accordance with certain embodiments of the disclosed subject matter.

Wilcoxon test was performed for each instant (time bin) of the peri-movement time period of a given unit to see if the difference between the neural firing rates across the rewarding trials for a given bin and the neural firing rates across the non-rewarding trials for the same bin had a zero median. Similar analysis was performed on the Principal Component (PC) scores as shown in FIG. 3A. FIG. 3A shows mean and standard error of PC scores across rewarding and non-rewarding trials for Monkey A and Z in accordance with certain embodiments of the disclosed subject matter. PC scores were calculated on the standard scores (z-scores) of the neural data binned at 100 ms. Two sample Kolmogorov-Smirnov test was performed at every bin (neural data was binned in 100 ms bins) to test the significance of the differentiability between the rewarding and non-rewarding PC score distribution at the corresponding time point. Time points with an asterisk had a significant difference (kstest with bonferroni correction, p<0.0031) between the rewarding and non-rewarding PC score distribution. The rewarding and non-rewarding PC scores were significantly different at multiple time points post the color cue. The color of the center start target and the peripheral target (color cue) informed the monkey if it would receive a juice reward post a successfully completed trial. Mean PC scores across rewarding and non-rewarding trials were also significantly different (N-way ANOVA followed by post hoc multiple comparison test). In FIG. 3A, PC1 indicates Principal Component 1; PC2 indicates Principal Component 2; and kstest indicates Kolmogorov-Smirnov test (with bonferroni correction, p<0.0031).

Figure 3B:
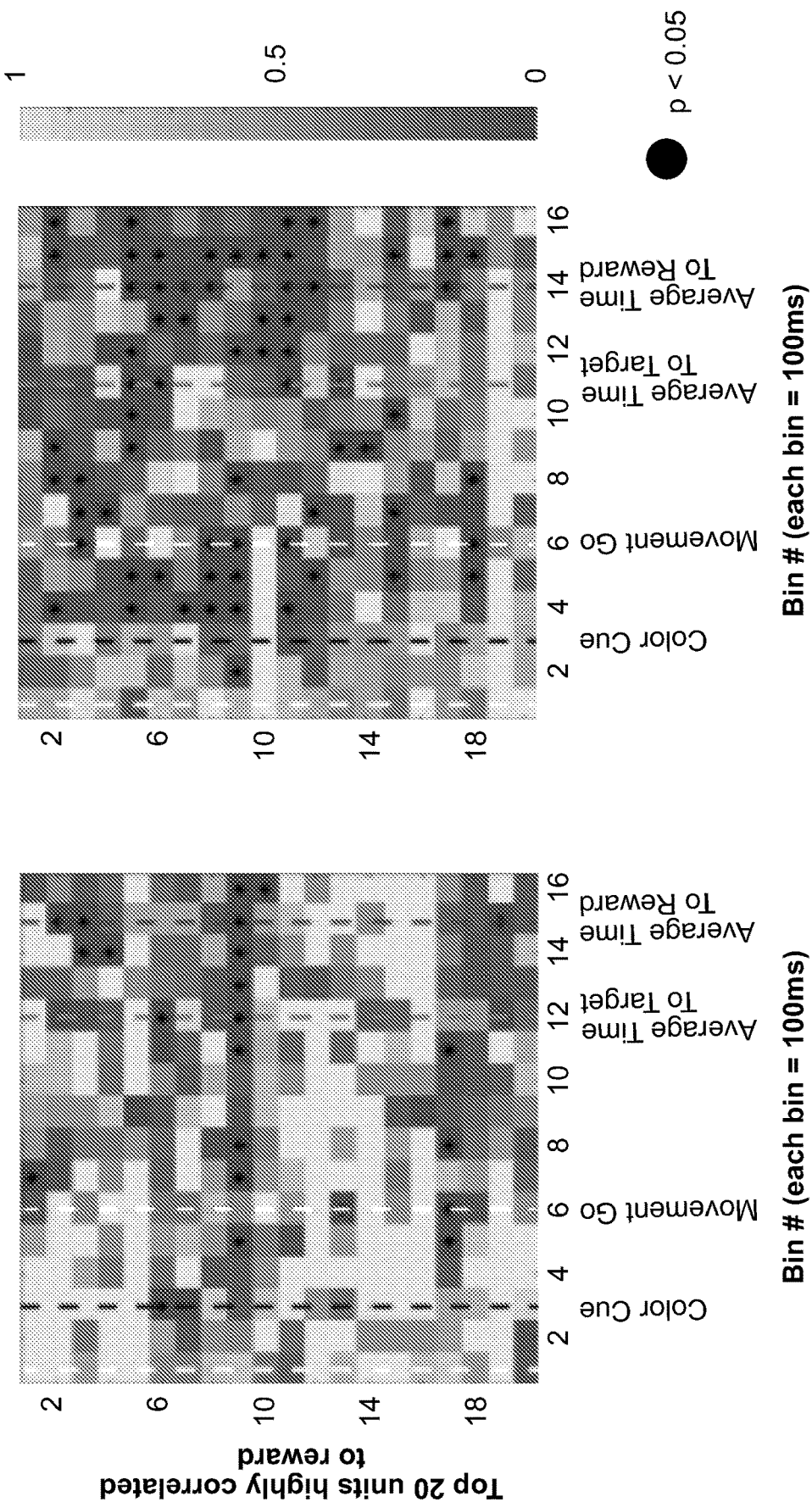
FIG. 3B illustrates p values of Wilcoxon test for each instant (time bin) of a given unit in accordance with certain embodiments of the disclosed subject matter.

If the null hypothesis was rejected at p<0.05, the corresponding time bin was displayed by a black '*' in FIG. 3B. The units were ranked with respect to their absolute correlation to the variable 'reward'. The variable reward was created by assigning +1 or −1 every 100 ms bin of a rewarding or a non-rewarding trial respectively. Only the top 20 units of the entire neural ensemble that have the maximum absolute correlation with reward for each monkey are shown in FIG. 3B.

The color cue period, which informs the monkey whether the trial is rewarding or not, resulted in a reward expectation. A differentiable reward expectation with respect to the trial type manifested itself as a differentiable neural modulation of M1 post color cue. Color cues for rewarding and non-rewarding trials were switched as a control to negate color as the possible cause of the differentiable neural modulation. There was no significant difference in the neural ensemble's representation of reward pre and post color switch (data not shown).

Classifier Results

Figure 4:
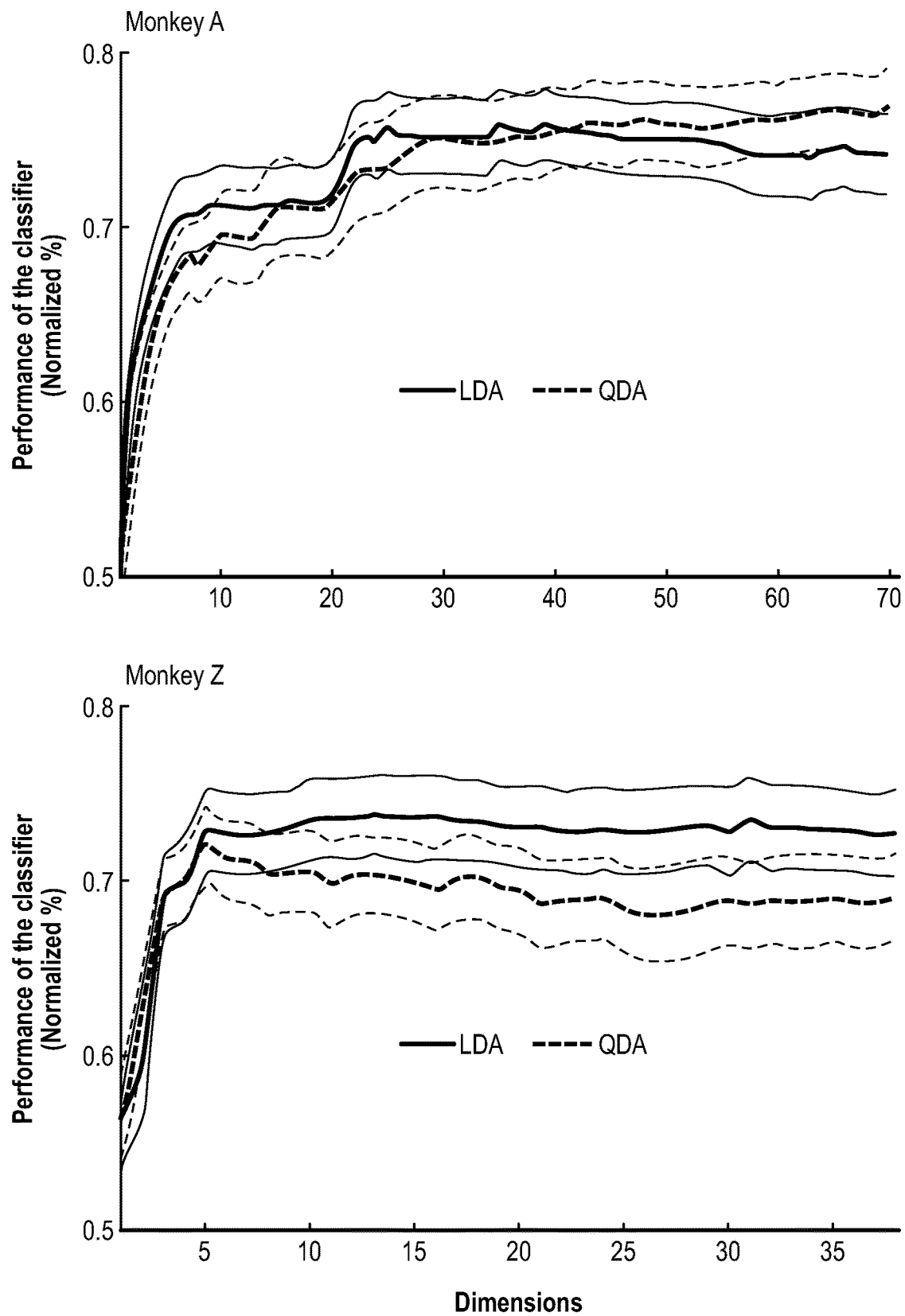
FIG. 4 illustrates linear discriminant analysis and quadratic discriminant analysis results on manual reward experiment for animals in accordance with certain embodiments of the disclosed subject matter.

Training and prediction was performed on 70% and 30% of the data (PCA scores) respectively. The mean and the standard deviation of the repeated random sub-sampling validations (100 times) of linear and quadratic discriminant analysis (LDA and QDA) as reward classifiers are presented in FIG. 4. FIG. 4 shows LDA and QDA analysis results on manual reward experiment for Monkey A and Monkey Z. See Behavioral experiment (Manual reward experiment) for further details on the task. The performance of the classifier (normalized %) on the testing data is shown here with respect to the number of principal components (dimensions) used. PC scores were calculated on the standard scores (z-scores) of the neural data binned at 100 ms. Training and testing was performed on 70% and 30% of the randomized data (PCA scores) respectively. Repeated random sub-sampling validation (100 times) of the LDA and QDA was performed for each point on the X axis. The classifiers were able to discriminate rewarding from non-rewarding data with above 70% accuracy. The highest success rate achieved by the classifiers was equal to or above 75%. We also tested the performance of LDA and QDA with respect to the number of PC components (dimensions) that were being used. Around 22 principal components for Monkey A and 6 principal components were deemed sufficient to result in the maximum performance. The performance plateaued post the 'optimal' number of principal components. Similar results were obtained by using support vector machines (data not shown). These results show that rewarding and non-rewarding trials can be differentiated on a 100 ms time scale.

Offline Simulation Results

Figure 5B:
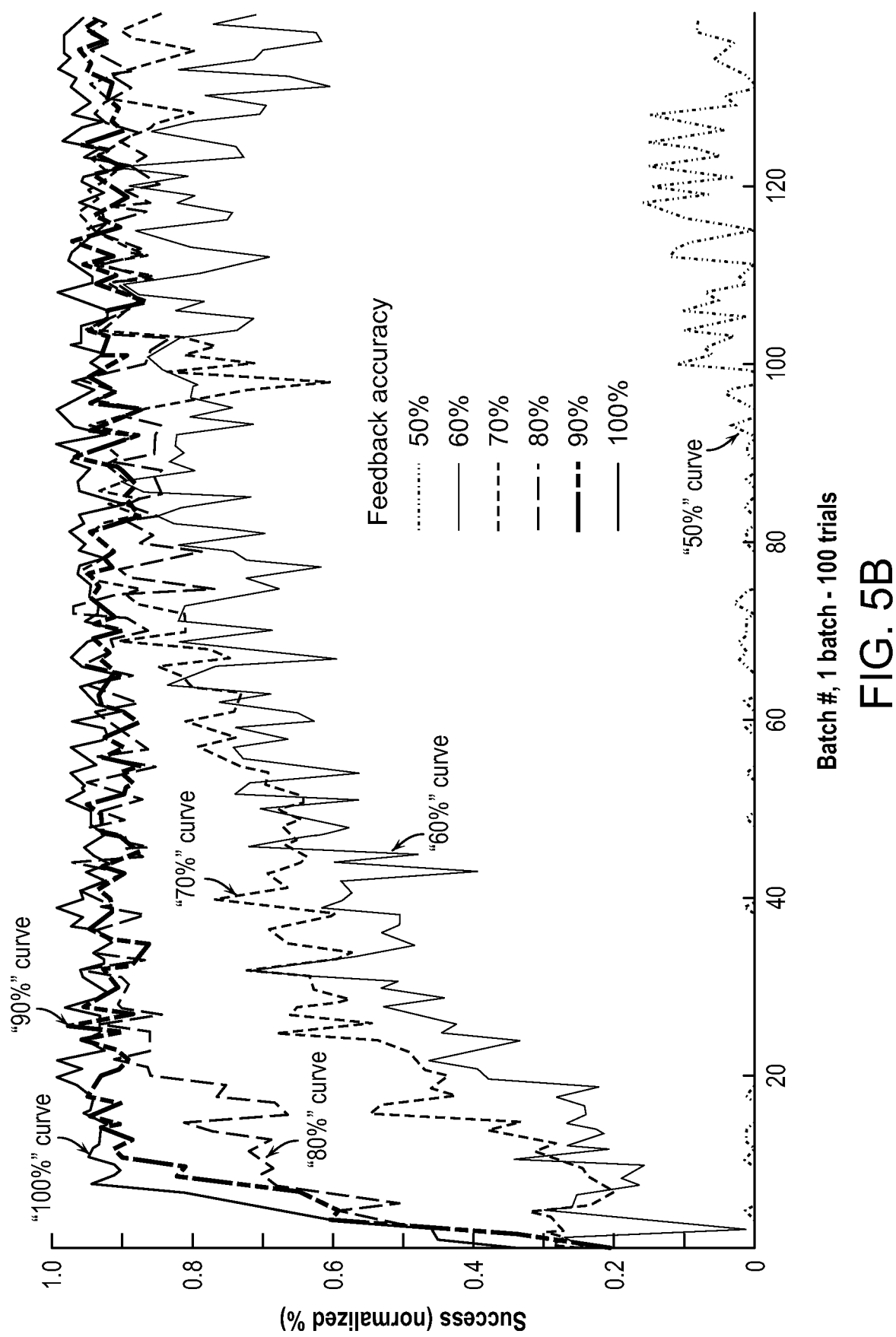
FIG. 5B illustrates the success rate of the RL agent vs. accuracy of the feedback in accordance with certain embodiments of the disclosed subject matter.

The maximum success rate achieved by our classifiers was about 75%, which means that the classifier would be providing the wrong feedback 25% of the time. Therefore, we wanted to test if such an accuracy rate was enough to train our RL decoder. Simulations were performed to ascertain the effect of the reward feedback accuracy on the RL agent's performance. A correct action, as stated in the methods section, in the normal scenario was awarded with +1 as the immediate reward whereas an incorrect action was awarded with −1. FIG. 5B illustrates success rate of the RL agent vs. accuracy of the feedback in accordance with certain embodiments of the disclosed subject matter. Several simulations were performed to quantify the effect of varying the accuracy level of reward feedback on the performance of the RL agent. In these simulations, the accuracy of the immediate reward provided to calculate the qualitative error signal used in adapting the RL agent through backpropagation was varied from 50% to 100% in intervals of 10%. Inaccurate immediate reward values were provided randomly. 50% accuracy meant that the correct value for the immediate reward, which corresponds to the action performed, was provided as feedback only 50% of the time. The RL agent was able to perform at a success rate of 80% and above for feedback accuracies of 60% and above as shown in FIG. 5B. Hence we claim that 75% success rate of our classifiers will be more than sufficient to train the RL decoder for a BMI system. It should be noted there are many ways one could improve the critic's performance and increase the actors performance beyond the levels presented here.

Discussion

According to some embodiments, disclosed is a method for producing a BMI that would, in theory, be autonomous such that it could update itself when necessary by sensing "things" are not working well for the user. The system utilizes neural activity from, for example, the rostral primary motor cortex, which is easily accessible for implantation with electrode arrays that have already been implanted in humans for BMI purposes. We have shown that activity in this region can be used not only for information on motor intent, but also for information on the reward expectation of the ongoing movement. We have also shown that it is possible to determine rewarding vs. non-rewarding movements on a moment-to-moment basis from the M1 population. That is that M1 is modulated by reward expectation. We subsequently showed that this critic like signal derived from the M1 activity is suitable for use in reinforcement learning based systems, something we have previously shown using hemodynamic signals as well. We have also seen that this reward modulation occurs in M1 even when the subject is passively viewing cursor trajectories. Our previous work has shown that such reward expectation information can be derived from the frontal brain regions of animals passively viewing cursor movements utilizing non-invasive systems. Clearly we can supplement the critic information gathered from the M1 array with these non-invasive measures and one can certainly see that RL based systems should have benefits for non-invasive BMIs, also called brain computer interfaces, as well as the invasive system we have presented here.

Advantages of RL-BMI Architectures

One of the clearest advantages to systems such as the one we have proposed is that there is no need for explicit training data as is the case for BMIs utilizing supervised learning methods. That is one does not need to have an exact quantitative error signal, such as the difference on a moment-to-moment basis between a real movement and an intended movement. Rather one can simply know if what the BMI is or is not doing was what the user expected or wanted, and this need not be on a moment-to-moment basis either. If the BMI is doing something unwanted this should lead to a negative output from the critic derived from the neural activity, and if something desired is occurring a positive output should be derived. As we are dealing with neural systems there is always uncertainty and noise, and thus one can threshold the outputs from the critic so that unnecessary updating of the actor does not occur. One can easily use methods developed under statistical hypothesis testing to provide a confidence measure to the critic's output.

Reinforcement learning based BMI system can learn from experience. It takes children over a year to learn how to walk, and it is possible that this is via RL-like learning. There are ways to speed up the learning process through mechanisms such as 'fitted Q learning' wherein one can iteratively replay the experienced data through the system with added noise and a slow learning rate. The additional noise reduces the chance of over fitting by the neural network and a slow learning rate helps keep the system stable and from diverging. It has also been shown that for simple RL-BMI systems fast convergence is possible. In addition, one can start off by training the weights of the BMI policy with a supervised approach and then when the individual is out in the real world utilize an RL based system such as the one we have proposed. One can continue to switch between supervised learning and RL to modify the actor in the actor-critic framework.

It has also been shown that RL-BMI systems can adapt when the neural environment changes, such as when one loses or gains single units on the electrode array that is feeding data into the BMI. These aspects make RL-BMIs very appealing and with an informative critic like signal derivable from the brain the system can work autonomously. Even in the case when the neurally decoded critic is faulty the user can give the system the correct input (see FIG. 1), as a simple binary feedback, that is the user will let the system know when it is wrong. This may be necessary when the critic is wrong; as if the actor is wrong the critic will update the system. The level of interplay between the user and the system can easily be tailored to the individuals liking. Implied in these statements is that the user would have information on the critics decisions, and would therefore know if the critic was faulty. Such simple binary feedback should be derivable from most users via speech, eye movements, tongue movements etc. As technologies move forward one can easily imagine the user simply identifying the goal of a reach to help recalibrate the system rather than having to give continues feedback to the critic. All of this may be necessary if the system is not performing to the user's acceptable level.

EXAMPLE 2

Methods

Surgery

Three bonnet macaques (*Macaca radiata*) (two male monkeys A and C, and one female monkey Z) were chronically implanted bilaterally in the primary motor cortex with, for example, 96 channel platinum microelectrode arrays (for example, 10×10 array separated by ~400 μm; in some embodiments, the microelectrode arrays used were from Blackrock Microsystems, Salt Lake City, Utah). The implantation of large numbers of electrodes has been described in Example 1 above. All procedures were conducted in compliance with the US NIH Guide for the Care and Use of Laboratory Animals and were approved by SUNY Downstate Medical Center IACUC.

Extracellular Unit Recordings

Unit activity was recorded using, for example, the Plexon Multichannel Acquisition Processors systems from MAPs, Plexon Inc., Dallas, Tex. Activity was sorted online before recording sessions using Sort Client provided by Plexon Inc. For data analysis, we used bilateral M1 units from Monkey A and C, and ipsilateral M1 units from Monkey Z for our manual experiments. In our observation experiments, we analyzed data from the contralateral M1 (with respect to the right arm) of Monkey A and the ipsilateral M1 (with respect to the right arm) of Monkey Z. For the purposes of this work we did not specifically segregate units between single and multi-units.

Electromyography

Surface gold disc electrodes (for example, from Grass Technologies) were sewn onto elastic bands and placed on the skin overlying muscle groups. EMG was recorded from the following muscle groups—latissimus dorsi, biceps, deltoid, triceps, forearm extensors, and forearm flexors. EMG signals were acquired through the Plexon system at a sampling rate of, for example, 2 KHz.

Experimental Setup and Behavioral Training

Figure 6A:
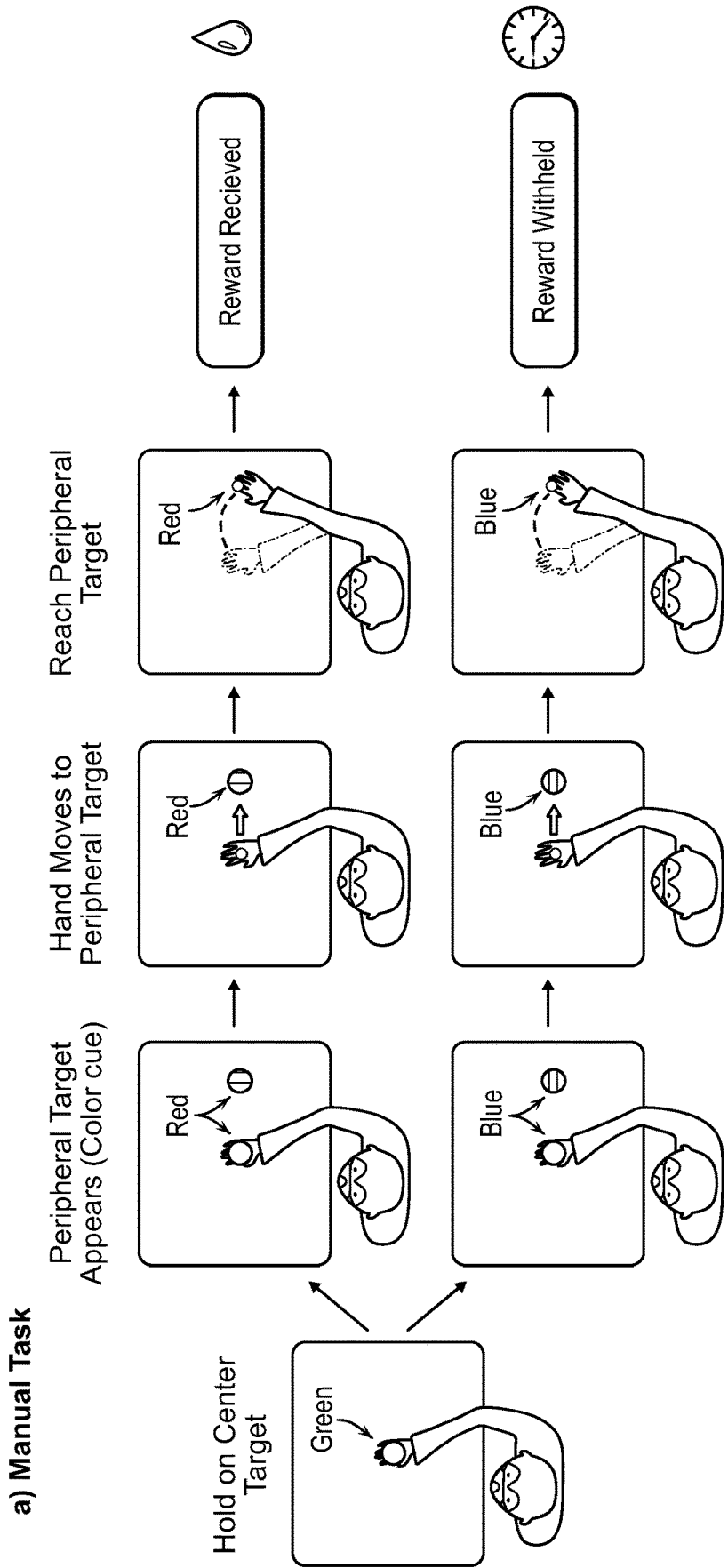
FIG. 6A illustrates a manual task in accordance with certain embodiments of the disclosed subject matter.

Macaques (1 female, 2 males) were trained to perform a center-out reaching task while their right arm rested inside, for example, the Kinarm exoskeletal robotic manipulandum ("KINARM") (BKIN Technologies, ON, Canada). There were two main types of experiments, manual and observational tasks. Visual feedback of the current hand position was provided by a cursor on the monitor that precisely co-located with the tip of the monkey's middle finger. FIG. 6A shows a manual task in accordance with certain embodiments of the disclosed subject matter. In FIG. 6A, the behavioral task consisted of right hand movements from a center target to a peripheral target located, for example, 5 cm (or other suitable distance) to the right. The target radius was 0.8 cm (or other suitable value). Trials were initiated by entering the center target (with neutral color) and holding for, for example 325 ms (center hold). In some embodiments, other suitable value can be used for the center hold. The center hold was followed by the color cue period. In some embodiments, the color cue period can range, for example, from 100 to 300 ms depending on the animals' temperament. The color cued peripheral target was displayed and the color of the center target changed from the neutral color to the same color as the cued peripheral target informing the monkey whether the trial would be rewarding or non-rewarding. The monkey was required to maintain its hold on the color cued center for a hold period. In some embodiments, this hold period can range from 325 to 400 ms, again depending on the animals' temperament. The implicit GO cue was when the center target disappeared after the color cue period (for example, 300 ms) at which time the monkey could move to the peripheral target, where it had to hold for the hold period (for example, 325 ms) before receiving a liquid reward or no reward. A liquid reward was provided only after a successful reach for a rewarding trial. If the monkey failed to complete a trial correctly, the same trial was repeated, giving incentive to perform non-rewarding trials correctly the first time. Trials types were randomized. In FIG. 6A, the drop symbolizes reward, and the clock symbolizes no reward, i.e. passage of time.

Figure 7A:
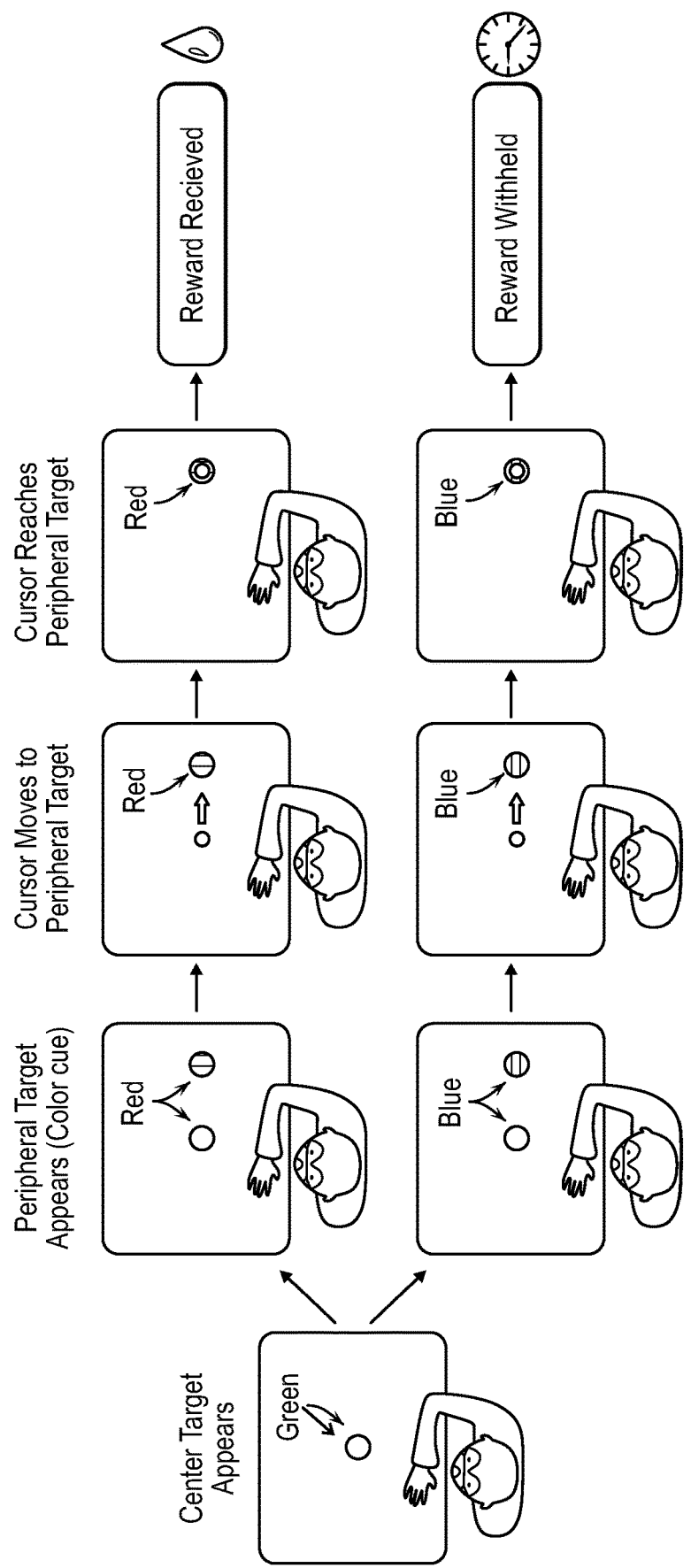
FIG. 7A illustrates a first observational task in accordance with certain embodiments of the disclosed subject matter.

FIG. 7A illustrates a first observational task (OT1) in accordance with certain embodiments of the subject matter. For OT1 as depicted in FIG. 7A, the rewarding and non-rewarding trials were color-coded as in the manual task, and the cursor would automatically move to the right hand "reaching" target while the KINARM was locked into place, so that the monkey could not make active reaching movements. However, the monkeys knew when the KINARM was locked and did not attempt to make reaching movements. For OT1 as depicted in FIG. 7A, the monkey would fixate at the center target and observe the center target change color, where red (the first row) corresponding to a rewarding trial, and blue (the second row) corresponding to a non-rewarding trial. The cursor would then move towards the peripheral target with movement towards a red target resulting in a reward, once the cursor arrives in the target, as indicated by the drop of liquid, likewise for blue targets reward was withheld as indicated by the clock. The monkey had to view the target plane to start a trial and maintain visual gaze until the color cue was given.

Figure 8A:
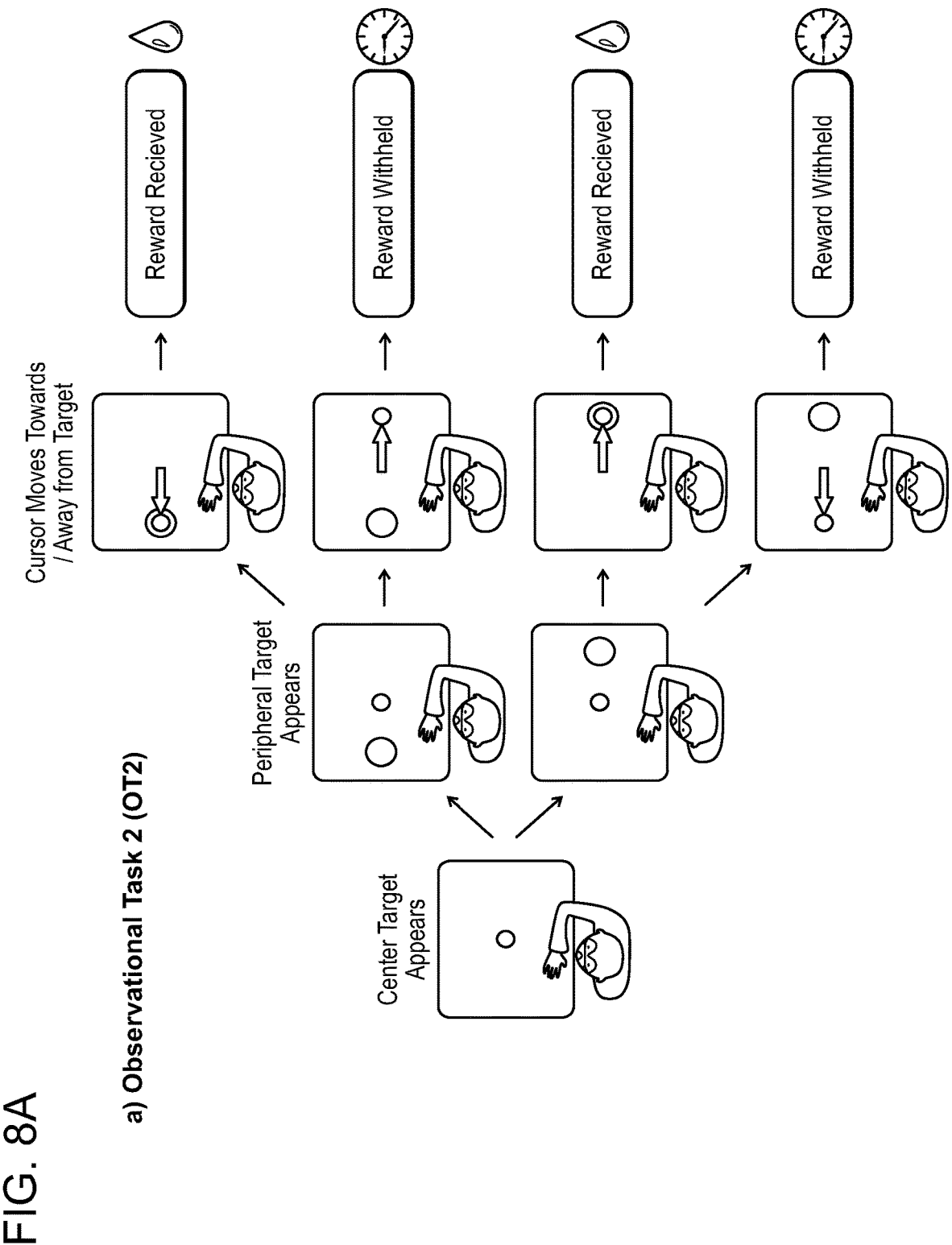
FIG. 8A illustrates a second observational task in accordance with certain embodiments of the disclosed subject matter.

FIG. 8A illustrates a second observational task (OT2) in accordance with certain embodiments of the subject matter. For OT2 as depicted in FIG. 8A, the color of the targets was maintained to be the same for rewarding and non-rewarding trials. The cue of reward vs. no reward was the cursor moving towards or away from a peripheral target, respectively. In this version of the task there were two possible peripheral targets, as can be seen in FIG. 8A. In FIG. 8A, the drop symbolizes reward and the clock symbolizes no reward, i.e. passage of time. During each trial, eye-tracking was conducted using an IR sensitive camera. A trial was aborted if the monkey failed to look at the screen during the color cue period. During select sessions, we recorded surface EMG recordings from proximal and distal muscle groups (see above the EMG section). During observation tasks, the monkey's right arm was locked in place by securing the Kinarm exoskeleton. The left arm was restrained with a padded cuff for all experiment types.

Data Analysis

Multivariate linear regression was performed on the neural firing rates (for example, 100 ms bins) to fit and predict shoulder and elbow positions acquired during the manual task (See Table 1 for fits and predictions). The mean of each 100 ms of position data was fit by 10 bins of neural data, corresponding to 1 second of causal information (See Table 1 for 150 fits and predictions). Multivariate linear regression was also performed on the neural data (100 ms bins) to fit and predict EMG of right latissimus dorsi and right biceps brachii acquired during manual task and OT1 (see Table 2 for fits and predictions).

TABLE 1

Fit and Prediction R values 860

| | Shoulder Angle | | Elbow Angle | |
|---|---|---|---|---|
| | Fit | Prediction | Fit | Prediction |
| Monkey A: | | | | |
| Contralateral M1 | 0.8131 | 0.7177 | 0.6167 | 0.3382 |
| Ipsilateral M1 | 0.8762 | 0.5047 | 0.9022 | 0.6175 |
| Monkey C: | | | | |
| Contralateral M1 | 0.7161 | 0.5966 | 0.6879 | 0.6304 |
| Ipsilateral M1 | 0.6215 | 0.3375 | 0.6913 | 0.4134 |
| Monkey Z: | | | | |
| Ipsilateral M1 | 0.6999 | 0.5577 | 0.6267 | 0.4325 |

Table 1 shows Displays Fit and Prediction R values of the multivariate linear regression performed on the raw neural data with respect to the shoulder and elbow angle.

TABLE 2

| EMG Channel | Right Latissimus Dorsi | Right Biceps Brachii |
|---|---|---|
| EMG Reward Data Manual: | | |
| Prediction R | 0.877 | 0.9371 |
| Fit R | 0.9894 | 0.9917 |
| EMG Reward Data OT1: | | |
| Prediction R | 0.0112 | 0.0023 |
| Fit R | 0.6698 | 0.6631 |

Table 2: EMG channels show that the muscle activity is correlated highly with the neural data for the manual task, but not for OT1. Table 2 displays Fit and Prediction R values of the multivariate linear regression performed on the raw neural data with respect to the right latissimus dorsi and right biceps brachii EMG of Monkey A.

The total number of units acquired in each task per brain area ranged from 31 to 214. For the manual task: Monkey A had 172 contralateral M1 units and 126 ipsilateral M1 units (total of 298 units). Monkey C had 89 contralateral M1 units and 100 ipsilateral M1 units (total 189 units). Monkey Z had 52 ipsilateral M1 units. Hence the total number of M1 units was 539. For observational task 1: Monkey A had 214 contralateral M1 units and Monkey Z had 51 ipsilateral M1 units. For observational task 2: Monkey A had 54 contralateral M1 units and Monkey Z had 51 ipsilateral M1 units. The amount of units available slowly decreased over time after implantation.

For the manual task, we pruned the data in the following manner to be sure that the differences between rewarding and non-rewarding trials were not due to differences in kinematics. Non-rewarded trials were pruned, so that only trials with maximum velocity, path length, and time to reward within one standard deviation of rewarding trials were selected. All the trials whose maximum velocity peak occurred at or after 1200 ms (qualitatively/visually selected) post the initiation of the trial were eliminated to remove trials with delayed reach time. Trials with double peaks in the velocity profile were also removed. Only neural data from pruned trials were selected for analysis. The separability between rewarding and non-rewarding trials was evident without pruning the data (data not shown). However, the data was pruned to show that the separability was not purely due to kinematic differences between the trials.

We analyzed the manual trials and observational tasks, comparing rewarding trials to non-rewarding trials. The observational tasks lasted longer compared to the manual tasks due to our choice of the cursor speed. In the manual task, for each trial, data (binned at 100 ms) starting 200 ms before the color cue and ended 1500 ms (includes 300 ms post average reach time to the target) after the presentation of the color cue whereas; in the observational task, for each trial, data (binned at 100 ms) starting 200 ms before the color cue and ending 2700 ms (includes 300 ms post reach time to the target) after the presentation of the color cue was considered. No statistical difference (2-sample t-test, $p<0.05$) between the neural data considered 200 ms before the color cue in a rewarding vs. non-rewarding trials was observed.

The square root transform was performed on all units' binned data in order to bring the values closer to a Gaussian distribution. Reward modulated units (units with a significantly different firing rate between rewarding and non-rewarding trials for a state in the trial: two-sample T-test ($p<0.05$)) were further separated based on whether their average firing rate was higher for rewarding or non-rewarding trials. Units from these groups were selected as samples for the figures.

Classifiers

PC analysis was performed on all the units of the pruned data for the manual files and all the completed trials in observational tasks. The neural data was z-scored before running the princomp function in Matlab. PC score values were separated into rewarding and (pruned, for the manual task) non-rewarding trials. Support vector machines, logistic regression and linear discriminant analysis (linear classify function of Matlab) were tested to obtain the best prediction of rewarding vs. non-rewarding trials by utilizing PC scores as inputs. The best results were obtained from the linear classify function in Matlab. The smallest amount of PC scores that gave the best prediction values were selected for use in the algorithm. The first 10 PC scores were used. For each monkey, we applied leave one out cross validation on its data to quantify the classification performance.

LFP Analysis

LFP signals were collected from 32 channels of the M1 array through the plexon system at a sampling rate of 2 k (filtered between 0.7 Hz and 8 KHz). Event related time frequency (ERTF) analysis was carried out. The average of the 32 channel LFP signal was filtered at frequencies centered from 1-128 Hz (in log space) using Gabor filters with a proportional filter bandwidth of 0.25 (bandwidth=0.25×the center frequency). For each frequency channel, the absolute value of the filtered amplitude was re-aligned to the start of each trial and then averaged across trials. Color represents changes in proportion with respect to the baseline (the mean value from 500 ms before the start of the trial to 0 ms which is the start of the trial).

Reinforcement Learning Based BMI

Briefly, the theory of 'reinforcement learning' indicates that an agent, such as an animal, or in the disclosed subject matter, the RL-BMI system, should act in a manner that leads to the most rewards while interacting with its environment. The term environment in the disclosed subject matter includes the neural activation patterns from M1, and the type of reinforcement learning architecture that we are considering here is termed actor critic, where the actor is the motor BMI and the critic is the evaluative feedback. The logic utilized by the actor to perform an action given a state, neural firing pattern, is called the policy. An action performed by the actor under a given policy leads it to a new state in the environment and the consequence of such an action is utilized as feedback to modify its behavior/policy, which is learning.

Temporal difference learning is a branch of reinforcement learning that allows moment-to-moment updating given a simple evaluative feedback signal, such as the one we are deriving from the discussed classifier. In some embodiments, we utilized Q learning. The state-action value, $Q\pi(s, a)$, is the expected return starting from state 's' given that the RL agent executes the action 'a' in state 's' under a policy $\pi$. In some embodiments, we used an $\varepsilon$-greedy policy as the actor and the Q learning paradigm augmented with Eligibility Trace $Q(\lambda)$, as the actor's update rule. An eligibility trace is extremely useful in dealing with the credit assignment problem. The action with the highest Q value is selected $1-\varepsilon$ percent of the time (exploitation) whereas a random action is performed $\varepsilon$ percent of the time (exploration) under the $\varepsilon$-greedy policy. Persons skilled in the art will appreciate that there are also other ways to change $\varepsilon$ given the systems performance.

In Q learning, the TD error equation is:

TD error: $r+\gamma^* \max_a Q(s',a')-Q(s,a)$ where; $r=\{-1, 1\}$ is the immediate reward, $\gamma$=the discount rate and its allowable range is [0,1], (s, a)=the previous state and the action performed in state s under an $\varepsilon$-greedy policy $\pi$ respectively, and (s', a')=the current state and a' is the $\varepsilon$-greedy action in state s' respectively. The TD error is used as feedback to update the estimates of the state-action values (Q values).

$Q(s',a')=Q(s,a)+\alpha^*TD\_error$

Where $\alpha$=learning rate.

In an embodiment of the architecture, r is the class label predicted by a reward classifier (critic) whose input is the M1 neural activity. Specifically, when population firing is classified as rewarding, r is set to 1, whereas when the neural activity is classified as non-rewarding, r is set to −1. As such, a classifier outputs a binary evaluative measure by decoding the neural signal, which critiques the executed action. The architecture suggested here conforms to a broader definition of the actor-critic architecture as it has a separate memory structure to explicitly represent the policy independent of the entity providing the evaluative signal. The scalar evaluative signal is the output of the critic and drives learning in the actor. The suggested architecture can easily be modified to conform to the stricter definition of actor-critic wherein, the critic represents the estimated value function and the evaluative feedback provided by the critic is utilized to update itself along with the actor. One can also envision versions where the user gives feedback on the critic's performance as a perfect source of feedback to update the critic and subsequently the actor when necessary.

Simulations

One of the future biomedical engineering goals is to use neural activity from M1 simultaneously to control movement, via a motor BMI, as well as to update this BMI via an evaluative feedback signal, also derived from M1. One architecture that is well suited for this type of updating would be a BMI that works via reinforcement learning, as this would only necessitate an evaluative signal, such as rewarding or non-rewarding, rather than a full error signal, such as the difference on a moment-to-moment basis between the desired movement trajectory and the actual one made by the BMI. This later full error signal is what most BMIs to date employ. This decrease in the amount of information necessary for updating the BMI system makes it more plausible that such a system could autonomously correct itself in real world changing environments. One can easily imagine combining the best of the supervised learning world with the best of the reinforcement-learning world. (See the below section for methods on the reinforcement learning agent.)

Here we simply wish to demonstrate that the amount of evaluative feedback obtained in our experiments from M1 would be sufficient for a reinforcement learning BMI in theory to work. Toward this goal we utilized a simulation of the motor cortical output that we have previously utilized in testing RL-BMI systems. We have previously used M1 information for BMI purposes, including RL-based systems and thus know that the movement related activation is present. We therefore needed to test if the evaluative feedback from M1 would be sufficient as well. In addition, the RL system we are going to utilize for our proof of concept is a simple one step system, meaning it utilizes the neural output from M1 at the start of the trial during target presentation that is only one time bin worth of M1 output, and from that neural activation pattern decides what target it will move to, therefore real time feedback from M1 for corrective movements is not being considered. This type of one step system has been shown previously in real-time. Our rational for using the simulation rather than the actual monkeys for this RL-BMI proof of concept is that the monkeys used for these reward based experiments had lost their chronic recordings to a large extent by time this work would have been conducted.

we used the classification rates obtained in OT2 for this simulation work as this was as close to BMI feedback as we would expect, that is, the evaluative feedback was simply based on whether the "hand feedback" cursor was moving toward or away from the rewarding target. Again, in a one-step task there would be no difference from the animal's point of view between this observational task (OT2) and an online RL-BMI. In Example 1, we have described the use of a reinforcement learning (RL) paradigm in which an RL agent performed a 4 target-8 action center out reaching task by decoding the firing rate of a simulated M1 neuronal ensemble. We utilized this same neural model here, and thus only briefly describe it. In this M1 model a group of neurons was simulated using the Izhikevich model neuron. The neural ensemble consisted of 80 neurons; 60% of the neurons had unimodal tuning curves, 15% were had bimodal tuning curves and 25% had assigned asymmetric tuning curve. A tuning curve directed the degree of neural modulation given the direction of the target with respect to the present cursor position, which was the start target. In some embodiments, directions of these neurons were assigned randomly. A spike was detected every time the membrane potential of a neuron surpassed 30 mV. The task was identical to OT2 in spatial arrangement and cursor motion; however, the cursor was controlled by the RL system.

The target direction in a given trial changed each neuron's firing rate with respect to its baseline activity based on their respective tuning curves. That is, given a target in the left direction, the neurons that had their preferred direction to the left fired at their maximum firing rate whereas the remaining neurons modulated their firing based on their tuning curve. Using the output of the simulated neural ensemble as the input to an artificial neural network the Q value for each potential action was determined. Specifically, a multilayer perceptron (MLP) with a single hidden layer consisting of 120 units was used to calculate the Q value given an input from the neural ensemble. 99% of the time the action with the highest Q value was executed (the "greedy" part of the ε-greedy policy), and the other 1% of the time a random action was taken (the exploratory rate, the 'ε' part of the ε-greedy policy). Exploratory rate, defined as the percentage of steps in which an action is executed randomly irrespective of its optimality at a given state, was set at 1% ('ε' part of ε-greedy policy). The random exploration allows for discovery of new solutions by the RL agent, useful especially in an altering environment. Update of the weights of MLP was performed by backpropagation of a qualitative error signal 'TD error*eligibility trace' calculated utilizing the immediate reward it received based on the correct or incorrect action performed. A correct action resulted in evaluative feedback to the RL agent of either +1 (rewarding) or −1 (non-rewarding) with a probability determined by the success rate of our M1 classifier for OT2, which was 70% correct feedback. This means that 70% of the time in our simulation the RL agent was given the correct evaluative feedback of rewarding or non-rewarding and 30% of the time it was given false information.

Results

Reward Expectation During Reaching Modulates Units in M1

In our first set of experiments, we recorded single and multiple unit activity bilaterally from M1 in 3 bonnet macaques while they performed a reaching task from a center target to a right peripheral target (FIG. 6A) while wearing an exoskeletal robot (for example, from BKIN Technologies, ON, Canada), not shown. In what follows we did not differentiate between single and multi-units unless otherwise explicitly stated. To investigate neural correlates of reward expectation, we trained the subjects to perform the task with knowledge of whether a reward would be provided at the end of a successful trial by color coding the targets on the screen: for example red for rewarding and blue for non-rewarding (FIG. 6A). In some embodiments, rewarding trials occurred 50%-67% of the time, based on the monkey's motivational level, and the trials were randomized within each recording session. We selected kinematically indistinguishable trajectories between the two reward contingencies for offline analysis to isolate the effect of reward (see methods for details). We discovered single units in M1 whose firing rates modulated with respect to reward expectation.

Figure 6B:
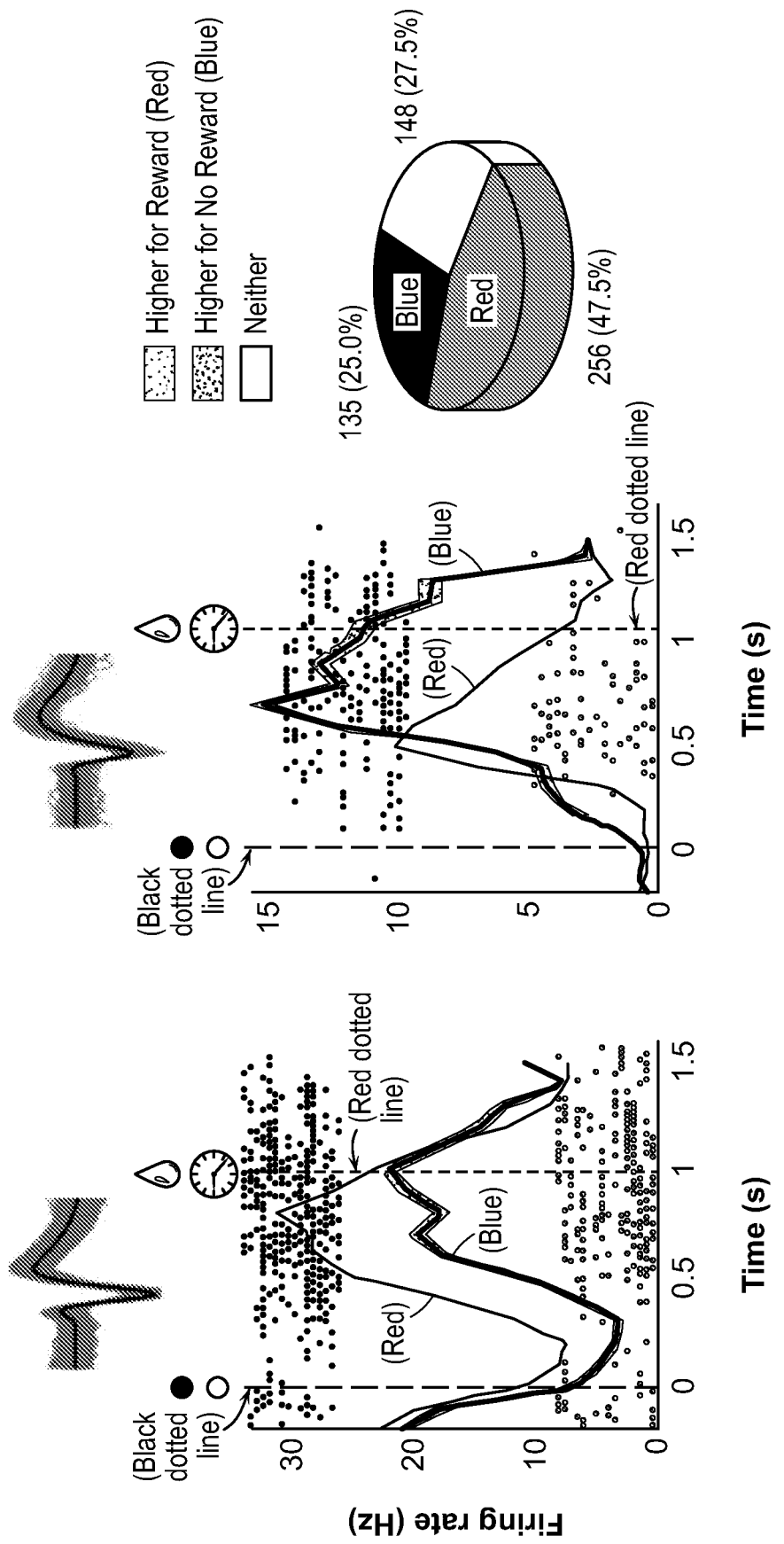
FIG. 6B illustrates modulation of M1 units by reward expectation in the manual task in accordance with certain embodiments of the disclosed subject matter.

FIG. 6B shows modulation of M1 unit responses in the manual task in accordance with certain embodiments of the disclosed subject matter. Responses for each trial were aligned at the color cue onset (black vertical dashed line) and were separated by trial type (red for rewarding and blue for non-rewarding). A difference in the firing pattern was observed for data considered post color cue and before reward/no reward was acquired (red vertical dashed line). The average firing rate of the left example unit was higher during rewarding trials whereas the right sample unit had a higher firing rate during non-rewarding trials (t-test, p<0.05). Note that in the left example unit the activity is qualitatively very similar between the trial types, but simply shifted upward for rewarding trials. In total, 73.6% (192 out of 261) contralateral M1 units and 47.8% (133 out of 278) ipsilateral M1 units were reward modulated. The pie graph in FIG. 6B displays the total percent of M1 units that had higher firing rates during rewarding, non-rewarding trials, or neither: combining contralateral and ipsilateral M1 data, 47.5% (256 out of 539) of M1 units had average firing rates higher during rewarding trials than non-rewarding trials and 25.0% (135 out of 539) of M1 units responded in the converse manner, with average firing rates higher during non-rewarding trials than rewarding trials. When the color of the rewarding cue was switched as a control, there was no significant difference in the neural representation of reward (data not shown).

Reward Expectation During Observation Tasks Modulates Units in M1

In order to incorporate these results into a BMI, we needed to know if reward modulation would also be measureable in the absence of an actual arm movement. We designed two experiments in which reward was distributed conditionally upon passive observation of a moving cursor on a computer screen while the macaques' arms were kept stationary. During the first observation task (OT1), a cursor moved from a center position to a peripheral target at a constant speed of, for example, 1 cm/s. The same target color cues used previously in the manual-reaching task above for no-reward and reward were presented at motion onset (FIG. 7A).

Figure 7B:
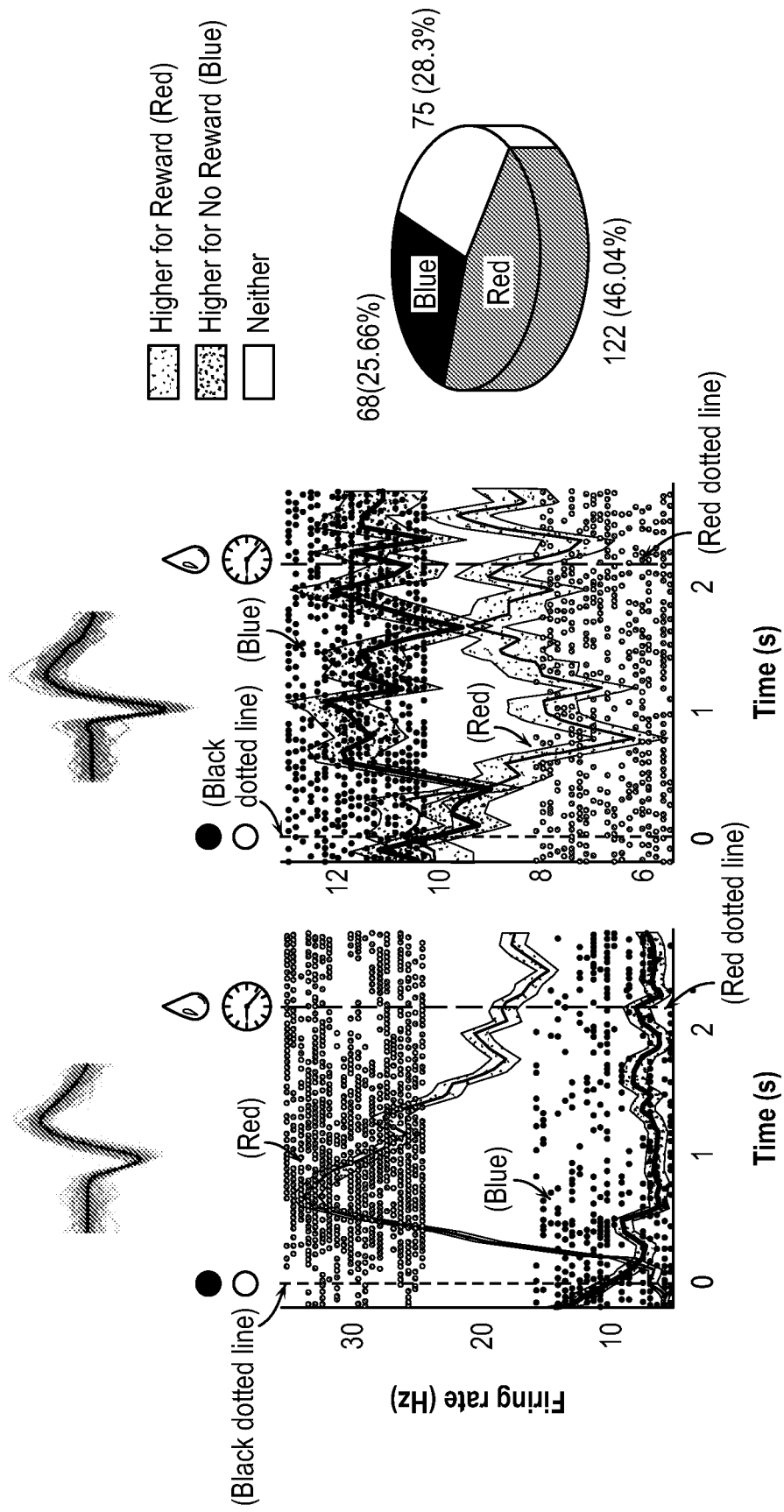
FIG. 7B illustrates modulation of M1 units by reward expectation in the first observational task in accordance with certain embodiments of the disclosed subject matter.

FIG. 7B shows modulation of M1 unit responses in the first observational task in accordance with certain embodiments of the disclosed subject matter. In FIG. 7B, the left graph displays a unit with a higher firing rate during rewarding trials. The right graph displays a unit with a higher firing rate during non-rewarding trials. For each sample unit, the average of all waveforms (in black) with sample waveforms in gray is shown above the peri-event rasters. We have plotted the average firing rate with SEM (shaded region following the curves) for rewarding (red) and non-rewarding (blue) trials, and corresponding sample rasters. The black dotted line corresponds to the time of color cue and the red dotted line corresponds to the time of reward. The pie graph displays the total percent of M1 units that had higher firing rates during rewarding, non-rewarding trials, or neither. The results indicate that a subset of neurons in the M1 population is modulated by reward expectation in the absence of arm movement or muscle activation (FIG. 7B). We found that 46.0% (122 out of 265) of M1 units had an average firing rate higher during rewarding trials than non-rewarding trials and 25.7% (68 out of 265) of M1 units had the opposite response (FIG. 7B). Note the diverse set of neural responses obtained as the left example unit in FIG. 7B demonstrated a large increase in activity for rewarding trials early, which then fell back toward baseline over the trial, whereas the right hand example unit showed tonic shifts in activity during the trial. Thus M1 neural activity is modulated by reward expectation when a contextual cue is given that indicates reward i.e. a color cue. Creating an experiment where kinematic parameters were identical was necessary in order to prove reward modulation in M1. However, there is generally no color cue in real-world BMI situations. Reward in real-world BMIs may be represented through a variety of explicit and circumstantial means including those related to successful operation of the BMI. An M1 reward signal, if present under these circumstances, is a natural candidate for providing reward feedback to reinforcement learning BMIs.

To explore this possibility, we designed a second observation task (OT2) in which the macaques observed a cursor that either moved towards or away from a neutral color target. The cursor movement was deterministic and always moved directly from the center start position either toward or away from the peripheral target. Reward was delivered on trials in which the cursor reached the target, but was withheld on trials in which the cursor moved away from the target (FIG. 8A).

Figure 8B:
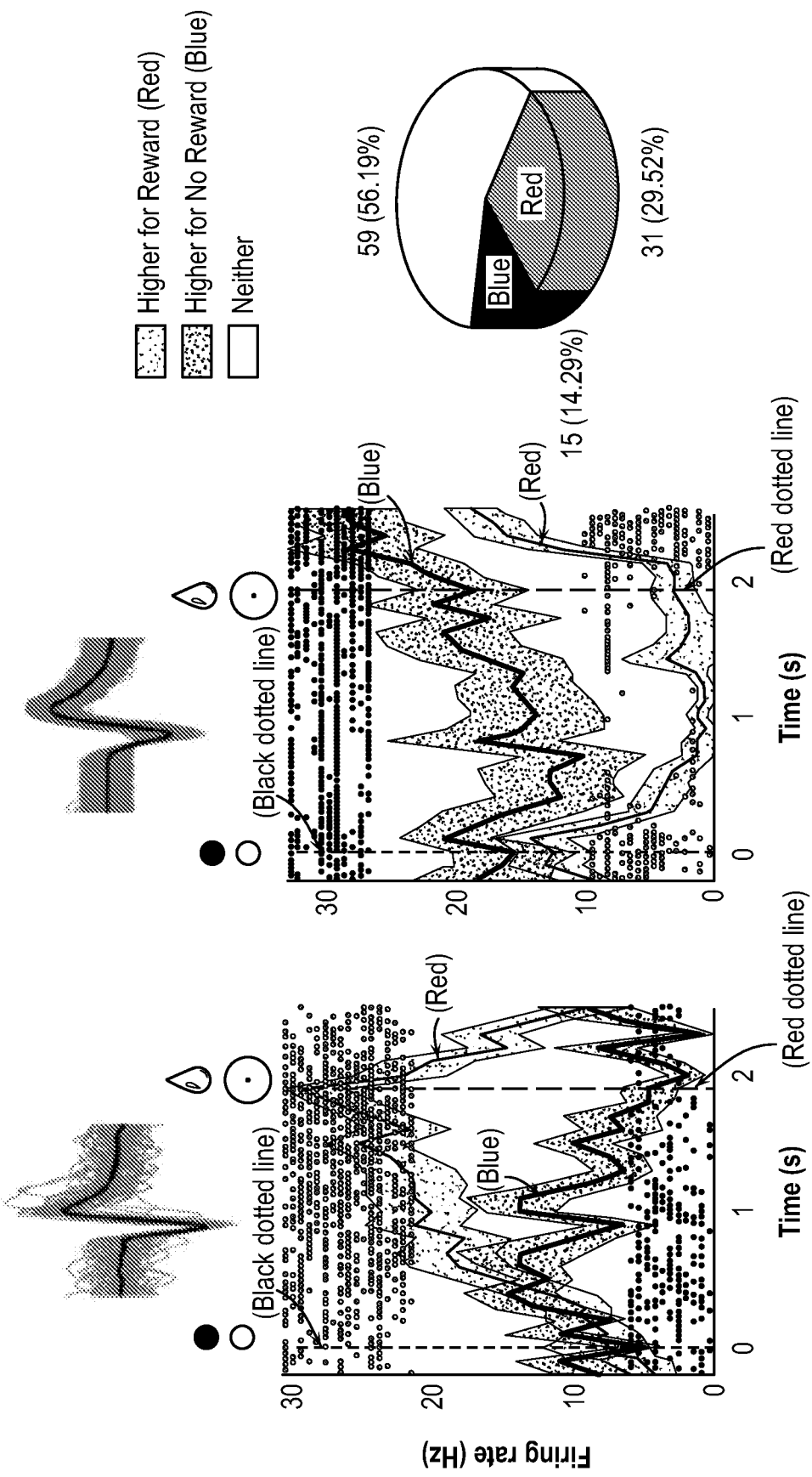
FIG. 8B illustrates modulation of M1 units by reward expectation in the second observational task in accordance with certain embodiments of the disclosed subject matter.

FIG. 8B shows modulation of M1 unit responses in the manual task in accordance with certain embodiments of the disclosed subject matter. In FIG. 8B, the left graph displays a unit that had a higher firing rate during rewarding trials. The right graph displays a unit that had a higher firing rate during non-rewarding trials. For each sample unit, the average of all waveforms (in black) with sample waveforms in gray is shown above the peri-event rasters. We have plotted the average firing rate with SEM (shaded region following the curves) for rewarding (red) and non-rewarding (blue) trials, and corresponding sample rasters. The pie graph displays the total percent of M1 units that fired higher during rewarding, non-rewarding, or neither trial type. Black dotted line corresponds to the time of the go cue. The black dotted line corresponds to the time of color cue and the red dotted line corresponds to time of reward. Again we found a population of M1 units that was modulated by reward expectation (FIG. 8B). We found 29.5% (31 out of 105) of M1 units had higher average firing rates during rewarding trials and 14.3% (16 out of 105) of M1 units had the opposite pattern, that is higher average firing rates during non-rewarding trials (FIG. 8B).

To further probe reward's influence on M1, we analyzed both contralateral and ipsilateral cortices across the above three tasks. FIGS. 9A-9I show example results for Monkey A contralateral M1 and FIGS. 9J-9R show example results for Monkey Z ipsilateral M1 in accordance with certain embodiments of the disclosed subject matter. In FIG. 9, the left column (FIGS. 9A-9C and FIGS. 9J-9L) shows the average correlation coefficient of firing rate to kinematic variables (position and speed) and 'reward' variable. The bar value and error bar represent the mean and SEM of the significant correlations (p<0.05), respectively. Percentages of significant correlated units are displayed above the bars. Middle columns (FIGS. 9D-9F and FIGS. 9M-9O) show the population 'neurograms' for rewarding and non-rewarding trials. The units were sorted according to the correlation coefficients with the variable 'reward' in descending order. The spike times of each unit were binned at 50 ms for manual and passive tasks and smoothened with a moving average of 10 bins. The average firing rate for each unit was then linearly normalized to the range between 0 (blue) and 1 (red). Right columns (FIGS. 9G-9I and FIGS. 9P-9R) show the average activity of the top 10 and bottom 10 units in the neurogram. The black dotted lines (the left dotted lines) correspond to the time of color cue and the red dotted line (the right dotted lines) corresponds to the average time of reward for manual and the actual time of reward for the OT tasks.

We first tested independently the correlation between the firing rate and the kinematic properties or reward expectation for each unit. To do this, we concatenated all trials within a task and computed the correlation coefficient of binned (50 ms) spike rate against each of three variables: position, speed (for manual task only), and reward. Position refers to either the hand feedback cursor position during manual tasks or to the viewed position of the cursor during observational tasks. We did not consider speed for our correlation analysis during the observation tasks because the cursor speed was designed to be a constant. Reward was assigned a value of −1 for non-rewarding trials and +1 for rewarding trials for all sample points within that trial. Mean correlation values for units can be found in FIGS. 9A-9C and FIGS. 9J-9L.

Figure 9A:
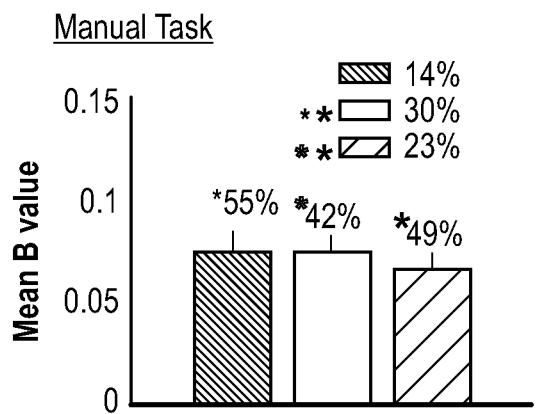
FIGS. 9A-9R illustrate contralateral and ipsilateral M1 reward modulation in accordance with certain embodiments of the disclosed subject matter.
Figure 9B:
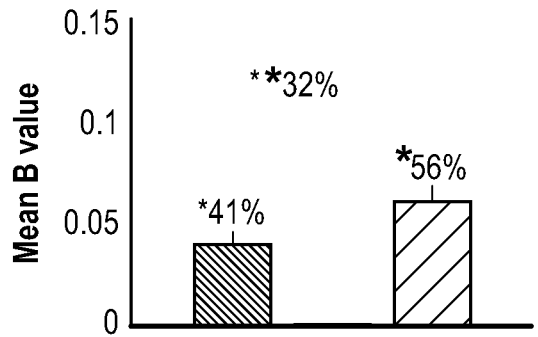
Figure 9C:
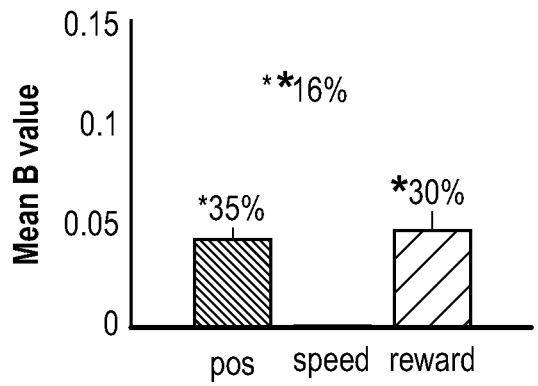
Figure 9D:
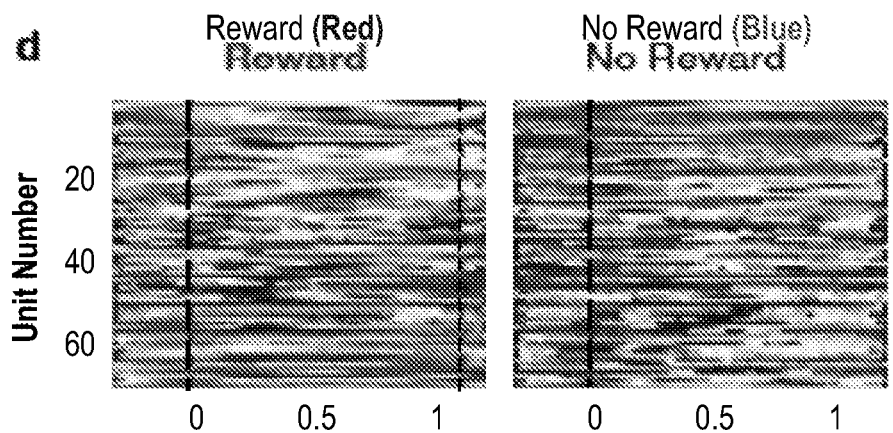
Figure 9E:
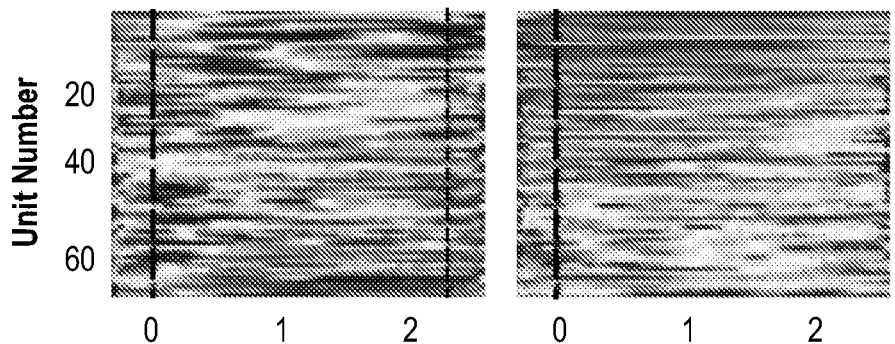
Figure 9F:
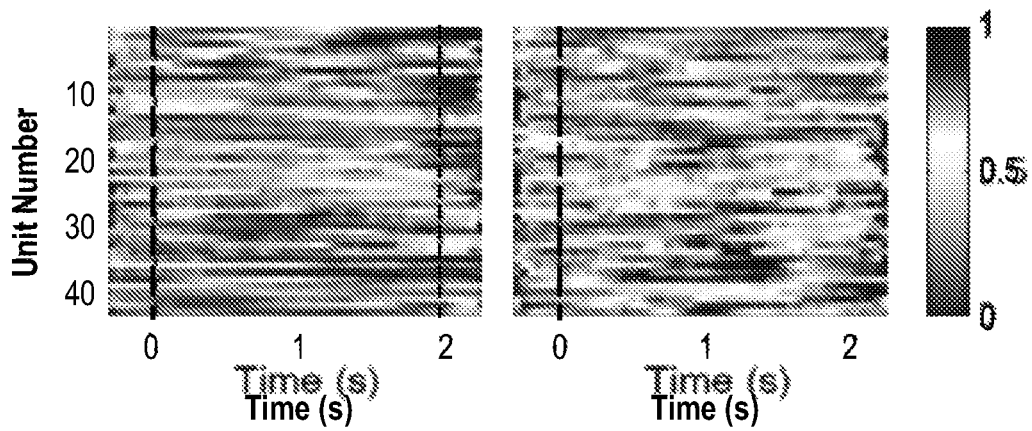
Figure 9G:
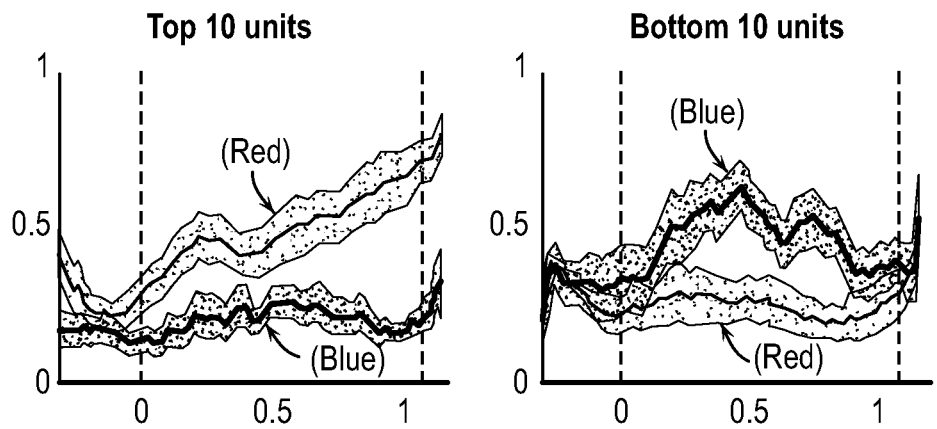
Figure 9H:
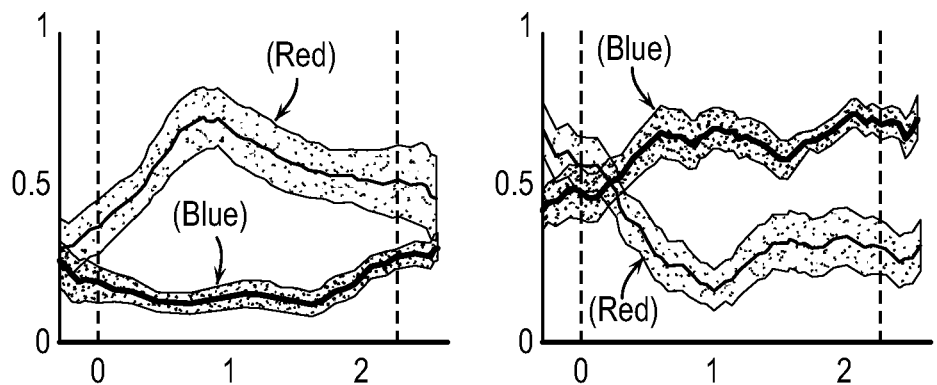
Figure 9I:
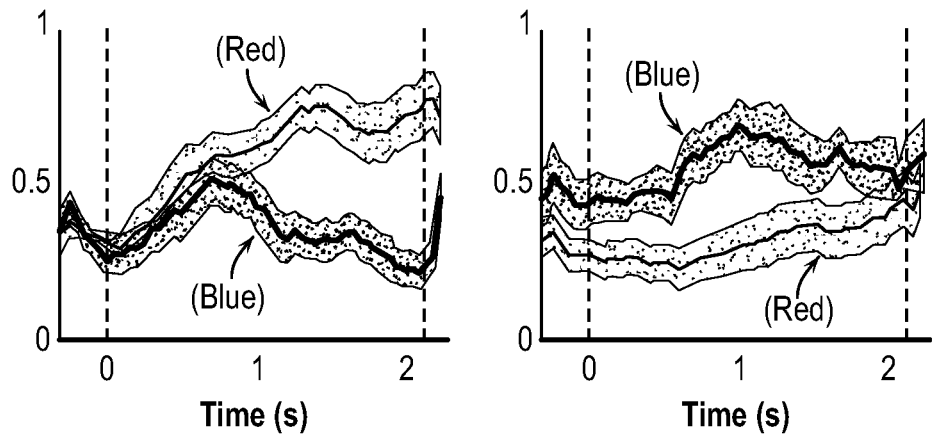
Figure 9J:
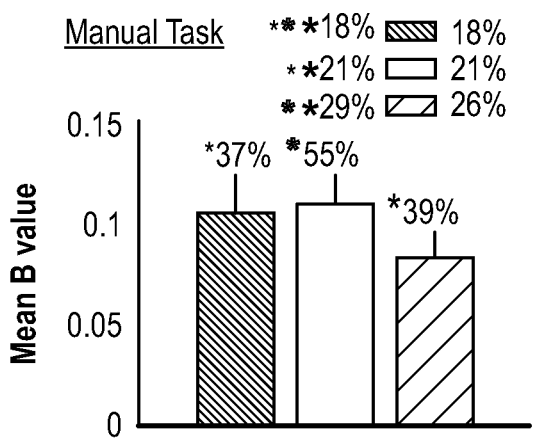
Figure 9K:
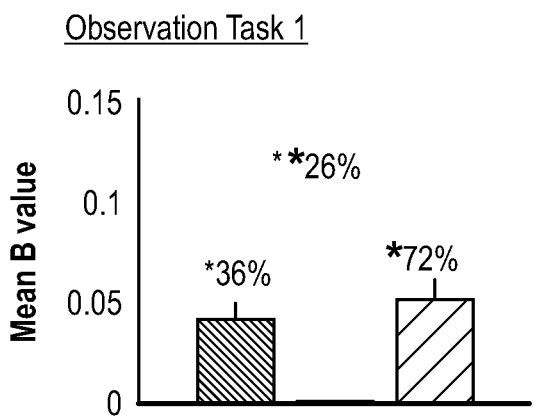
Figure 9L:
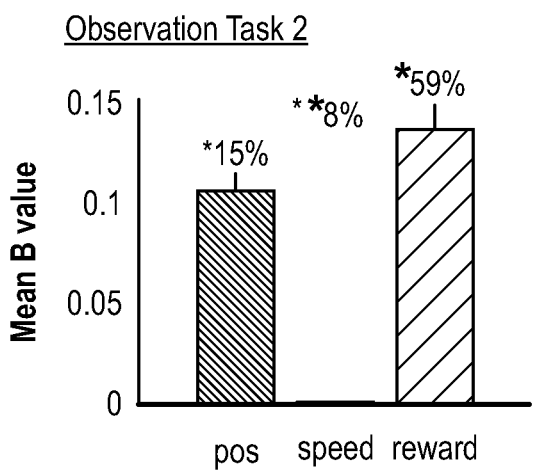
Figure 9M:
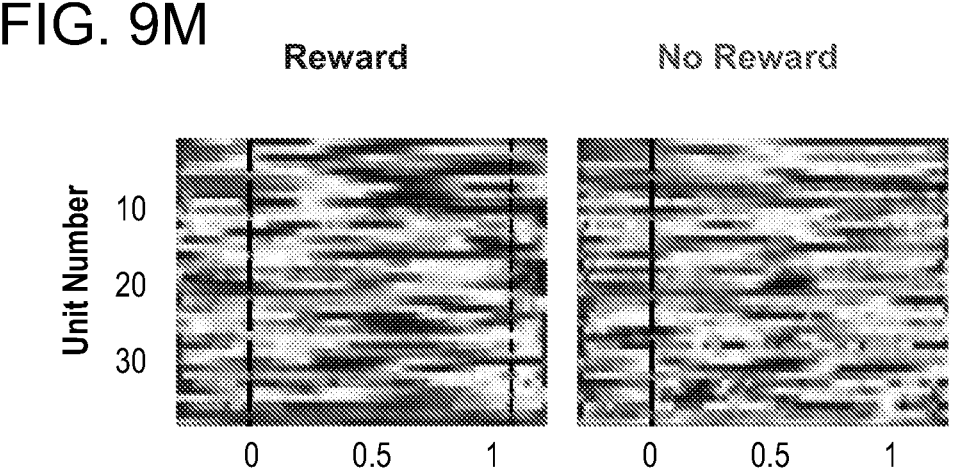
Figure 9N:
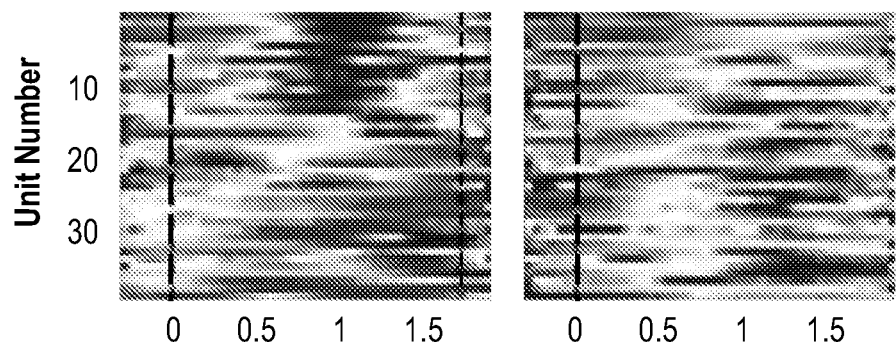
Figure 9O:
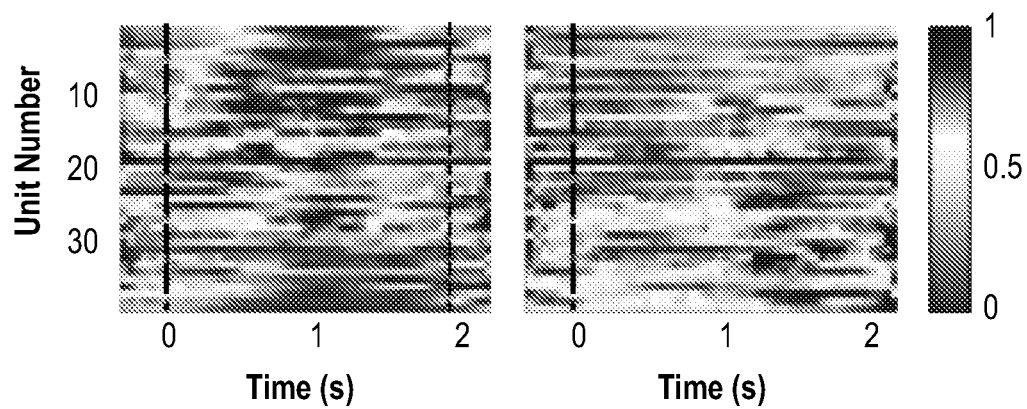
Figure 9P:
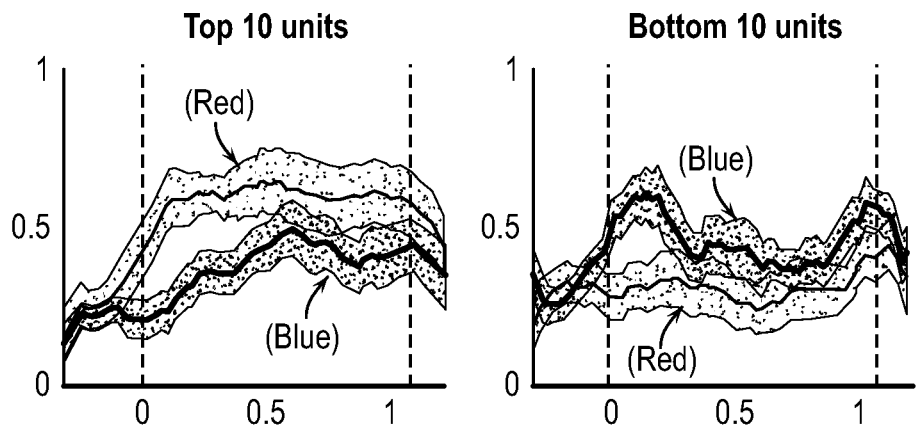
Figure 9Q:
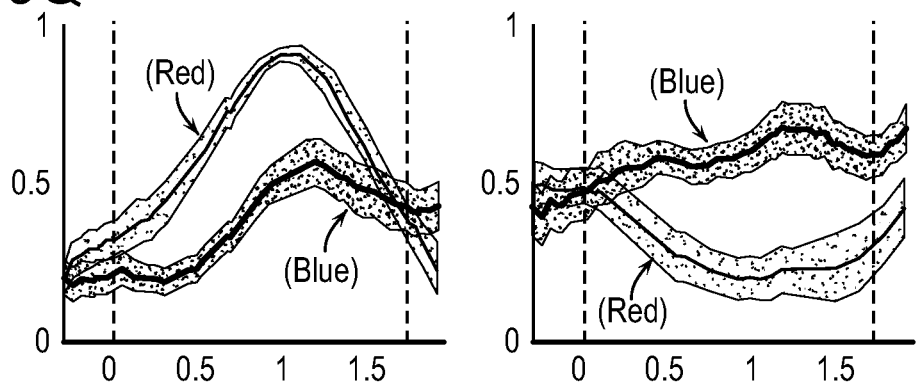
Figure 9R:
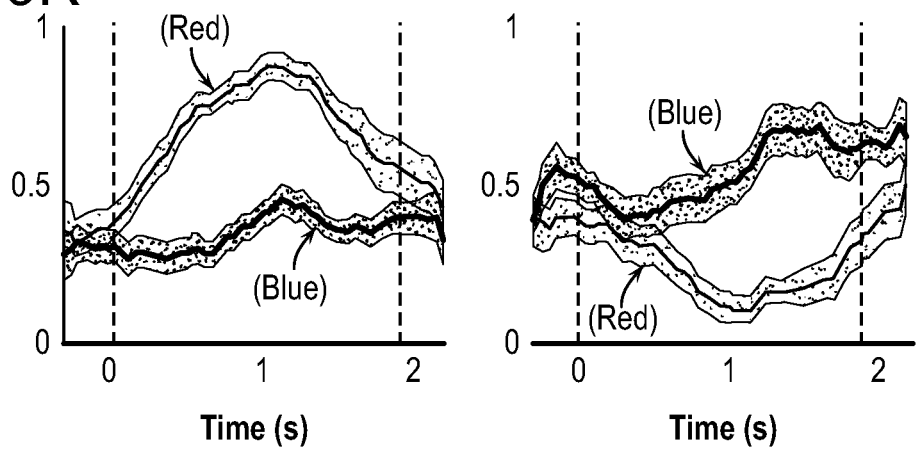

For the manual task, we found that 55% of contralateral and 37% of ipsilateral units were significantly correlated with position (FIGS. 9A and 9J, black bars (the leftmost bars) for mean correlation values and black asterisks for significant correlations (Pearson's correlation test, p<0.05)), while 42% of contralateral and 55% of ipsilateral units were significantly correlated with speed (FIGS. 9A and 9J, gray bars (the middle bars) and asterisks). Correlation was found in both cortices with respect to reward: 49% of contralateral and 39% of ipsilateral units were significantly correlated with reward (FIGS. 9A and 9J, red bars (the rightmost bars) and red asterisks). Furthermore, 30% of contralateral units were correlated with position and reward (FIG. 9A, black and red double-asterisk), 23% with both speed and reward (gray and red double-asterisk), and 14% with all three variables (triple-asterisk). Compared to the manual task there was a larger percentage of units correlated with reward during observation task 1 for both contralateral (66%, FIG. 9B) and ipsilateral (72%, FIG. 9K) M1 units as compared to the manual task. A subset of units was also correlated with cursor position (41% for contralateral and 36% for ipsilateral). To our knowledge this is the first report of reward modulated neurons in M1 to both action and action observation.

We next explored the population neural response difference between rewarding and non-rewarding trials using population neurograms, which show the average firing rate over time for all units (FIGS. 9D-9F and FIGS. 9M-9O). The units were sorted by the strength of their correlation to reward in descending order. The average firing rate for each unit was linearly normalized across the two trial types to the range between 0 (minimum firing rate, blue) and 1 (maximum firing rate, red). In all three tasks, we observed a difference in firing rate profiles between rewarding and non-rewarding trials (FIGS. 9D-9F and FIGS. 9M-9O). The average activity of the top 10 and bottom 10 units are shown to the right (FIGS. 9G-9I and FIGS. 9P-9R, red for rewarding trials and blue for non-rewarding trials). Note that often the peak activity (FIGS. 9H, 9P, 9Q, and 9R) is during the trial and not at the end as might be expected if actual reward delivery and consumption were causing the increased firing rates. The average firing rate pattern separates after cue onset (color cue for manual task, cursor movement onset for observation tasks). In summary, both contralateral and ipsilateral M1 contain units that simultaneously code for reward and kinematics during reaching and observation.

M1 Reward Modulation can be Used for Classifying Reward Expectation

Given the significant percentage of reward-modulated units, we examined the ability to classify the trial type on a moment-to-moment basis as would be beneficial for a temporal difference reinforcement learning BMI. Our results indicated that the first few principal component scores generated from the neural data (see methods section) were differentially separable based on reward (data not shown). We then used select principal component scores to create a reward classifier. Since BMIs are often designed to take in neural data every 100 ms, we separated the principal component scores along the same temporal resolution. Select principal component scores were used as the input into a linear classifier (see methods section).

Figure 10A:
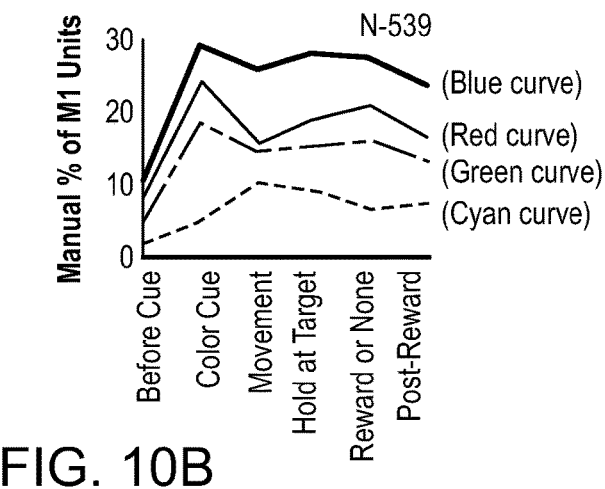
FIGS. 10A-10F illustrate state dependence of reward-modulation and classifier performance in the manual task, the first observational task, and the second observational task in accordance with certain embodiments of the disclosed subject matter.
Figure 10D:
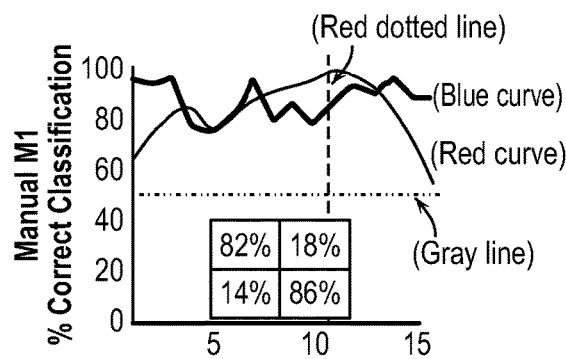
Figure 10B:
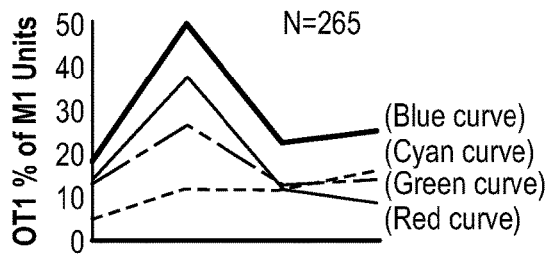
Figure 10E:
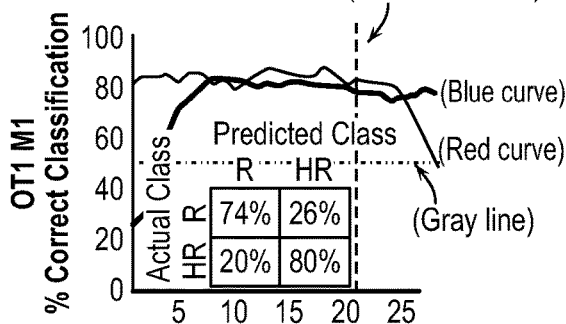
Figure 10C:
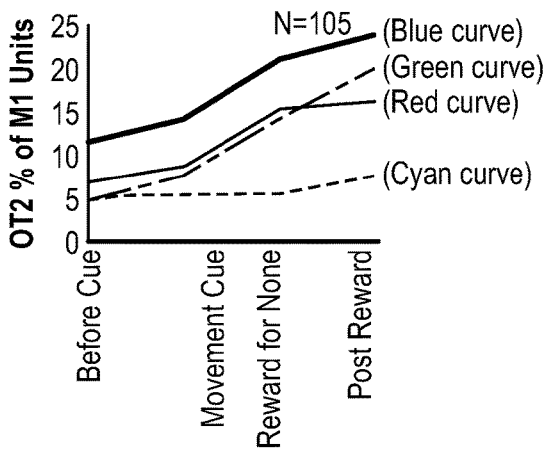
Figure 10F:
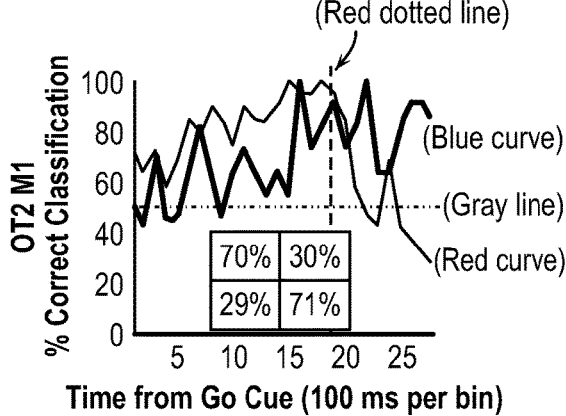

FIGS. 10A-10F illustrate state dependence of reward modulation and classifier performance in the manual task, the first observational task, and the second observational task in accordance with certain embodiments of the disclosed subject matter. Specifically, FIGS. 10A-10C illustrate state dependence of reward modulation in the manual task, OT1, and OT2, respectively. The percentage of reward-modulated units through different states in the trial is shown in BLUE. Percentage of units that fired higher during rewarding trials than during non-rewarding trials in a given state is shown in RED. Percentage of units that fired lower during rewarding trials than during non-rewarding trials in a given state is shown in CYAN. The percentage of reward modulated units that fired significantly higher during movement than during the color cue hold period is shown in GREEN. N equals the total number of units for each brain region. Two-sample T-test (p<0.05) on square-root transformed neural vectors for rewarding vs. non-rewarding trials and color cue vs. movement periods. FIGS. 10D-10F illustrate samples of linear classifier performance using leave-one out analysis. Graphs display the linear classifier performance for the subjects using select principal component scores from the contralateral M1 of Monkey A while he performed the manual task (FIG. 10D), from the contralateral M1 of Monkey A while he performed observation task 1 (FIG. 10E), and from the ipsilateral M1 of Monkey Z while she performed observation task 2 (FIG. 10F). RED lines represent true positives and BLUE lines represent true negatives. The inset tables display the confusion matrices for the sample results. The time of color cue is zero on the x-axis. The red dotted line corresponds to time of reward. Empirical chance is 50% (gray line).

The percentage of M1 units displaying reward modulation with respect to different states in a given trial is shown in FIGS. 10A-10C. The average classifier performance over all the M1 data for the manual task was 73.1% correct classification contralaterally and 69.0% correct ipsilaterally. The best M1 classifier performance was 82% true positives and 86% true negatives (FIG. 10D. Here, the optimal time point for classification was 1.2 s into the task, which yielded 94.3% correct classification.

The average classifier performance over all the M1 data for OT1 was 73.5% correct classification. In the OT1 task, the best classifier performance was 74% true positives and 80% true negatives (FIG. 10E). Here, the optimal time point for classification was 1.3 s into the task, which yielded 84.1% correct classification. For OT1, the M1 classifier showed a steep improvement between the color cue and 700 ms into the observed cursor movement (FIGS. 10B and 10E). Classifier performance was maintained at ~80% for rewarding and non-rewarding trials until 2.4 seconds into the trial (end of reward acquisition, FIG. 10E). For OT2, the classifier yielded 63.9% correct classification on average, showing improvement in performance as trial time increased (FIG. 10F). Note that we had fewer units for OT2 as it was conducted last in our set of experiments after manual and then OT1. For OT2, the best classifier performance was 70% true positives and 71% true negatives (FIG. 10F). Here, the optimal time point for classification was 1.6 s into the task, which yielded 97.4% correct classification. It should be noted that all these classification rates are on the moment-to-moment 100 ms bins that could be used for a temporal difference reinforcement learning method. However, higher classification rates should be expected if one takes into consideration the full trial time.

Local Field Potential Indications of Reward in M1

Figure 11:
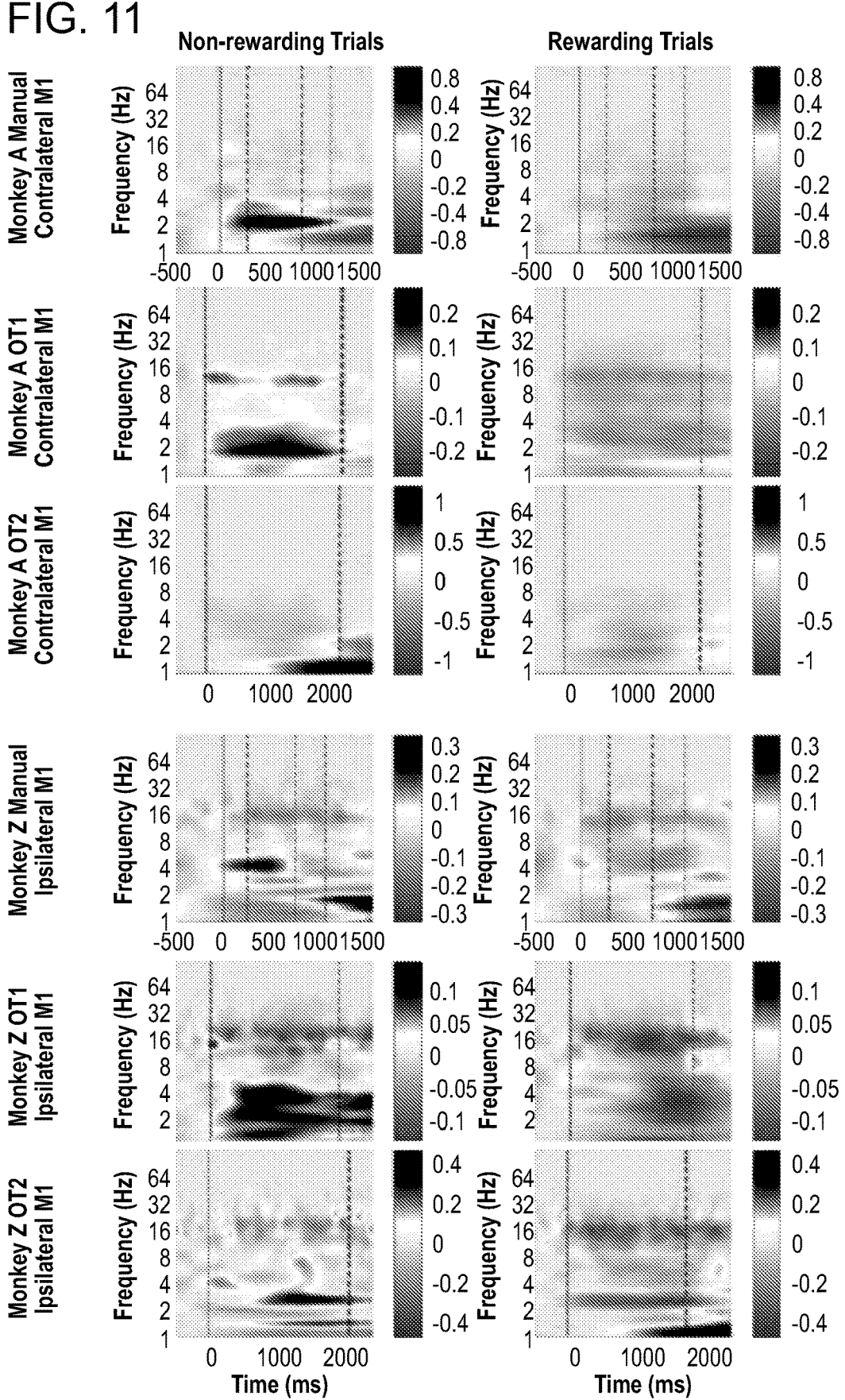
FIG. 11 illustrates local field potential modulation by reward expectation in accordance with certain embodiments of the disclosed subject matter.

We wished to see if the reward modulation would be evident in the local field potentials of M1 as well. Using experimental data from the manual center-out reaching task, observation task 1 (OT1), and observation task 2 (OT2), we examined the event-related time frequency components of the LFPs in M1 using a method similar to that described in (see Methods), in which we averaged all of the LFP channels together making a proxy for a larger EEG like electrode recording. FIG. 11 illustrates local field potential modulation by reward expectation in accordance with certain embodiments of the disclosed subject matter. In FIG. 11, left column corresponds to non-rewarding trials; right column corresponds to rewarding trials. Color scale represents proportional change of filtered LFP values relative to baseline (−500-0 ms) at each time for each frequency. Solid black line represents start of trial (cursor enters center target). First dash line represents start of cursor movement; second dash line represents end of cursor movement; and red solid line represents time of reward/reward withheld.

The results demonstrate a consistent event related increase for non-rewarding trials and decrease for rewarding trials in the delta and theta range (~1-8 Hz) in all three tasks for both contralateral and ipsilateral cortices (FIG. 11, from the same recording sessions as in FIG. 9). There were also event related changes in the beta range (~10-30 Hz) but less consistent between the two hemispheres/animals. The results are consistent with a study showing that dopamine depletion in the rat striatum amplifies LFP oscillations at delta and theta frequencies during movement. The results are also consistent with a study showing that dopamine depletion in both the striatum and primary motor cortex of dopamine transporter knockout mice causes an increase in the power of LFP oscillations at beta and delta frequencies in both brain regions. Hence, this analysis demonstrates a possible relationship between dopamine, reward expectation, and M1 LFPs. Further direct experimentation and recording will be necessary to determine if these LFP results are due to changes in dopamine, but clearly they indicate usefulness of LFPs for our desired BMI critic information, that is a signal that could tell us if "things" are going well or not, such as leading toward reward or not.

Simulated RL-BMI

Figure 12A:
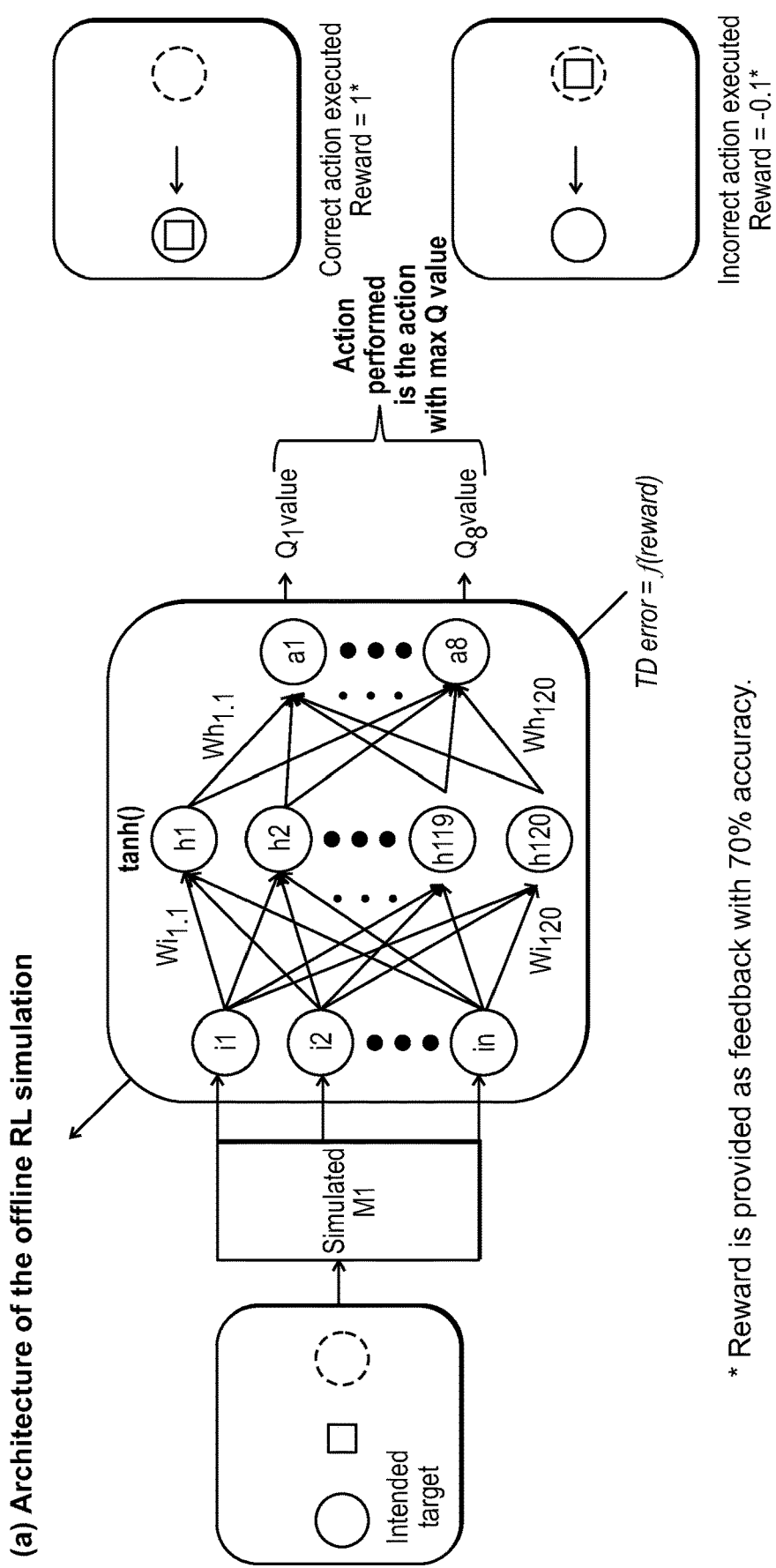
FIG. 12A illustrates an architecture of the offline RL simulation in accordance with certain embodiments of the disclosed subject matter.
Figure 12B:
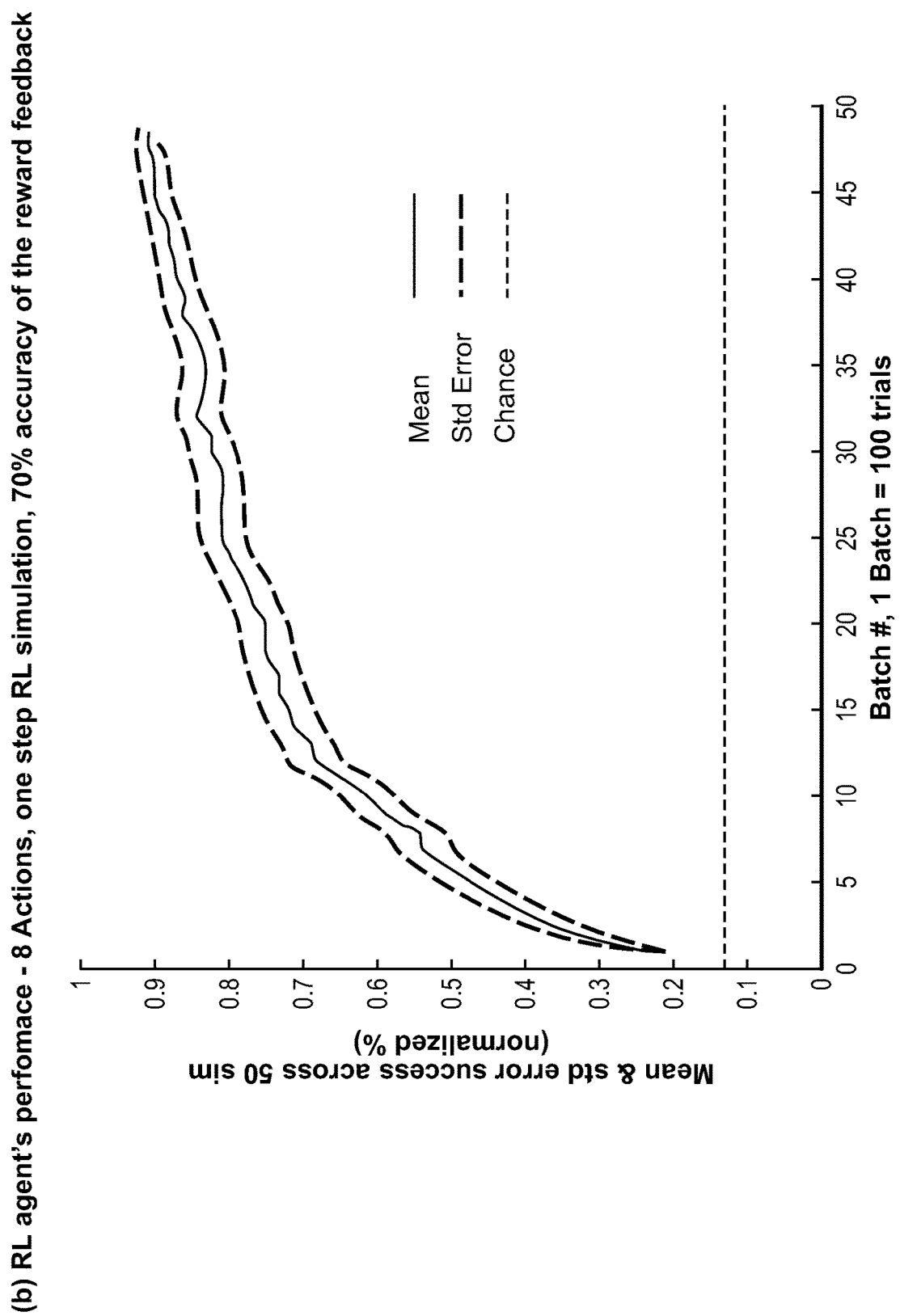
FIG. 12B illustrates an RL agent's performance in accordance with certain embodiments of the disclosed subject matter.

FIG. 12A shows an architecture of the offline RL simulation in accordance with certain embodiments of the disclosed subject matter. A task plane with 2 targets (left and right) was created as shown in the figure. The firing rate of the units in the simulated motor cortex was dictated by their tuning curves thus resulting in a differentiable neural signal for the two targets. The task utilized an ε-greedy policy RL agent (Multi-Layer Perceptron) to decode the firing rate of the neural ensemble and move the cursor in a given trial. The Multi-Layer Perceptron (MLP) mapped the firing rate of the neural ensemble calculated every 100 ms to the state-action values (Q values). The MLP had a hidden layer with 120 units and 8 units in the output layer representing the Q values of the 8 possible actions corresponding to movements spaced 45 degrees apart along the circle. Only one action is allowed to be made per trial to reach the intended target. A reward is given as a qualitative feedback of the executed action with an accuracy of 70% to reflect the success rate acquired by our reward classifier on OT2 data (reward=1 for the correct action; reward=−1 for the incorrect action). The qualitative feedback is used to adapt the RL agent through backpropagation. FIG. 12B shows RL agent's performance in accordance with certain embodiments of the disclosed subject matter. FIG. 12B corresponds to 8 actions, one step RL simulation, and 70% accuracy of the reward feedback. Mean and standard error of the RL agent's performance across 50 simulations is presented. Each simulation contains 5000 trials. The performance of the RL agent was calculated every 100 trials in a given simulation. The RL agent attained more than 90% success rate with 70% accuracy of the reward feedback.

FIG. 12a shows the task information, similar to OT2, as well as the neural network architecture used for the putative RL-BMI system (see methods). This work was conducted to determine if the M1 derived evaluative feedback would be sufficient to allow autonomous updating of a BMI as described in the methods. We utilized a simulated M1 for driving the BMI action decisions while simultaneously using the % correct evaluative feedback we had previously derived from M1 for OT2 (FIG. 10F). As can be seen in FIG. 12B, the system converges to ~90% success on this task using a rather simple RL learning system. This indicates that the generation of an autonomous RL-BMI should in principle be possible.

Discussion

The results demonstrate that bilateral primary motor cortices are modulated by reward expectation. M1 reward modulation is evident across manual and observation trial types. Hence, M1 units are modulated by reward even in the absence of arm movement or muscle activation as well as via the viewed trajectory of a cursor, perhaps acting like mirror neurons as these neurons also coded for kinematic variables. This population of neurons could be reward-modulated neurons, rather than mirror neuron, that respond to action observation as well as action itself. In addition, we have demonstrated that reward expectation can be predicted on a moment-to-moment basis using a classifier trained on principal component scores derived from M1 unit activities. We suggest that such reward classification can be used for the production of an autonomous Brain-machine Interface, which our collaborators and we are currently working towards. Both contralateral and ipsilateral M1 cortices contained units that were modulated by reward expectation, with the contralateral cortex containing a higher percentage of these units. M1 contain a population of units that fire more during rewarding trials and another that fire more during non-rewarding trials.

Throughout the three trial types presented here, both manual and observational, there existed a subpopulation of units that were reward modulated, but not modulated by movement. Thus our results imply that there may be separate neural populations in M1 that contain information about reward/reward expectation, movement, or both. Units found solely with reward modulation under this paradigm may have a preferred direction in an axis orthogonal to the ones used here and further work will be necessary to determine this. Our results indicate the presence of reward expectation information in M1 before movement execution. During the manual task, 29.3% of the 158 M1 units fired differentially for reward before the movement start cue.

The percentage of reward modulated M1 units was highest for OT1, followed by the manual task, and then OT2. This could be for a variety of reasons and we do not wish to speculate too much on this point, but one can imagine that this is due to the fact that the neurons may be coding for different amounts of information between these tasks, and the degree of variability of the signals being coded for may differ as well. For instance, in OT1 the speed profiles and kinematics of the trajectories are identical for all trials, while there is much more variability for the manual task, which also only involved movements to one target. On the other hand, OT2 involved movements to two targets that were in opposite directions. If the neurons code some information for each of the task relevant variables, such as kinematics and reward contingencies, then the amount of information that the units would need to encode under several assumptions could follow the same trend as the above for the percentages.

In addition to neural spiking, LFPs also showed consistent event related differences in delta and theta ranges between rewarding and non-rewarding trials. Studies have shown that the low frequency components of LFPs (up to 30 Hz) are not, or are minimally contaminated by spiking activity. Thus these LFP results provide additional information on a network level that may not be reflected in the spiking patterns. The reward related modulation of the low frequency components of LFPs observed across monkeys (see Local Field Potential Indications of Reward in M1) can also be utilized as an informative feature. Furthermore, the frequency band change with respect to reward expectation in the LFP signal is consistent with previous studies on Parkinson's disease models. This suggests that the mechanism of M1 reward differentiation could be rooted in dopamine signaling. The dopaminergic input from the ventral tegmental area directly to M1 is one potential source of reward modulation. The primary motor cortex is known to be directly or indirectly influenced by some of the major reward pathways (mesocortical, mesolimbic and nigrostriatal). Cortical structures such as anterior cingulate cortex (ACC), medial and dorsal prefrontal cortex (mPFC, dPFC), orbitofrontal cortex (OFC), lateral intraparietal cortex (LIP), parietal reach region, supplementary motor area (SMA), premotor area (PM) and frontal eye field (FEF) (for example, from Roesch and Olson, 2003a) are known to present these reward related signals. Many of these regions are known precursors of M1. Motor information from PMd (which is reward modulated itself) to M1 is just one source of movement related input.

In summary the neural activity (spike rate or LFP) in M1 can be mapped to desired movements by an appropriate decoder (actor) and the corresponding reward signal extracted from the same neural ensembles can be utilized as an evaluative signal (critic) of the performed action to allow subsequent autonomous BMI improvement. We have several lines of evidence from our lab and others that indicate we should be able to generate an autonomous BMI using neural activity from M1 for both the control of movement as well as to decode an evaluative signal as presented in this report. In our previous work we have demonstrated that even with a less than perfect evaluative signal a reinforcement learning based agent can do rather well, with such systems performing at levels as high as 93% success even when the evaluative feedback signal is only 70% correct.

EXAMPLE 3

Methods

Surgery

All surgical procedures were conducted in compliance with guidelines set forth by the NIH Guide for the Care and Use of Laboratory Animals and were further approved by the SUNY Downstate IACUC. Three bonnet macaques (*Macaca radiata*) were implanted in the primary motor cortex with chronic 96 channel platinum iridium microelectrode arrays (from example, 10×10 array separated by ~400 µm, 1.5 mm electrode length, 400 kOhm impedance, ICS-96 connectors, from Blackrock Microsystems, Salt Lake City, Utah).

Two of the animals were implanted in the contralateral (with respect to the right arm) primary motor cortex (M1, Monkey A and C), whereas Monkey Z was implanted in the ipsilateral (with respect to the right arm) M1. Intraoperative determination of the areas of interest within somatosenaory cortex were made with sharp electrodes and the motor cortex lying immediately adjacent to these areas reflected across the central sulcus were implanted with the electrode array as close as possible to the central sulcus placing the electrode in rostral M1. All surgical procedures were performed under general anesthesia and aseptic conditions were maintained throughout. Surgical procedures have been previously reported and are summarized here. Ketamine was used to induce anesthesia; isofluorane and fentanyl were used in maintenance of anesthesia. Dexamethasone was used to prevent inflammation during the procedures. All subjects were observed hourly for the first twelve hours post implantation and were provided with a course of antibiotics (baytril and bicilin) and analgesics (buprenorphine and rimadyl). An initial implantation of a footed titanium head post (for example, from Crist Instrument, Hagerstown, Md.) to allow head fixation during training was performed months before the electrode array implantation to allow for osteointegration. Head restraint of the animal is required for our experiments to ensure minimization of movement artifacts as well as to track the movement of the eyes.

Extracellular Unit Recordings

Single unit activity was recorded while the subject performed the task using externally synched Multichannel Acquisition Processor systems (for example, from MAPs, Plexon Inc., Dallas, Tex.). Signals were amplified, band pass filtered (for example, 170 Hz-8 kHz), sampled at, for example, 40 kHz, subjected to thresholding, and units (multi and single units, not differentiated in our analysis unless otherwise explicitly stated) were identified and sorted based on their waveforms using the Sort-Client software (for example, from Plexon Inc., Dallas, Tex.). Data shown for the manual reward experiment (see below) were acquired from Monkeys A and Z whereas the closed loop BMI data was acquired from Monkey C.

Experimental Setup and Behavioral Training

The use of animals in all procedures described here was approved by the IACUC of SUNY Downstate Medical Center and supervised by the department of comparative medicine (DCM) of SUNY Downstate Medical Center. Three bonnet macaques (two male, Monkey A and C and one female, Monkey Z) were trained to perform a center-out reaching task with the right arm resting in a robotic manipulandum (for example, from KINARM, BKIN Technologies, ON, Canada) in order to attain a juice reward. Following implantation each subject was allowed to recover for two to three weeks before training was resumed. The first experiment was run on monkeys A and Z. This manual reward experiment depicted in FIG. 2 required the animals to first hold their hand in a central start target for, for example, 325 ms before making a reaching movement within a fixed time (for example, in some embodiments, the maximum reach time allowed for Monkey A can be 1500 msec; and the maximum reach time allowed for Monkey Z can be 800 msec) and then holding in a peripheral target for, for example, 300 ms in order for a trial to be considered successful. There was a single peripheral reaching target located to the right hand side of the start target and, for example, 5 cm away from it. Two nearly identical trial types were used in this experiment; the only difference being whether or not the animal would receive a reward following a successful trial. The color of the peripheral target indicated the trial type as seen in FIG. 2 (for example, red indicates rewarding trials and blue indicates non-rewarding trials). If the trial was of the rewarding type a liquid reward was dispensed for 250 ms assuming all trial criteria were met. If the trial type was non-rewarding, no liquid reward was dispensed. At any point if the animal failed to complete a trial the next trial initiated would be of the same type as the previously failed trial. In this way the animal was given incentive to complete the non-rewarding trials. The Monkey's gaze was monitored by an IR sensitive camera and by real time image analysis (pupil tracking). A trial was aborted if the monkey failed to look at the task screen during the color cue period.

In addition to this manual experiment one monkey (monkey C) performed two distinct types of BMI tasks. The first BMI task utilized a reinforcement learning system, described below, and allowed movement in 8 directions equi-spaced about the unit circle. This task was used in order to gather data on M1's representation of reward expectation under such BMI control. The results from this closed loop RL-BMI were used to generate our neural critic and run our Actor Critic—Brain Machine Interface (AC-BMI), as described below in the sections on these topics.

Data Analysis

Principal component analysis was performed on the z-scored neural data (binned at 100 ms) from all trials. The PC scores were separated into rewarding and non-rewarding trials and used as inputs to train and test classifiers, which later acted as our neural critic for the actor critic BMI. Using the PC scores as inputs, a variety of classification methods were tested to determine the best method of predicting rewarding versus non-rewarding time bins as well as trials. The methods used for classification included both linear and quadratic discriminant analysis (classify function in Matlab) as well as the support vector machine technique (svmtrain & svmclassify function in Matlab). Training and testing was performed on 70% and 30% of the randomized data (PC scores) respectively. Repeated random sub-sampling cross validation (100 times) was performed to quantify the performance of the classifiers.

Differentiability between rewarding and non-rewarding PC score distributions for each task relevant time bin (100 ms) was tested (two sample Kolmogorov-Smirnov test with Bonferroni correction, $p<0.0031$). Differentiability between mean principal component scores across rewarding and non-rewarding trials were also tested using N-way ANOVA ('anovan' in Matlab) followed by post hoc test (multiple comparison, 'multcompare' in Matlab). To negate speed and time to reward as the possible sources of differentiability observed in the neural ensemble's firing rate for rewarding vs. non-rewarding trials we controlled for time to reward and maximum speed. The amount of time from the center hold period to the completion of the reward delivery period in a given trial was considered as the time to reward. Only those non-rewarding trials with time to reward and maximum speed within one standard deviation of the same for the rewarding trials were considered for further analysis. Previously mentioned statistical analysis was performed on the pruned data.

Temporal Difference Reinforcement Learning Overview

The theory of 'reinforcement learning' formulates the environment as a Markov Decision Process. Given an environment (neural activity here) and the current state of the actor (RL agent in our case) in the environment, RL suggests that the actor chooses an action not only to maximize its immediate expected reward but also its future expected rewards. The logic utilized by the actor to perform an action given a state is called its policy. An action performed by the actor under a given policy leads it to a new state in the environment and the consequence of such an action, interpreted through the critic, is utilized as feedback to modify its behavior/policy. Experience as well as learning rate influences the actor's behavior. An optimal policy intends to maximize the expected reward by performing the optimal action given a state in the environment. In our BMI case this would equate to moving the cursor in the manor that the animal wishes as translated via the M1 action intention information. A balance between exploration of uncharted territory and exploitation of current knowledge also defines an actor's behavior.

Temporal difference (TD) learning is a branch of reinforcement learning containing qualities from both dynamic programming and Monte Carlo methods. In dynamic programming a full model of the environment is available and necessary, whereas in Monte Carlo and temporal difference methods a full model of the environment is not needed. Monte Carlo methods update their policies at the end of an episode, where an episode could be a single reaching movement, while temporal difference methods can update their policies during an episode, or reach in our case. Given the rational that a BMI user would like to update the decoder over successive time steps while reaching a target and that, in real world situations there is no model of the environment; TD learning is a logical RL algorithm to use compared to Monte Carlo Methods or Dynamic Programming. Actor-critic methods are TD methods that have the actor (policy) and the critic (estimated value function or the evaluative feedback signal provider) exist as two independent entities. The critic, as stated earlier, criticizes the actions executed by the actor, and in our case will be a classifier that divides the neural data from M1 between rewarding and non-rewarding trial types, or motions.

As noted an RL agent strives to learn an optimal policy wherein a policy is the logic utilized by the actor to perform an action given a state to maximize its immediate and future rewards. One method of RL utilizes a state-action value function, $Q\pi(s,a)$, which is the expected return starting from state 's' given that the RL agent executes the action 'a' in state 's' under a policy $\pi$. Specifically, the actor in our architecture utilized an $\varepsilon$-greedy policy and Q learning. The action with the highest Q value was selected 1-$\varepsilon$ percent of the time (exploitation) whereas a random action is performed $\varepsilon$ percent of the time (exploration) under the $\varepsilon$-greedy policy. There are also ways to change $\varepsilon$ given the systems performance, but such full descriptions are outside the scope of this work.

In Q learning, the TD error equation is:

$$TD\_error: r+\gamma^* \max_{a'} Q(s',a') - Q(s,a)$$

Where; $r=\{-1,1\}$ is the immediate reward.
$\gamma$=the discount rate and its allowable range is [0,1). In our case; $\gamma$=0 resulted in a myopic agent.
(s, a)=the previous state and the action performed in state s under the $\varepsilon$-greedy policy $\pi$ respectively.
(s', a')=the current state and a' is the greedy action in state s' respectively.

The TD error is used as feedback to update the estimates of the state-action values (Q values).

$$Q(s',a')=Q(s,a)+\alpha^*TD\_error$$

Where; $\alpha$=learning rate.

In our Actor-Critic Brain Machine Interface (AC-BMI) architecture, r is the class label predicted by a reward classifier (critic) whose input is the neural activity. Specifically, when population firing is classified as rewarding, r is set to 1, whereas when the neural activity is classified as non-rewarding, r is set to −1. As such, a classifier outputs a binary evaluative measure by decoding the neural signal, which critiques the executed action. The architecture suggested here conforms to a broader definition of the actor-critic architecture as it has a separate memory structure to explicitly represent the policy independent of the entity providing the evaluative signal. The scalar evaluative signal is the sole output of the critic and drives all learning in the actor. The suggested architecture can easily be modified to conform to the stricter definition of actor-critic wherein the critic represents the estimated value function and the evaluative feedback provided by the critic is utilized to update itself along with the actor. One can also envision versions where the user gives feedback on the critic's performance as a perfect source of feedback to update the critic and subsequently the actor when necessary (Supervised Actor Critic BMI).

Closed Loop Actor Critic—Brain Machine Interface (AC-BMI)

Monkey C initially performed a 4 target-8 action closed loop RL-BMI (Q-learning) wherein the immediate reward utilized to update the decoder (actor) was provided by the task. Therefore, +1 and −1 was provided as the immediate reward for a correct and an incorrect action respectively. The RL-BMI trials, which were completed successfully, were considered as rewarding trails, whereas unsuccessful trials were labeled as non-rewarding trials. The RL-BMI data was utilized to train the critic utilized by the AC-BMI. Monkey C then performed a 2 target-2 action closed loop AC-BMI. One of the two targets was shown in a given trial. The task required the monkey to move the cursor from the center to the peripheral target using the AC-BMI. The reward on successful trials was delivered for 250 ms. The monkey received only one opportunity per trial to execute the appropriate action using the AC-BMI. The actor was initialized with random weights and the critic was trained from the M1 data collected from the closed loop RL-BMI task.

Actor—neural data (100 ms bins, 5 bins into the past) from the contralateral M1 (with respect to the right arm) of Monkey C was mapped to the state-action value (Q value) for each of the two possible actions (towards and away from the target) by a Multi Layer Perceptron (MLP), with one hidden layer containing 10 units. The activation in the hidden units was computed by applying the hyperbolic tangent nonlinearity to the weighted sum of the inputs to the hidden layer (fh( )=tan h($\Sigma$W.I); where W=weight matrix & I=input vector to the hidden layer). The output layer of the MLP consisted of 2 units representing the Q value for each of the two available actions. The activation of the output units was computed as the weighted sum of the inputs to the output layer from the hidden layer. The action with the highest Q value was executed 99% of the time (the "greedy" part of the ε-greedy policy), whereas a random action was taken 1% of the time (the exploratory rate, the 'ε' part of the ε-greedy policy). The random exploration allows for discovery of new solutions by the RL agent, useful especially in an altering environment.

Critic—M1 neural data recorded while monkey C performed the Q learning RL-BMI experiment was used to train our critic (see Data analysis) utilized by AC-BMI. As a reminder, the only difference between the two algorithms was the fact that the Q learning RL-BMI utilized the external scalar evaluative feedback (immediate reward) provided by the experimenter, whereas the AC-BMI utilized the internal scalar evaluative feedback (immediate reward) stemming from the subject's motor cortex to update the actor. The RL-BMI trials in which the cursor moved towards the target were considered as rewarding whereas trials in which the cursor moved away from the target were considered non-rewarding. The classifier (critic) was then trained and tested for its capability to differentiate between rewarding and non-rewarding trials every 100 ms (see Data analysis), which was the bin size. The top 10 principal component scores were utilized as inputs to the classifier, which in essence classifies the M1 neural data critiquing the action performed by the actor, as rewarding (immediate reward, r=1) or non-rewarding (immediate reward, r=−1). Leave-one out analysis on the Q learning RL-BMI data was performed in order to find the time point in a given trial post the color cue with the highest combined average of true positives and true negatives. For Monkey C, this meant that the 24th bin (each bin=100 ms) post the color cue had the highest combined average of true positives and negatives in the leave-one out analysis. Neural data corresponding to this time point (maintained across all the trials) post color cue in the AC-BMI experiments was classified as rewarding or non-rewarding thus providing us with the immediate reward value. This reflects the M1's assessment of the action just performed by the AC-BMI agent. Update of the MLP weights was performed by backpropagation of a qualitative error signal 'TD error' calculated utilizing the immediate reward it received from the classifier.

The implementation of this strategy allowed the MLP to learn the optimal mapping between the M1 neural data and the intended action. Monkey's gaze was monitored by an IR sensitive camera and by simple real time image analysis (pupil tracking). A trial was aborted if the monkey failed to look at the task screen during the color cue period.

Offline Simulation

We have previously described the use of a reinforcement learning (RL) paradigm in which an RL agent performed a 4 target-8 action center out reaching task by decoding the firing rate of a simulated M1 neuronal ensemble. We utilized this same neural model in our current work to test whether the success rates achieved by our classifiers were enough to train our RL agent as shown in FIG. 5. In this model a group of neurons was simulated using the Izhikevich model in order to represent a simulated motor cortex. The neural ensemble consisted of 80 neurons wherein; 60% of the neurons were assigned a unimodal tuning curve, 15% were assigned a bimodal tuning curve and 25% were assigned an asymmetric tuning curve. All the neurons had a baseline firing rate. A tuning curve directed the degree of modulation with respect to the corresponding neuron's baseline firing rate given the direction of the target with respect to the present cursor position. Preferred directions of these neurons were assigned randomly. A spike was detected every time the membrane potential of a neuron surpassed 30 mV. The firing rates for these neurons were generated, for example, every 100 ms to provide a time scale close to firing rates observed during behavior. The task involved moving a cursor from the center of the task plane to one of four peripherally placed targets by decoding the intention of this simulated motor cortex given the possibility of a movement by the cursor in eight directions at any given time (the first direction is to the right and the remaining 7 directions are at 45 deg intervals to the first direction) utilizing the ε-greedy policy presented earlier (FIG. 5).

The target direction in a given trial changed each neuron's firing rate with respect to its baseline activity based on their respective tuning curves. That is, given a target in the left direction, the neurons that had their preferred direction to the left fired at their maximum firing rate whereas the remaining neurons modulated their firing based on their tuning curve. Using the output of the simulated neural ensemble as the input to an artificial neural network the Q value for each potential action was determined. Specifically, a multilayer perceptron (MLP) with a single hidden layer consisting of 120 units was used to calculate the Q value given an input from the neural ensemble. 99% of the time the action with the highest Q value was executed (the "greedy" part of the ε-greedy policy), and the other 1% of the time a random action was taken (the exploratory rate, the 'ε' part of the ε-greedy policy). Exploratory rate, defined as the percentage of steps in which an action is executed randomly irrespective of its optimality at a given state, was set at 1% (' part of ε-greedy policy). The random exploration allows for discovery of new solutions by the RL agent, useful especially in an altering environment. Update of the weights of MLP was performed by backpropagation of a qualitative error signal 'TD error*eligibility trace' calculated utilizing the immediate reward it received based on the correct or incorrect action performed. A correct action resulted in +1 as the immediate reward whereas an incorrect action was awarded with −1. The implementation of this strategy allowed the MLP to learn the coast towards the optimal mapping between the simulated neural output and proper control of the task. Multiple simulations where the immediate reward value provided as feedback to update the RL agent was varied from 50% to 100% accuracy at 10% intervals per simulation session were performed. The immediate reward was considered to be provided accurately if +1 was given for a correct action whereas −1 was awarded for an incorrect action. Inaccurate immediate reward gave −1 for a correct action and +1 for an incorrect action. Accurate and inaccurate immediate reward values were provided randomly in a given simulation for a given overall accuracy level being tested for that simulation session. The accuracy of the immediate reward provided as feedback reflects the classifier's (critic's) accuracy on the M1 neural data acquired during the manual reward experiment and AC-BMI.

Results

Reward Expectation Modulates M1 Neural Activity

Figure 13:
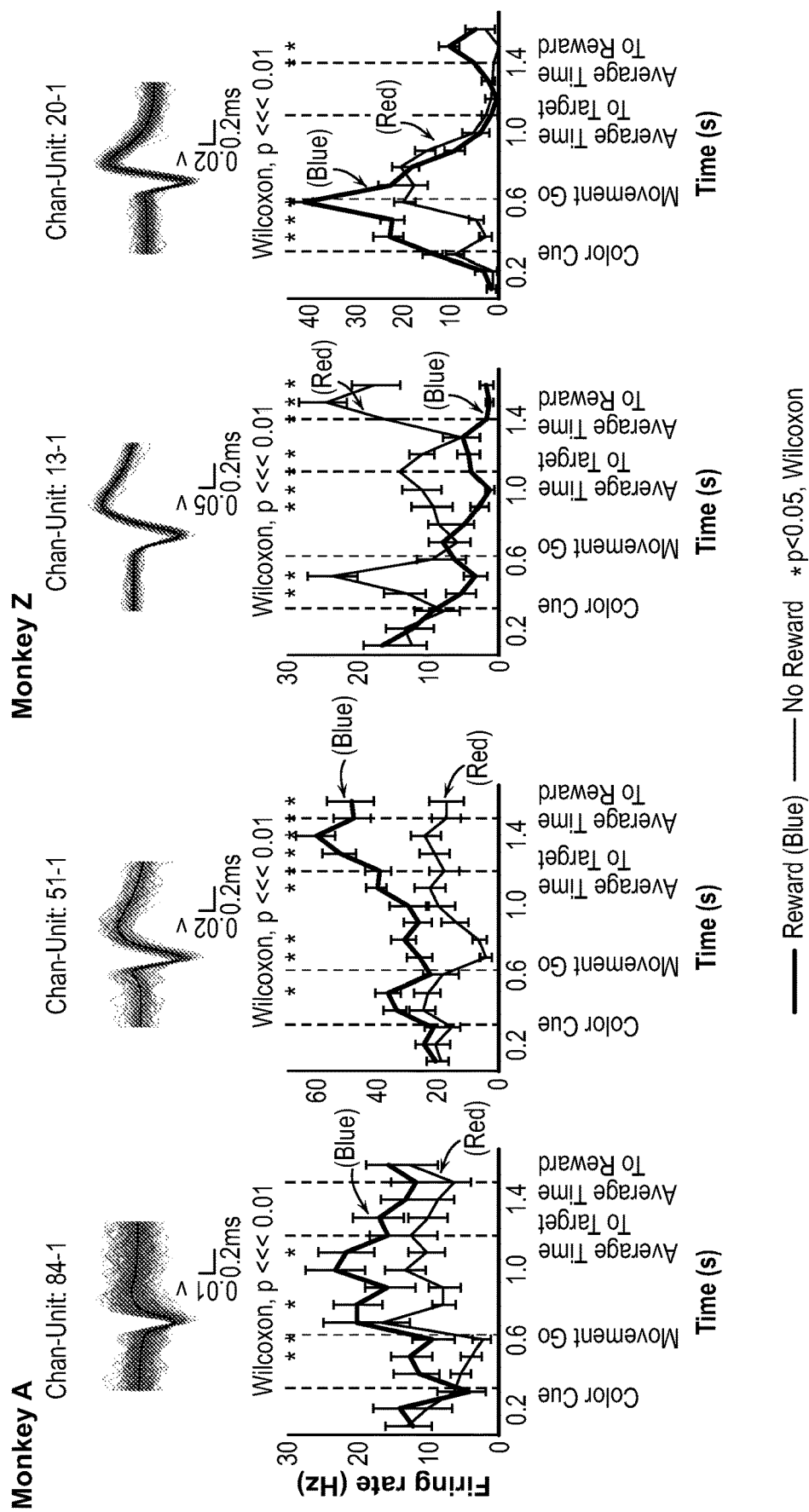
FIG. 13 illustrates data from single M1 units under two conditions, rewarding and non-rewarding, as part of the behavioral task performed by the monkeys in accordance with certain embodiments of the disclosed subject matter.

Part of our long-term goal is to develop an autonomous BMI that would require as little surgical intervention as possible. Toward this goal we tested M1 for reward related modulation that we later show can be used as a critic to provide evaluative feedback on recent BMI movements. These movements were be guided by M1 activity as well. In FIG. 13 we present data from single M1 units under two conditions, rewarding and non-rewarding, as part of the behavioral task performed by the monkeys. As a reminder, the monkey used its right arm to make reaching movements to a single visual target that was color cued indicating if reward would be received for making a good reaching movement (see FIG. 2).

FIG. 13 shows results from example single units. FIG. 13 includes mean and standard error of example unit's firing rates across rewarding and non-rewarding trials for Monkey A and Z. Neural data was binned at, for example, 100 ms. Wilcoxon test was performed at every bin to test the significance of the differentiability between the rewarding and non-rewarding firing rate median at the corresponding time point. The time points with an asterisk had a significant difference (wilcoxon, $p<0.05$). Multiple time bins post color cue had significant differences between the rewarding and non-rewarding neural firing rate medians. The color of the center and the target at color cue period informs the monkey if it will receive a juice reward post the successful completion of the trial. Above each subplot are shown the mean single unit waveforms for the corresponding example units in black along with sample waveforms in gray. At the top of each subplot is the average waveform of the putative single unit along with sample raw waveforms. Below the waveforms are the mean firing rate+SEM from 100 ms bins for successful rewarding (blue) and non-rewarding trials (red). Wilcoxon test ($p<0.05$) was performed at every bin to test the significance of the differentiability between the rewarding and non-rewarding firing rate median at the corresponding time point. Time points with an asterisk have a significant difference (Wilcoxon test, $p<0.05$). Multiple time bins post the color cue have a significant difference between the rewarding and non-rewarding neural firing rate median. The single unit's, median response across rewarding and non-rewarding trials was also significantly different (Wilcoxon, $p<<<0.01$).

In order to utilize information from the neural population while reducing the dimensionality of the raw data we performed principal component (PC) analysis. We wished to see if the PCs were differentiable with respect to the trial type. The application of the Kolmogorov-Smirnov (KS) test (with Bonferroni correction, $p<0.0031$) to compare PC1 and PC2 distributions for each corresponding time bin within the two trial types showed a differentiable expectation of reward delivery within the motor cortex in time bins following the presentation of the color cue as shown in FIG. 3. Mean principal component scores across rewarding and non-rewarding trials were significantly different (N-way ANOVA followed by post hoc multiple comparison test).

Figure 14A:
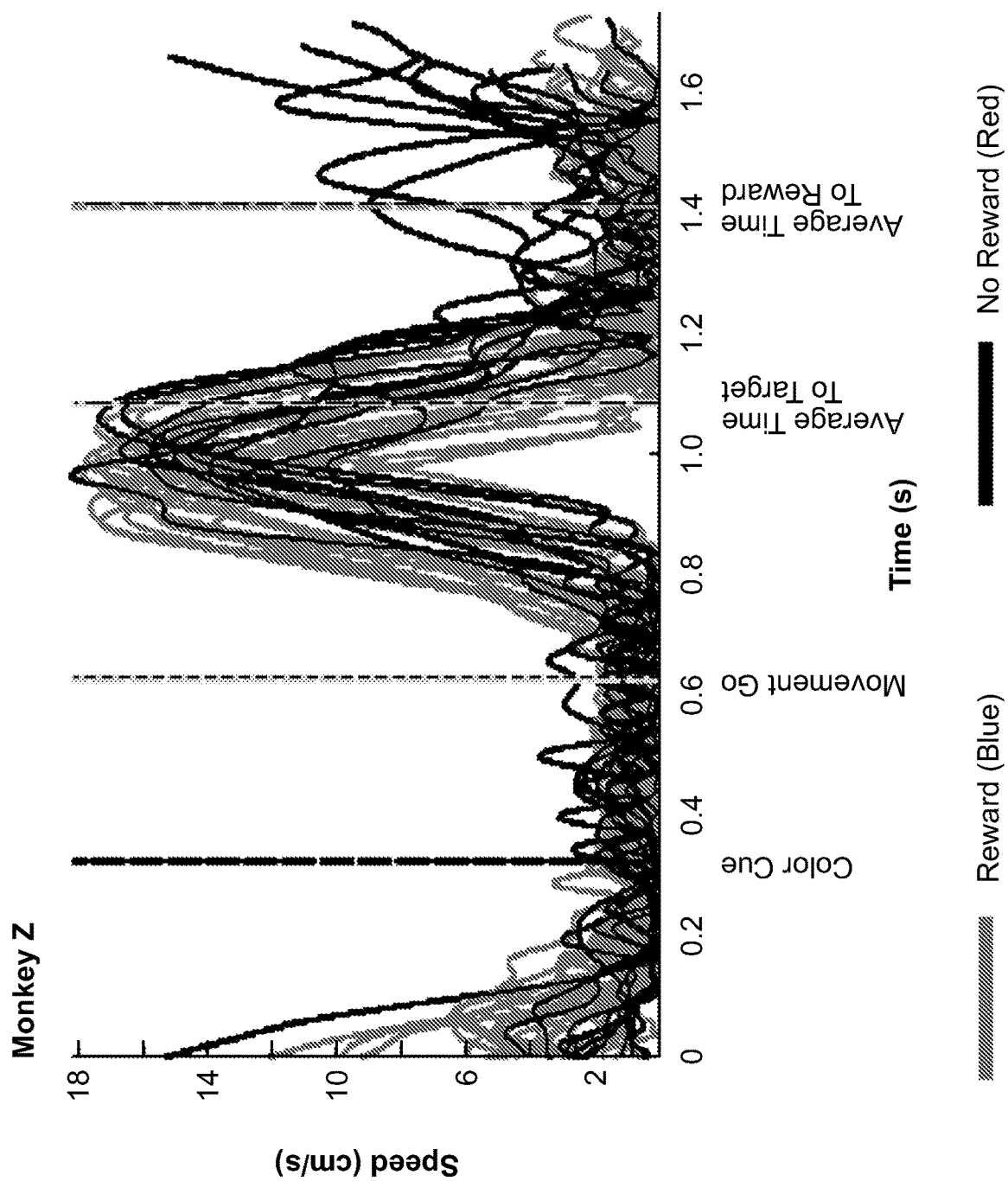
FIG. 14A illustrates post pruning speed profiles of both rewarding and non-rewarding trials for Monkey Z in accordance with certain embodiments of the disclosed subject matter.

In order to control for potential confound of our results caused by kinematic differences between trials, those trials determined to be outliers were selectively pruned (see methods). FIG. 14A shows post pruning speed profiles of both rewarding and non-rewarding trials for Monkey Z in accordance with certain embodiments of the disclosed subject matter. Only those rewarding and non-rewarding trials with time to reward within 1 standard deviation of the mean of the time to reward of the rewarding trials, and with a maximum speed within 1 standard deviation of the mean of the maximum speed of the rewarding trials were selected. The pruning was performed to eliminate kinematic differences between rewarding and non-rewarding trials as a possible source for the significant differences observed in the neural data. Further analysis on these trials confirms that the differences observed in the M1 neural modulation is primarily due to the trial type (rewarding or non-rewarding) as shown in FIG. 14B.

Figure 14B:
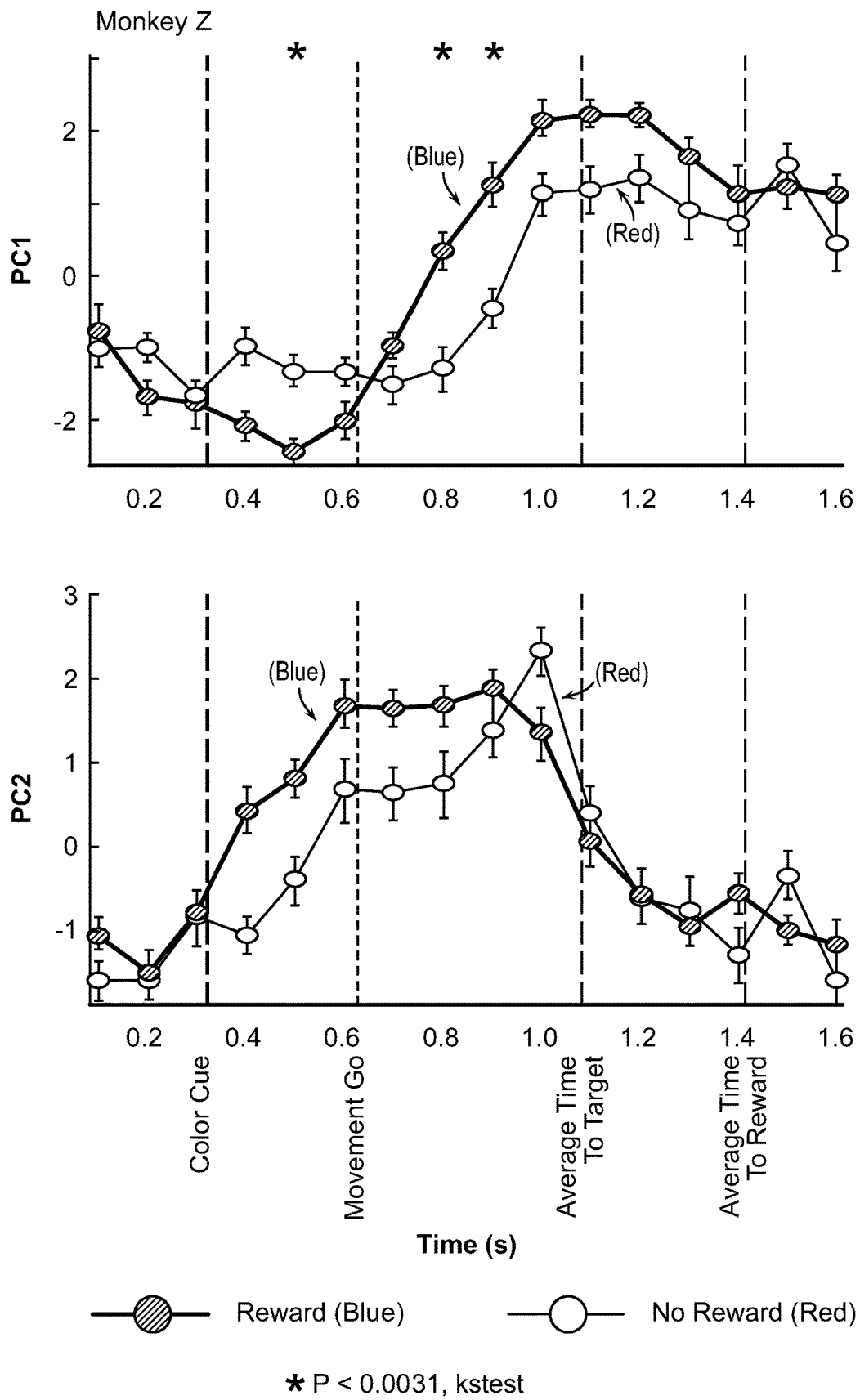
FIG. 14B illustrates mean and standard error of principal component scores across pruned rewarding and non-rewarding trials for Monkey Z in accordance with certain embodiments of the disclosed subject matter.

FIG. 14B shows mean and standard error of principal component scores across pruned rewarding and non-rewarding trials for Monkey Z in accordance with certain embodiments of the disclosed subject matter. Principal Component (PC) scores were calculated on the standard scores (z-scores) of the neural data binned at 100 ms from the pruned trials (controlled for time to reward and maximum speed). A two-sample Kolmogorov-Smirnov test was performed at every bin (neural data was binned in 100 ms bins) to test the significance of the differentiability between the rewarding and non-rewarding PC score distributions at the corresponding time points. The time points with an asterisk had a significant difference (kstest with bonferroni correction, $p<0.0031$) between the rewarding and non-rewarding PC score distributions. The rewarding and non-rewarding PC scores were significantly different at multiple time points post the color cue. The differences observed here were due to the presence or absence of a juice reward at the end of the trial as the trials considered had similar time to reward and maximum speed during their reach. The color of the center and the target (color cue) informs the monkey if it will receive a juice reward post the successful completion of the trial. Mean PC scores across pruned rewarding and non-rewarding trials were also significantly different (N-way ANOVA followed by post hoc multiple comparison test). In FIG. 14B, PC1 represents principal component 1; PC2 represents principal component 2; and kstest represents Kolmogorov-Smirnov test (with bonferroni correction, $p<0.0031$).

we have not shown results for monkey A as a sufficient number of trials required to test significant differentiability of the mean PC scores with respect to trial type (n-way ANOVA with post hoc multiple comparison test) did not pass through the pruning process. Distributions of the first two principal components for each time bin from rewarding and non-rewarding trials were compared using the two-sample KS test for monkey Z (with Bonferroni correction, $p<0.0031$). Controlling for the kinematic variability by pruning outliers provided very similar results to the same analysis without pruning; the distributions of both PC1 and PC2 was found to be significantly different following the presentation of the color cue, but not before the presentation of the color cue as shown in FIG. 14B. Mean principal component scores calculated across pruned rewarding and non-rewarding trials were also significantly different (N-way ANOVA followed by post hoc multiple comparison test). This finding further suggests modulation of M1 by reward expectation.

Figure 15:
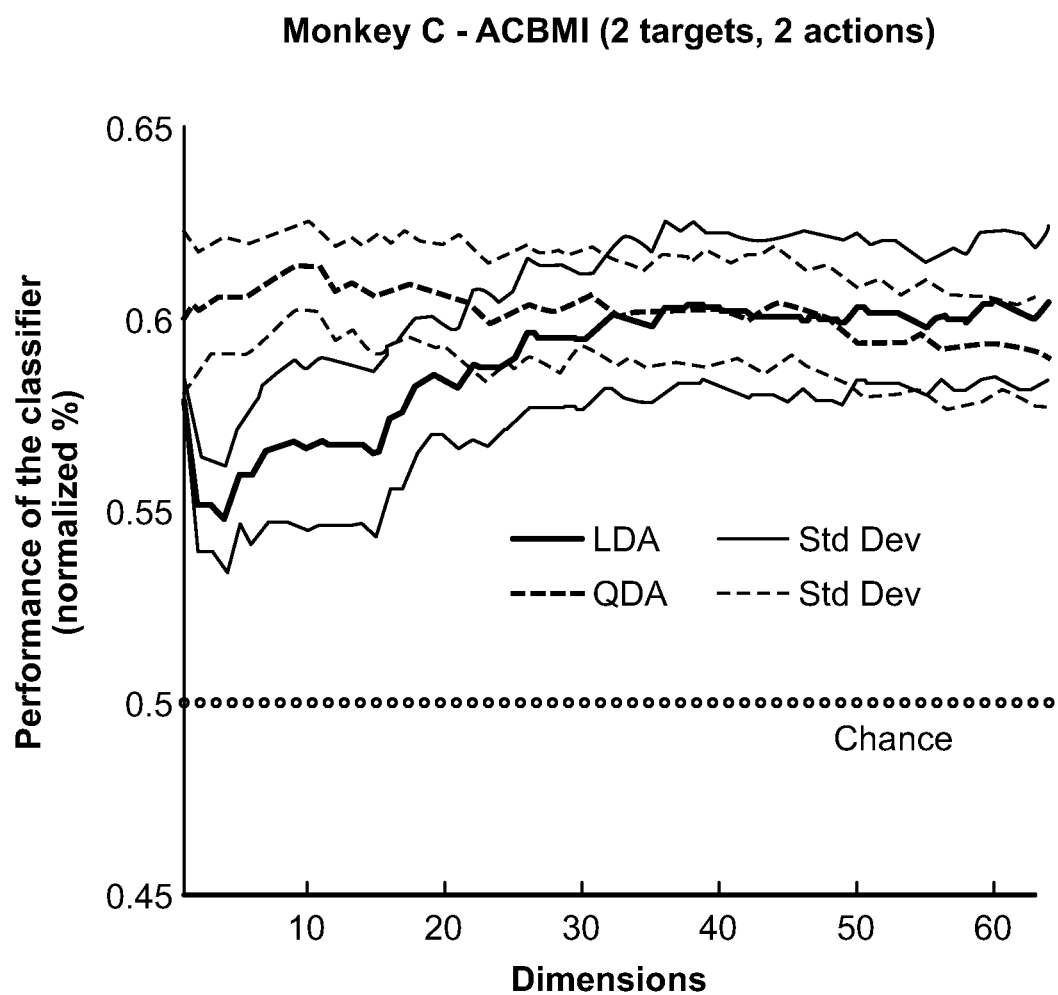
FIG. 15 illustrates linear and quadratic discriminant analysis results on 2 target-2 action closed loop BMI task for Monkey C in accordance with certain embodiments of the disclosed subject matter.

M1 Neural Data Corresponding to Rewarding and Non-Rewarding Trials can be Reliably Differentiated on a Moment-to-Moment Basis In FIG. 4 we have plotted the performance of our neural classifiers that determine if a time bin is rewarding or non-rewarding. We have plotted the mean and the standard deviation of repeated random sub-sampling validations (100 times) of both linear and quadratic discriminant analysis (LDA and QDA) on the manual reward experiments, and the closed loop AC-BMI data in FIGS. 4 and 15 respectively. FIG. 15 shows Linear & Quadratic discriminant analysis results on 2 target-2 action closed loop BMI task for Monkey C in accordance with certain embodiments of the disclosed subject matter. Monkey C performed 2 target-2 action closed loop AC-BMI. The actor was initialized with random weights. The critic used in the AC-BMI was trained on the M1 neural data acquired while the monkey previously performed 4 target-8 action closed loop RL-BMI. See 'Closed loop Actor Critic—Brain Machine Interface (AC-BMI)' in methods section for further details. Monkey C performed the 2 target-2 action center-out reaching task in closed loop with the AC-BMI decoder at 60% accuracy. The successful AC-BMI trials were considered as rewarding trials whereas the unsuccessful trials were considered as non-rewarding trials for training and testing our classifiers. The performance of the classifier (normalized %) on the testing data is shown here with respect to the number of principal components (dimensions) used. Principal Component (PC) scores were calculated on the standard scores (z-scores) of the neural data binned at 100 ms. The training and testing of the classifier was performed on 70% and 30% of the randomized PC scores calculated on the z-scored neural data binned at 100 ms (see Data analysis). Repeated random sub-sampling validation (100 times) of the linear and quadratic discriminant analysis (LDA and QDA) was performed for each point on the X-axis. The classifier was able to discriminate rewarding from non-rewarding data with over 60% accuracy. The results of the offline simulations shown in FIG. 16 blow suggest that above 60% classifier accuracy is enough to train the actor (decoder) successfully in the suggested architecture.

The highest success rate achieved by the classifiers on the testing data from the manual reward experiments and the closed loop AC-BMI was equal to or above 75% and 60% respectively (chance=50%). We also tested the performance of LDA and QDA classifiers with respect to the number of PC components (dimensions) that were being used. Around 22 principal components for Monkey A and 6 principal components for Monkey Z were deemed sufficient to result in the maximum performance on the manual reward experiment data. Whereas, about 30 principal components for Monkey C, performing the closed loop AC-BMI task, were sufficient as inputs to the LDA classifier to attain its maximum performance. The performance plateaued post the 'optimal' number of principal components. These results show that we can differentiate rewarding and non-rewarding trials on a 100 ms time scale.

Offline Simulation Results

Figure 16:
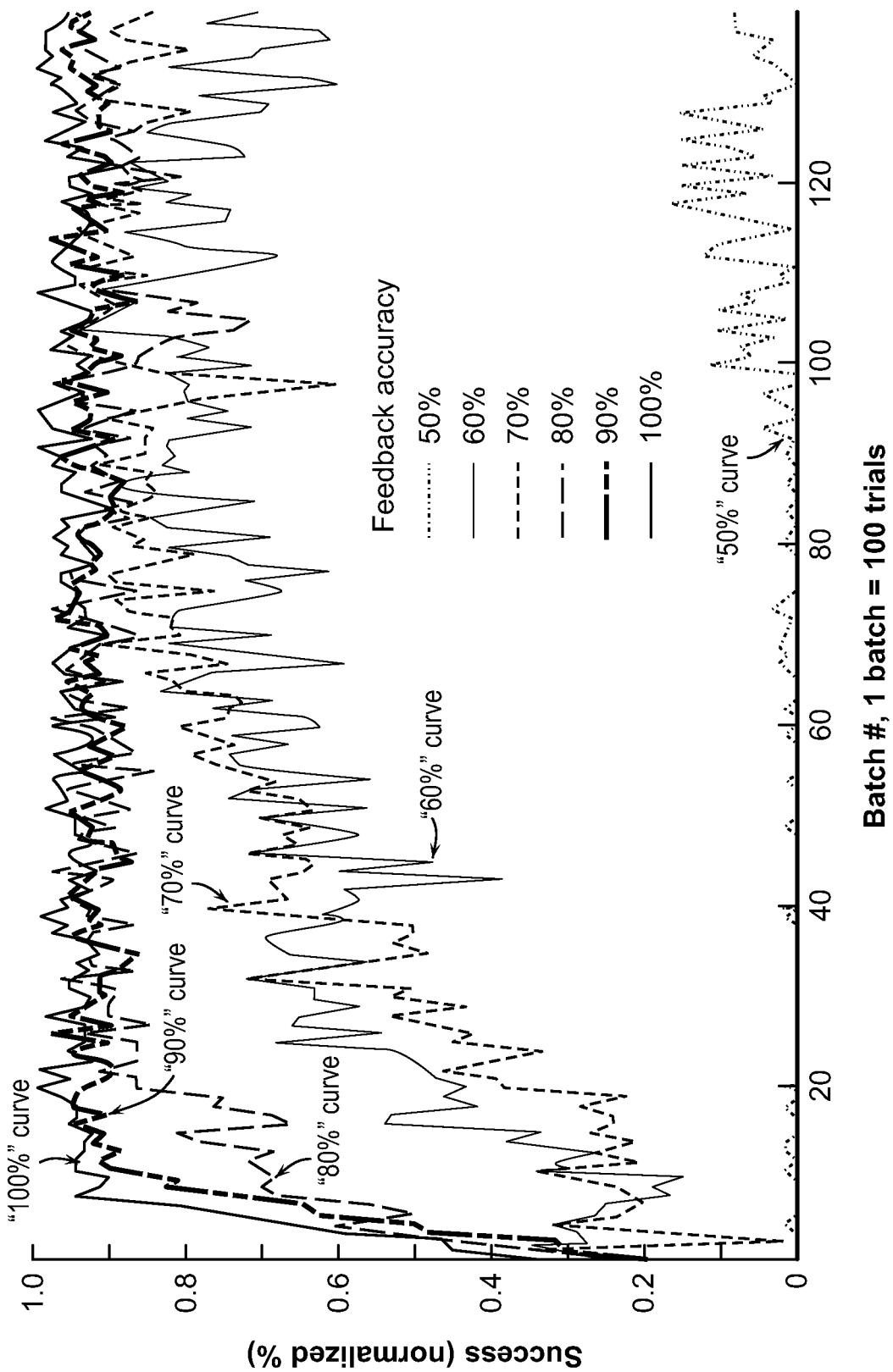
FIG. 16 illustrates success rate of the RL agent versus accuracy of the feedback in accordance with certain embodiments of the disclosed subject matter.

The maximum success rate achieved by our classifiers was about 75% on the manual reward experiment data and about 60% on the closed loop AC-BMI data, which means that the classifier would be providing the wrong feedback 25% and 40% of the time respectively. Therefore, we wanted to test if such an accuracy rate would be enough to train the RL decoder given time. Simulations were performed to ascertain the effect of the reward feedback accuracy on the RL agent's performance. A correct action, as stated in the methods section, in the normal scenario was awarded with +1 as the immediate reward whereas an incorrect action was given a −1. Accuracy of the immediate reward provided to calculate the qualitative error signal used in adapting the RL agent through backpropagation was varied from 50% to 100% in intervals of 10% for independent simulations (FIG. 5B). 50% accuracy meant that the correct value for the immediate reward, corresponding to the action performed, was provided as feedback only 50% of the time and the other 50% of the time the incorrect feedback was provided. The RL agent was able to perform at a success rate of 80% and above for feedback accuracies of 60% and above as shown in FIG. 16 below. Hence we claim that success rates achieved by our classifiers are more than sufficient to train/adapt the RL decoder in a closed loop BMI system.

FIG. 16 illustrates success rate of the RL agent vs. accuracy of the feedback in accordance with certain embodiments of the disclosed subject matter. Several simulations were performed to quantify the effect of varying the accuracy level of the reward feedback on the RL agent's performance. The accuracy of the immediate reward provided to the RL agent was varied from 50% to 100% in 10% intervals per simulation session, and inaccurate rewards were provided randomly in these simulations. Results suggest that the actor (decoder) can be trained to attain maximum performance with above 50% feedback accuracy. These results also imply that the success rates achieved by our classifiers on the manual reward data (FIG. 4) and the 2 target-2 actions closed loop RLBMI data (FIG. 15) are sufficient to train an actor (decoder) in future closed loop actor-critic RL or supervised actor-critic reinforcement learning brain machine interface (SAC-BMI).

Discussion

We introduce a BMI implementation that is autonomous i.e. it updates itself by sensing when things were not working as intended. This system utilizes neural activity from, for example, the primary motor cortex, a readily accessible region for electrode implantation that has been used in humans for BMI purposes. We have shown activity in this region can be used for extraction of both motor intent and information on reward expectation of ongoing movements. We have further shown that it is possible to differentiate rewarding from non-rewarding movements on a moment-to-moment basis from the same M1 population utilized in the extraction of limb kinematics and movement intention. These findings demonstrate the modulation of M1 by the expectation of reward. We subsequently presented that the reward signal from M1 could be used as a critic suitable for implementation in reinforcement learning based systems, something we have previously shown using hemodynamic signals. We also showed that the monkey was able to perform a 2 target-2 action closed loop AC-BMI center out reaching task with 60% accuracy while using the feedback provided by our critic. Apart from the obvious differences between the offline simulation performed and the closed loop AC-BMI, the lack of epoch training of the decoder (MLP; neural network) in the closed loop AC-BMI scenario may have contributed majorly to the difference in the decoder's performance observed between the two scenarios. We have further demonstrated reward modulation in M1 both when the subject is performing a closed loop BMI task and when simply viewing the cursor trajectories that result in either the provision or the withholding of a juice reward (results of the cursor viewing experiments to be published in a separate paper). Our previous work has demonstrated the utility of non-invasive methods in the derivation of a reward expectation signal from frontal brain regions of animals passively viewing rewarding or non-rewarding cursor movements. The use of information gathered using non-invasive measures would certainly be beneficial in supplementing the critic signal derived from the M1 array in our currently presented RL based BMI architecture.

Advantages to RL-BMI Architectures

One of the clearest advantages of the system we have proposed is that there is no need for explicit training data as is the case for BMIs utilizing supervised learning methods. The reliance on methods requiring explicit training data is a central issue that partially explains the lack of widespread clinical BMI use; a paralyzed person cannot elicit movements to be used in the training of a BMI. There are of course workarounds such as using neural activity associated with action observation; however this still requires full knowledge of the viewed target and cursor. The implementation we describe here does not need an exact error signal such as the difference between a real and intended movement; one can simply know if what the BMI is doing was the user's intention. This evaluative feedback needn't be on a moment-to-moment basis either; it could be calculated at the end of a movement. In a real life scenario, the detection of the movement onset and completion will allow for easy segmentation of time into episodes. If the BMI is doing something unwanted this should lead to a negative output from the critic derived from the neural activity, and if something desired is occurring a positive output should be derived. As we are dealing with neural systems there is always uncertainty and noise, and thus one can simply threshold the outputs from the critic so that unnecessary updating of the actor does not occur. One can easily use methods developed under statistical hypothesis testing to provide a confidence measure to the critic's output.

Reinforcement learning based BMI system learns from experience. There are ways to speed up the learning process through mechanisms such as 'fitted Q learning' wherein one can iteratively replay the experienced data through the system with added noise and a slow learning rate. The additional noise reduces the chance of over fitting by the neural network and a slow learning rate helps keep the system stable. It has also been shown that for simple RL-BMI systems fast convergence is possible. Importantly, one can start off by training the weights of the BMI policy with a supervised approach, which currently obtain impressive success rates, and then when the individual is out in the real world utilize an RL based system, such as the one we have proposed, to update the system when necessary. One can continue to switch between supervised learning and RL to modify the actor in the actor-critic framework as shown in FIG. 1B.

It has also been shown that RL-BMI systems can adapt when the neural environment changes, such as when one loses or gains single units on the electrode array that is feeding data into the BMI. These aspects make RL-BMIs very appealing and with an informative critic like signal derivable from the brain the system can work autonomously. Even in the case when the neurally decoded critic is faulty the user can give the system the correct input (see FIG. 1B), as a simple binary feedback, that is the user will let the system know when it is wrong. This would only be necessary when the critic is wrong; as if the actor is incorrect the critic will update the system. The level of interplay between the user and the system as well as the threshold to decide when the actor will be updated by the critic can easily be tailored to the individuals liking. Implied in these statements is that the user would have information on the critics decisions, and would therefore know if the critic was faulty. Such simple binary feedback should be derivable from most users via speech, eye movements, tongue movements etc. As technologies move forward one can easily imagine the user simply identifying the goal of a reach to help recalibrate the system rather than having to give continues feedback to the critic. All of this is only necessary if the system is not performing to the users' acceptable level. We believe such an encompassing system will allow the two learning agents (BMI and user) to co-adapt successfully.

Conclusion

The primary motor cortex (M1) modulates differentially to the presence or absence of reward at the end of a given trial. Such a differential modulation was not caused by any kinematic differences between the trials types. The reward modulation in M1 was present along with the kinematics based modulation in M1. Our classifiers were able to classify the M1 neural data corresponding to rewarding and non-rewarding trials with an accuracy above 70% on a moment by moment (100 ms) basis. A reinforcement learning BMI was designed to utilize the reward modulation in M1 as an evaluative feedback signal to update the decoder. Under the actor-critic reinforcement learning architecture, the neural data from M1 was mapped to the intended action by the decoder (actor) whereas the critic classified the neural data from the same neural ensemble as rewarding or non-rewarding. The evaluative signal provided by the critic was utilized as feedback to update the actor. Monkey C performed a closed loop 2 target-2 action AC-BMI task with 60% accuracy while using feedback from our critic. Our classifiers were able to classify M1 neural data corresponding to the AC-BMI trials as rewarding or non-rewarding with 60% accuracy. We also show through offline simulations that the success rates achieved by our classifiers (critic) were sufficient to update our actor to convergence under the RL architecture. We therefore suggest an amalgamation of the supervised and reinforcement learning architecture (supervised actor-critic reinforcement learning), which would allow the system to switch between utilizing the supervised error signal or an evaluative signal as feedback, thus resulting in an autonomous BMI. Such an autonomous BMI, in theory, would be more generalizable to inexperienced environments.

Systems

Figure 17:
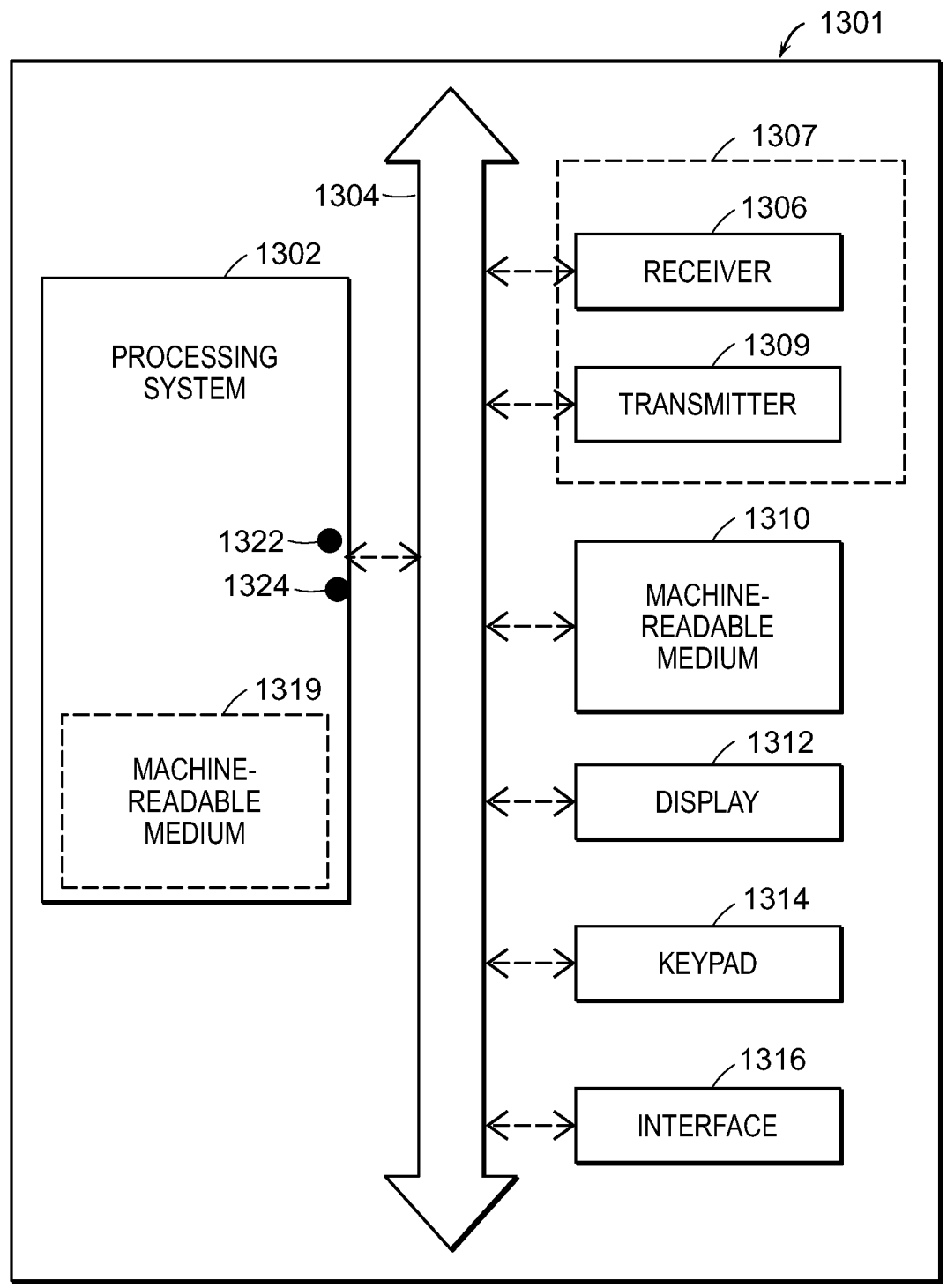
FIG. 17 is an exemplary diagram of modules implementing methods of the subject technology.

Some embodiments of the subject technology comprise systems for generating and applying biomimetic signals. FIG. 17 is a conceptual block diagram illustrating an example of a system, in accordance with various aspects of the subject technology. A system 1301 may be, for example, a client device or a server. The system 1301 may include a processing system 1302. The processing system 1302 is capable of communication with a receiver 1306 and a transmitter 1309 through a bus 1304 or other structures or devices. It should be understood that communication means other than busses can be utilized with the disclosed configurations. The processing system 1302 can generate audio, video, multimedia, and/or other types of data to be provided to the transmitter 1309 for communication. In addition, audio, video, multimedia, and/or other types of data can be received at the receiver 1306, and processed by the processing system 1302.

The processing system 1302 may include a processor for executing instructions and may further include a machine-readable medium 1319, such as a volatile or non-volatile memory, for storing data and/or instructions for software programs. The instructions, which may be stored in a machine-readable medium 1310 and/or 1319, may be executed by the processing system 1302 to control and manage access to the various networks, as well as provide other communication and processing functions. The instructions may also include instructions executed by the processing system 1302 for various user interface devices, such as a display 1312 and a keypad 1314. The processing system 1302 may include an input port 1322 and an output port 1324. Each of the input port 1322 and the output port 1324 may include one or more ports. The input port 1322 and the output port 1324 may be the same port (e.g., a bi-directional port) or may be different ports.

The processing system 1302 may be implemented using software, hardware, or a combination of both. By way of example, the processing system 1302 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium can be one or more machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media (e.g., 1319) may include storage integrated into a processing system, such as might be the case with an ASIC. Machine-readable media (e.g., 1310) may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the processing system 1302. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. In one aspect, a machine-readable medium is a non-transitory machine-readable medium, a machine-readable storage medium, or a non-transitory machine-readable storage medium. In one aspect, a computer-readable medium is a non-transitory computer-readable medium, a computer-readable storage medium, or a non-transitory computer-readable storage medium. Instructions may be executable, for example, by a client device or server or by a processing system of a client device or server. Instructions can be, for example, a computer program including code.

An interface 1316 may be any type of interface and may reside between any of the components shown in FIG. 17. An interface 1316 may also be, for example, an interface to the outside world (e.g., an Internet network interface). A transceiver block 1307 may represent one or more transceivers, and each transceiver may include a receiver 1306 and a transmitter 1309. A functionality implemented in a processing system 1302 may be implemented in a portion of a receiver 1306, a portion of a transmitter 1309, a portion of a machine-readable medium 1310, a portion of a display 1312, a portion of a keypad 1314, or a portion of an interface 1316, and vice versa.

Figure 18:
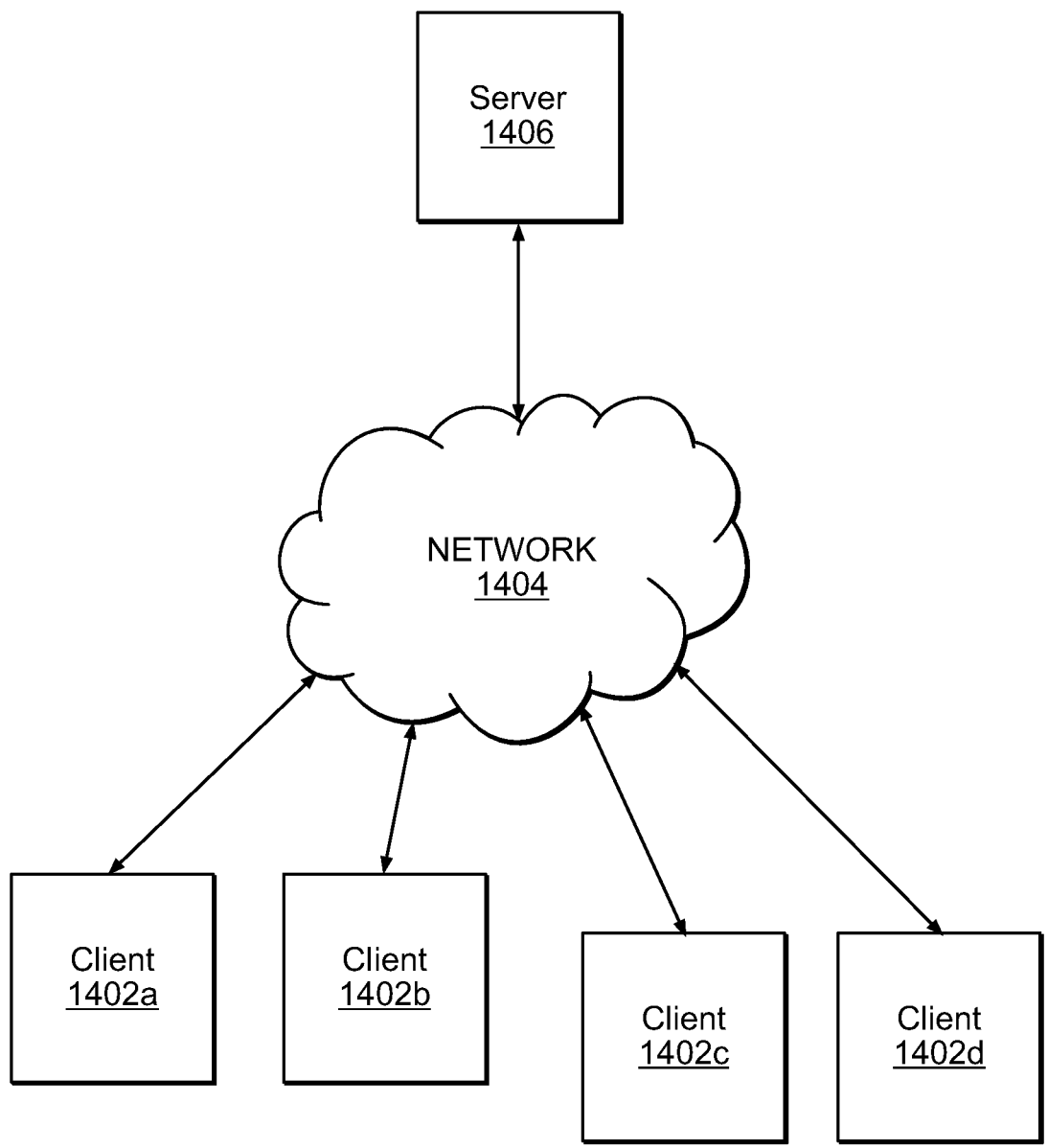
FIG. 18 is an exemplary diagram of a network in which systems and methods herein may be implemented.

FIG. 18 illustrates a simplified diagram of a system 1400, in accordance with various embodiments of the subject technology. The system 1400 may include one or more remote client devices 1402 (e.g., client devices 1402*a*, 1402*b*, 1402*c*, and 1402*d*) in communication with a server computing device 1406 (server) via a network 1404. In some embodiments, the server 1406 is configured to run applications that may be accessed and controlled at the client devices 1402. For example, a user at a client device 1402 may use a web browser to access and control an application running on the server 1406 over the network 1404. In some embodiments, the server 1406 is configured to allow remote sessions (e.g., remote desktop sessions) wherein users can access applications and files on the server 1406 by logging onto the server 1406 from a client device 1402. Such a connection may be established using any of several well-known techniques such as the Remote Desktop Protocol (RDP) on a Windows-based server.

By way of illustration and not limitation, in one aspect of the disclosure, stated from a perspective of a server side (treating a server as a local device and treating a client device as a remote device), a server application is executed (or runs) at a server 1406. While a remote client device 1402 may receive and display a view of the server application on a display local to the remote client device 1402, the remote client device 1402 does not execute (or run) the server application at the remote client device 1402. Stated in another way from a perspective of the client side (treating a server as remote device and treating a client device as a local device), a remote application is executed (or runs) at a remote server 1406.

By way of illustration and not limitation, a client device 1402 can represent a computer, a mobile phone, a laptop computer, a thin client device, a personal digital assistant (PDA), a portable computing device, or a suitable device with a processor. In one example, a client device 1402 is a smartphone (e.g., iPhone, Android phone, Blackberry, etc.). In certain configurations, a client device 1402 can represent an audio player, a game console, a camera, a camcorder, an audio device, a video device, a multimedia device, or a device capable of supporting a connection to a remote server. In one example, a client device 1402 can be mobile. In another example, a client device 1402 can be stationary. According to one aspect of the disclosure, a client device 1402 may be a device having at least a processor and memory, where the total amount of memory of the client device 1402 could be less than the total amount of memory in a server 1406. In one example, a client device 1402 does not have a hard disk. In one aspect, a client device 1402 has a display smaller than a display supported by a server 1406. In one aspect, a client device may include one or more client devices.

In some embodiments, a server 1406 may represent a computer, a laptop computer, a computing device, a virtual machine (e.g., VMware® Virtual Machine), a desktop session (e.g., Microsoft Terminal Server), a published application (e.g., Microsoft Terminal Server) or a suitable device with a processor. In some embodiments, a server 1406 can be stationary. In some embodiments, a server 1406 can be mobile. In certain configurations, a server 1406 may be any device that can represent a client device. In some embodiments, a server 1406 may include one or more servers.

In one example, a first device is remote to a second device when the first device is not directly connected to the second device. In one example, a first remote device may be connected to a second device over a communication network such as a Local Area Network (LAN), a Wide Area Network (WAN), and/or other network.

When a client device 1402 and a server 1406 are remote with respect to each other, a client device 1402 may connect to a server 1406 over a network 1404, for example, via a modem connection, a LAN connection including the Ethernet or a broadband WAN connection including DSL, Cable, T1, T3, Fiber Optics, Wi-Fi, or a mobile network connection including GSM, GPRS, 3G, WiMax or other network connection. A network 1404 can be a LAN network, a WAN network, a wireless network, the Internet, an intranet or other network. A network 1404 may include one or more routers for routing data between client devices and/or servers. A remote device (e.g., client device, server) on a network may be addressed by a corresponding network address, such as, but not limited to, an Internet protocol (IP)

address, an Internet name, a Windows Internet name service (WINS) name, a domain name or other system name. These illustrate some examples as to how one device may be remote to another device. But the subject technology is not limited to these examples.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or vice versa.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

Some features and aspects of the subject technology can be embodied in modules. As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable persons skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method for improving reinforcement learning by machine, the method comprising:
   detecting a motor signal having a characteristic and emanating from a primary motor cortex of a subject's brain;
   providing, to a device and based on (i) the motor signal and (ii) an instruction policy, a command signal resulting in a first action by the device;
   detecting an evaluation signal emanating from the primary motor cortex in response to the first action; and
   adjusting the policy based on the evaluation signal such that a subsequent motor signal, emanating from the primary motor cortex and having the characteristic, results in a second action, by the device, different from the first action,
   wherein the detecting steps are performed by one or more electrode array and the providing and the adjusting are performed by one or more processor.

2. The method of claim 1, wherein the device is a prosthetic device.

3. The method of claim 1, wherein the first action is a movement by the device.

4. The method of claim 1, wherein the device is a display and the first action is changing an appearance of the display.

5. The method of claim 1, wherein the device is a prosthetic limb, the first action comprises a first movement made by the prosthetic limb, and the second action comprises a second movement made by the prosthetic limb, wherein the first movement and the second movement are different in at least one of position, direction, rotation, duration, speed, or acceleration.

6. The method of claim 1, wherein the device comprises a speech generation device, the first action comprises a first sound generated by the speech generation device, and the second action comprises a second sound generated by the speech generation device, wherein the first sound and the second sound are different in at least one of pitch, volume, duration, or pronunciation.

7. The method of claim 1, wherein the primary motor cortex is a rostral primary motor cortex.

8. The method of claim 1, further comprising receiving a sensory signal from a sensory cortex of the subject's brain, wherein adjusting the policy is further based on the sensory signal.

9. The method of claim 1, wherein the command signal is generated from an algorithm of the policy.

10. The method of claim 1, further comprising
    providing, to the device, a calibration signal having a calibration characteristic, the calibration signal not emanating from the subject's brain;
    providing, to the device and based on (i) the calibration signal and (ii) the instruction policy, a calibration-command signal resulting in a third action by the device;
    detecting a calibration-evaluation signal emanating from the primary motor cortex in response to the third action; and
    adjusting the policy based on the calibration-evaluation signal such that a subsequent motor signal, emanating from the primary motor cortex and having the calibration characteristic, results in a fourth action, by the device, different from the third action.

11. The method of claim 10, wherein the device is a prosthetic device.

12. The method of claim 10, wherein the first action is a movement by the device.

13. The method of claim 10, wherein the device is a display and the first action is changing an appearance of the display.

14. The method of claim 10, wherein the device is a prosthetic limb, the first action comprises a first movement made by the prosthetic limb, and the second action comprises a second movement made by the prosthetic limb, wherein the first movement and the second movement are different in at least one of position, direction, rotation, duration, speed, or acceleration.

15. The method of claim 10, wherein the device comprises a speech generation device, the first action comprises a first sound generated by the speech generation device, and the second action comprises a second sound generated by the speech generation device, wherein the first sound and the second sound are different in at least one of pitch, volume, duration, or pronunciation.

16. The method of claim 10, wherein the primary motor cortex is a rostral primary motor cortex.

17. The method of claim 10, further comprising receiving a sensory signal from a sensory cortex of the subject's brain, wherein adjusting the policy is further based on the sensory signal.

18. The method of claim 10, wherein the command signal is generated from an algorithm of the policy.

19. The method of claim 10, wherein the subject is a mammal.

20. The method of claim 10, wherein the subject is a human.

21. The method of claim 1, wherein the subject is a mammal.

22. The method of claim 1, wherein the subject is a human.

* * * * *